(12) United States Patent
Ryu et al.

(10) Patent No.: US 12,005,706 B2
(45) Date of Patent: Jun. 11, 2024

(54) INKJET PRINTING DEVICE, PRINTING METHOD OF BIPOLAR ELEMENT, AND MANUFACTURING METHOD OF DISPLAY DEVICE

(71) Applicant: Samsung Display Co., LTD., Yongin-si (KR)

(72) Inventors: An Na Ryu, Hwaseong-si (KR); Jin Oh Kwag, Yongin-si (KR); Heung Cheol Jeong, Hwaseong-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 183 days.

(21) Appl. No.: 17/786,931

(22) PCT Filed: Jun. 5, 2020

(86) PCT No.: PCT/KR2020/007366
§ 371 (c)(1),
(2) Date: Jun. 17, 2022

(87) PCT Pub. No.: WO2021/125465
PCT Pub. Date: Jun. 24, 2021

(65) Prior Publication Data
US 2023/0047796 A1   Feb. 16, 2023

(30) Foreign Application Priority Data
Dec. 17, 2019   (KR) .................. 10-2019-0168974

(51) Int. Cl.
*B41J 2/18*   (2006.01)
*B41J 2/045*   (2006.01)
(Continued)

(52) U.S. Cl.
CPC .......... *B41J 2/04561* (2013.01); *B41J 2/125* (2013.01); *B41J 2/18* (2013.01); *B41M 5/0023* (2013.01)

(58) Field of Classification Search
None
See application file for complete search history.

(56) References Cited

U.S. PATENT DOCUMENTS

2011/0175219 A1   7/2011   Cellura et al.
2018/0178568 A1   6/2018   Xiao

FOREIGN PATENT DOCUMENTS

CN   1741693 A   *   3/2006   ............. C09D 11/30
JP   2010-506744   3/2010
(Continued)

OTHER PUBLICATIONS

Jung Ji, Machine Translation of KR-20190070265-A, 2019 (Year: 2019).*

(Continued)

*Primary Examiner* — Scott A Richmond
(74) *Attorney, Agent, or Firm* — KILE PARK REED & HOUTTEMAN PLLC

(57) ABSTRACT

An inkjet printing device includes a stage; an inkjet head disposed above the stage and comprising nozzles through which ink is discharged, the ink including bipolar elements extending in a direction; an ink circulation part which supplies the ink to the inkjet head, and to which the ink remaining after being discharged from the inkjet head is supplied; and at least one sensing part disposed between the inkjet head and the ink circulation part and sensing a number of the bipolar elements that are discharged through the nozzles.

20 Claims, 36 Drawing Sheets

(51) Int. Cl.
B41J 2/125 (2006.01)
B41M 5/00 (2006.01)

(56) References Cited

FOREIGN PATENT DOCUMENTS

| | | | |
|---|---|---|---|
| JP | 2014-140810 | | 8/2014 |
| JP | 2019-48452 | | 3/2019 |
| KR | 10-2006-0088373 | | 8/2006 |
| KR | 10-2010-0039276 | | 4/2010 |
| KR | 10-2012-0000835 | | 1/2012 |
| KR | 10-2012-0067070 | | 6/2012 |
| KR | 10-1781500 | | 9/2017 |
| KR | 10-2018-0055021 | | 5/2018 |
| KR | 20180055021 A | * | 5/2018 |
| KR | 10-2018-0104548 | | 9/2018 |
| KR | 10-2018-0117899 | | 10/2018 |
| KR | 20190070265 A | * | 6/2019 |

OTHER PUBLICATIONS

Im Hyun Deck, MachineTranslationofKR-20180055021-A, 2018 (Year: 2018).*
Arai, MachineTranslationofCN-1741693-A, 2006 (Year: 2006).*
International Search Report, with English translation, corresponding to International Application No. PCT/KR2020/007366 dated Sep. 4, 2020.
Written Opinion, with English translation, corresponding to International Application No. PCT/KR2020/007366, dated Sep. 4, 2020.

* cited by examiner

INKJET PRINTING DEVICE, PRINTING METHOD OF BIPOLAR ELEMENT, AND MANUFACTURING METHOD OF DISPLAY DEVICE

CROSS-REFERENCE TO RELATED APPLICATION(S)

This application is a national entry of International Application No. PCT/KR2020/007366, filed on Jun. 5, 2020, which claims under 35 U.S.C. §§ 119(a) and 365(b) priority to and benefits of Korean Patent Application No. 10-2019-0168974, filed on Dec. 17, 2019, in the Korean Intellectual Property Office (KIPO), the entire contents of which are incorporated herein by reference.

BACKGROUND

1. Technical Field

The disclosure relates to an inkjet printing device, a printing method of a bipolar element, and a manufacturing method of a display device.

2. Description of Related Art

The importance of display devices has steadily increased with the development of multimedia technology. In response thereto, various types of display devices such as an organic light emitting display (OLED), a liquid crystal display (LCD) and the like have been used.

A display device is a device for displaying an image, and includes a display panel, such as an organic light emitting display panel or a liquid crystal display panel. The light emitting display panel may include light emitting elements, e.g., light emitting diodes (LED), and examples of the light emitting diode include an organic light emitting diode (OLED) using an organic material as a fluorescent material and an inorganic light emitting diode using an inorganic material as a fluorescent material.

SUMMARY

Aspects of the disclosure provide an inkjet printing device including a uniform number of bipolar elements per unit droplet of ejected ink.

Aspects of the disclosure also provide a printing method of a bipolar element using an inkjet printing device which can maintain a uniform number of bipolar elements dispersed in a unit droplet, and a method of manufacturing a display device including a light emitting element.

It should be noted that aspects of the disclosure are not limited thereto and other aspects, which are not mentioned herein, will be apparent to those of ordinary skill in the art from the following description.

According to an embodiment of the disclosure, an inkjet printing device comprises a stage, an inkjet head disposed above the stage and comprising nozzles through which ink is ejected, the ink comprising bipolar elements extending in a direction, an ink circulation part supplying the ink to the inkjet head, and supplied with the ink remaining after the ink is ejected from the inkjet head, and at least one sensing part disposed between the inkjet head and the ink circulation part and measuring a number of the bipolar elements ejected through the nozzles.

The at least one sensing part may comprise a light emitting part emitting light to the ink and a light receiving part spaced apart from and facing the light emitting part and receiving the light emitted from the light emitting part.

An outer wall of the nozzles may be made of at least one transparent material, at least part of the light emitted to the ink is scattered by the bipolar elements, and the light receiving part may measure the number of the bipolar elements by receiving the light emitted from the light emitting part and the scattered light.

The at least one sensing part may detect a change in the number of the bipolar elements in the ejected ink, and the ink circulation part may receive the detected change in the number of bipolar elements from the at least one sensing part.

The inkjet printing device may further comprise connection tubes connecting the ink circulation part and the inkjet head, wherein the at least one sensing part may be disposed on the connection tube.

The inkjet head may comprise a base part, an ejecting part which is a portion of the base part and in which the nozzles are disposed, an inner tube supplied with the ink, the light emitting part and the light receiving part of the at least one sensing part disposed on the ejecting part, and at least one of the nozzles may be disposed between the light emitting part and the light receiving part of the at least one sensing part.

Each of the nozzles may comprise an inlet connected to the inner tube and through which the ink is introduced, and an outlet connected to the inlet and through which the ink is ejected, the inkjet head may further comprise an actuator disposed on the ejecting part and surrounding the nozzles, and the at least one sensing part may comprise a first sensing part disposed between the actuator and the inner tube and adjacent to the inlet of the at least one of the nozzles.

The at least one sensing part may further comprise a second sensing part spaced apart from the first sensing part, and the actuator may be disposed between the first and second sensing parts and adjacent to the outlet.

The at least one sensing part may further comprise a third sensing part in which the light emitting part, and the light receiving part may be disposed on the base part, the inner may be disposed between the third sensing part and the base part.

The light receiving part may be disposed in the ejecting part, the light emitting part may be disposed on an outer surface of the base part, and the at least one sensing part may further comprise a light transmitting part disposed in the ejecting part, disposed between the at least one nozzles and the light emitting part, and transmitting the light emitted from the light emitting part into the at least one of the nozzles.

The inkjet head may further comprise an electric field generating electrode generating an electric field in the nozzles.

According to an embodiment of the disclosure, a printing method of a bipolar element, comprising preparing an ink circulation part storing ink in which bipolar elements are dispersed and supplying the ink to an inkjet head, ejecting the ink from the inkjet head and measuring a number of bipolar elements in the ejected ink, and controlling the number of the bipolar elements in the ink supplied to the inkjet head in case that the number of the bipolar elements in the ink exceeds a reference set value.

The measuring of the number of the bipolar elements may be performed by at least one sensing part disposed between the inkjet head and the ink circulation part, and the at least one sensing part may comprise a light emitting part emitting light to the ink, and a light receiving part spaced apart from and facing the light emitting part and receiving the light emitted from the light emitting part.

At least part of the light emitted to the ink may be scattered by the bipolar elements, and the light receiving part may measure the number of the bipolar elements by being irradiated with the light emitted from the light emitting part and the scattered light.

The controlling of the number of the bipolar elements in the ink may comprise receiving, at the ink circulation part, a change in the number of the bipolar elements detected by the at least one sensing part, and controlling, at the ink circulation part, a degree of dispersion of the bipolar elements in the ink.

The printing method may further comprise spraying the ink ejected from the inkjet head onto a target substrate and disposing the bipolar elements on the target substrate.

The spraying of the bipolar elements onto the target substrate may be conducted using an inkjet printing device, wherein the inkjet printing device may comprise a stage, the inkjet head disposed above the stage and comprising nozzles through which the ink is ejected, the ink comprising the bipolar elements extending in a direction, the ink circulation part supplying the ink to the inkjet head, and supplied with the ink remaining after the ink is ejected from the inkjet head, and the at least one sensing part disposed between the inkjet head and the ink circulation part and measuring the number of the bipolar elements ejected through the nozzles.

According to an embodiment of the disclosure, a method of manufacturing a display device, comprising preparing a target substrate on which a first electrode and a second electrode are formed, spraying ink in which light emitting elements are dispersed onto the target substrate while controlling a number of the light emitting elements dispersed in the ink, and disposing the light emitting elements onto the first electrode and the second electrode.

The controlling of the number of the light emitting elements dispersed in the ink may comprise measuring the number of the light emitting elements in the ink sprayed onto the target substrate, and controlling the number of the light emitting elements dispersed in the ink in case that the number of the light emitting elements in the ink exceeds a reference set value.

The measuring of the number of the light emitting elements may comprise emitting light to the ink, and receiving the light and scattered light scattered by the light emitting element from at least part of the light emitted to the ink and measuring the number of the light emitting elements from the light and the scattered light.

The details of other embodiments are included in the detailed description and the accompanying drawings.

An inkjet printing device according to an embodiment includes a sensing part capable of measuring the number of bipolar elements in ejected ink. The sensing part includes a light emitting part and a light receiving part and may measure the number of bipolar elements in ink by using light scattered by the bipolar elements in the ink irradiated with light. In addition, a change in the number of bipolar elements may be detected while ejecting ink, and the detection result is fed back to control the number of bipolar elements in the ink.

Accordingly, a printing method of bipolar elements using the inkjet printing device according to an embodiment may allow a uniform number of bipolar elements per unit droplet of ejected ink to be maintained, and a display device including light emitting elements which is manufactured using the inkjet printing device may improve emission reliability for each pixel.

The effects according to the embodiments are not limited by the contents exemplified above, and more various effects are included in this disclosure.

DETAILED DESCRIPTION OF THE EMBODIMENTS

The disclosure will now be described more fully hereinafter with reference to the accompanying drawings, in which embodiments of the disclosure are shown. This disclosure may, however, be embodied in different forms and should not be construed as limited to the embodiments set forth herein. Rather, these embodiments are provided so that this disclosure will be thorough and complete, and will fully convey the scope of the disclosure to those skilled in the art.

It will also be understood that when a layer is referred to as being "on" another layer or substrate, it can be directly on the other layer or substrate, or intervening layers may also be present. The same reference numbers indicate the same components throughout the specification.

It will be understood that, although the terms "first," "second," etc. may be used herein to describe various elements, these elements should not be limited by these terms. These terms are only used to distinguish one element from another element. For instance, a first element discussed below could be termed a second element without departing from the teachings of the disclosure. Similarly, the second element could also be termed the first element.

Unless otherwise defined or implied herein, all terms (including technical and scientific terms) used herein have the same meaning as commonly understood by those skilled in the art to which this disclosure pertains. It will be further understood that terms, such as those defined in commonly used dictionaries, should be interpreted as having a meaning that is consistent with their meaning in the context of the relevant art and the disclosure, and should not be interpreted in an ideal or excessively formal sense unless clearly so defined herein.

Hereinafter, embodiments will be described with reference to the accompanying drawings.

Figure 1:
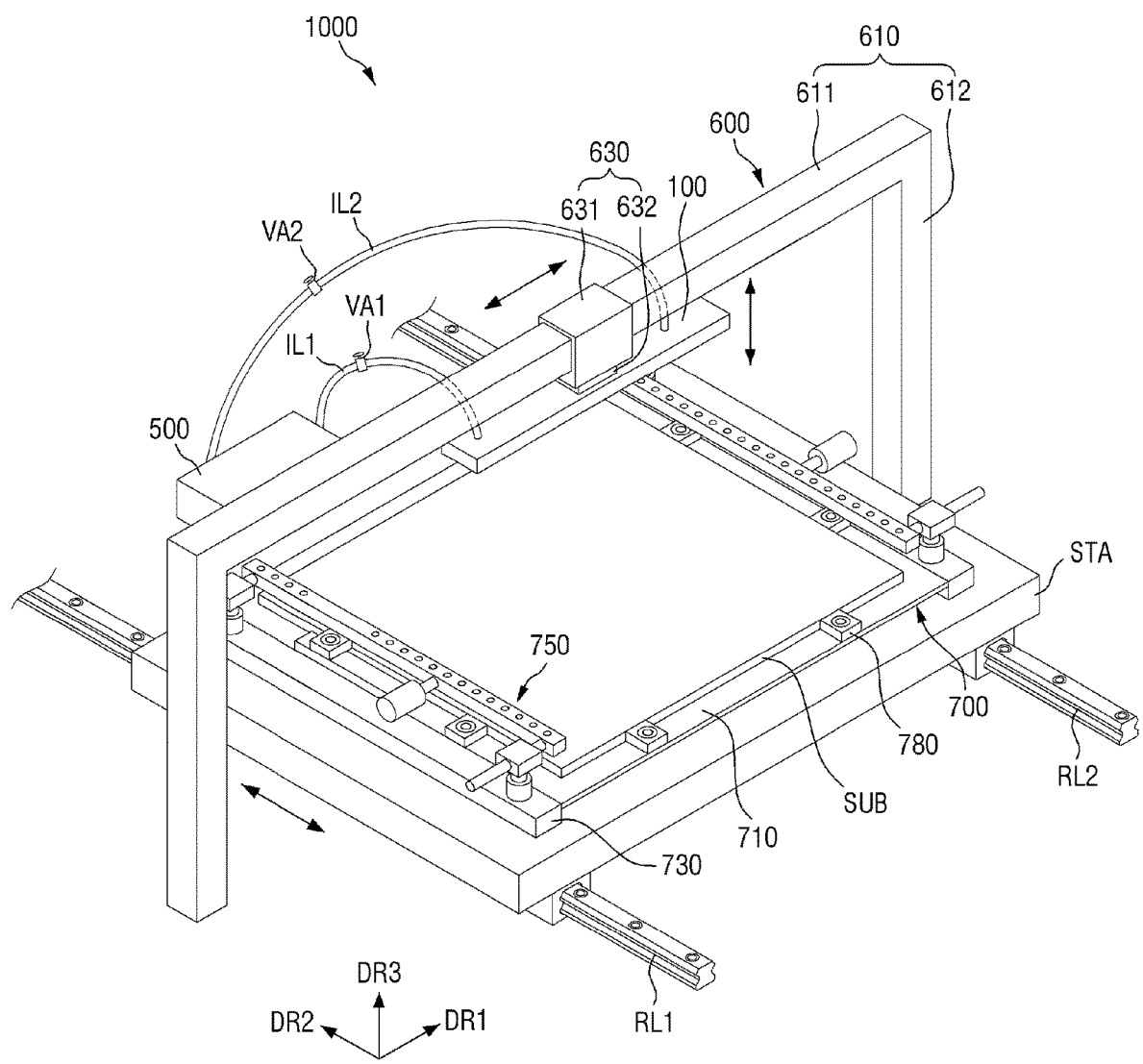
FIG. 1 is a schematic perspective view of an inkjet printing device according to an embodiment.
Figure 2:
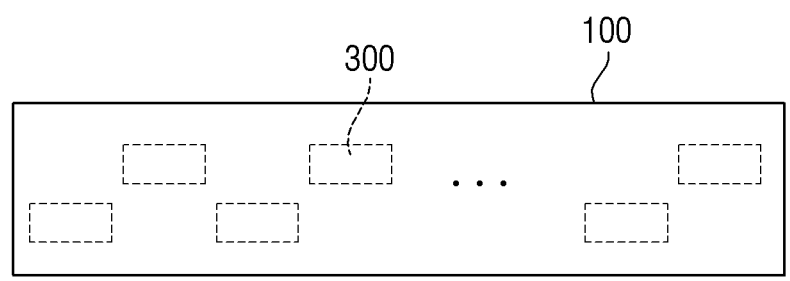
FIG. 2 is a schematic bottom view of a printhead part according to an embodiment.
Figure 2:
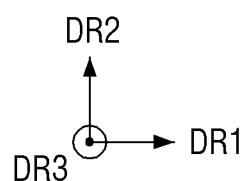
Figure 3:
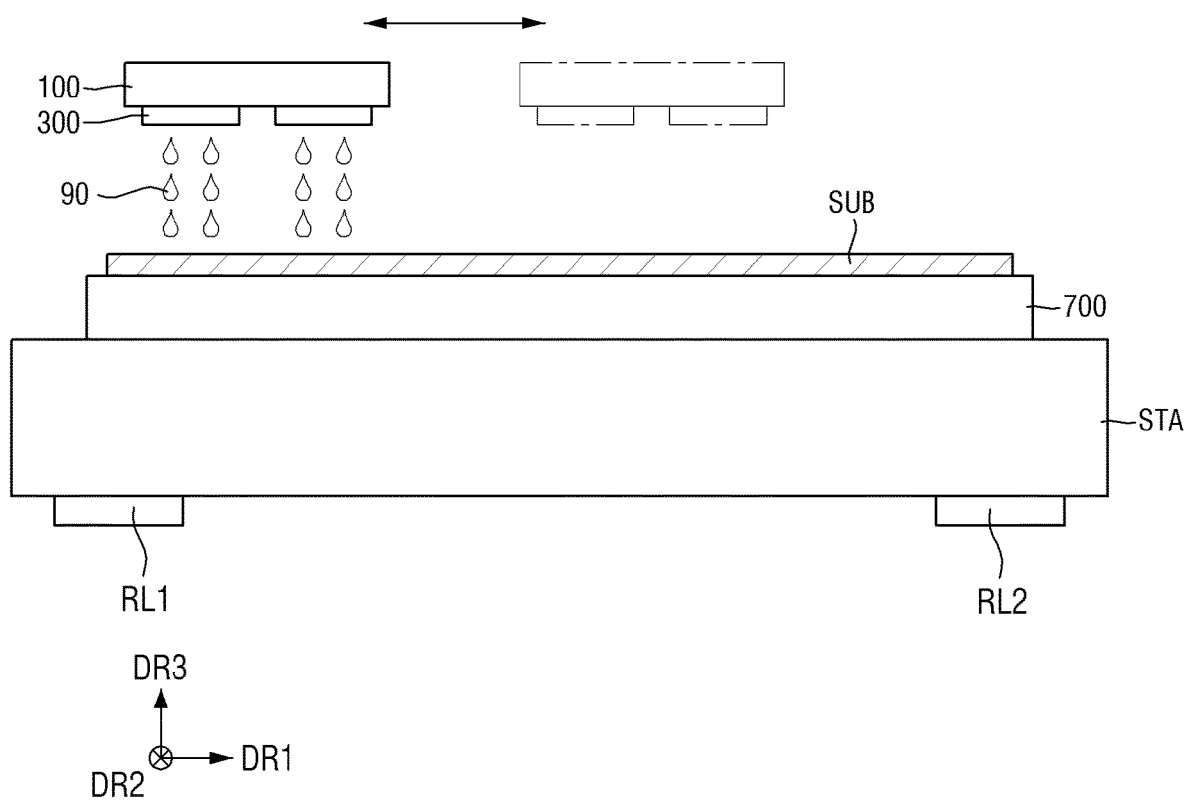
FIG. 3 is a schematic diagram illustrating an operation of a printhead part according to an embodiment.
Figure 4:
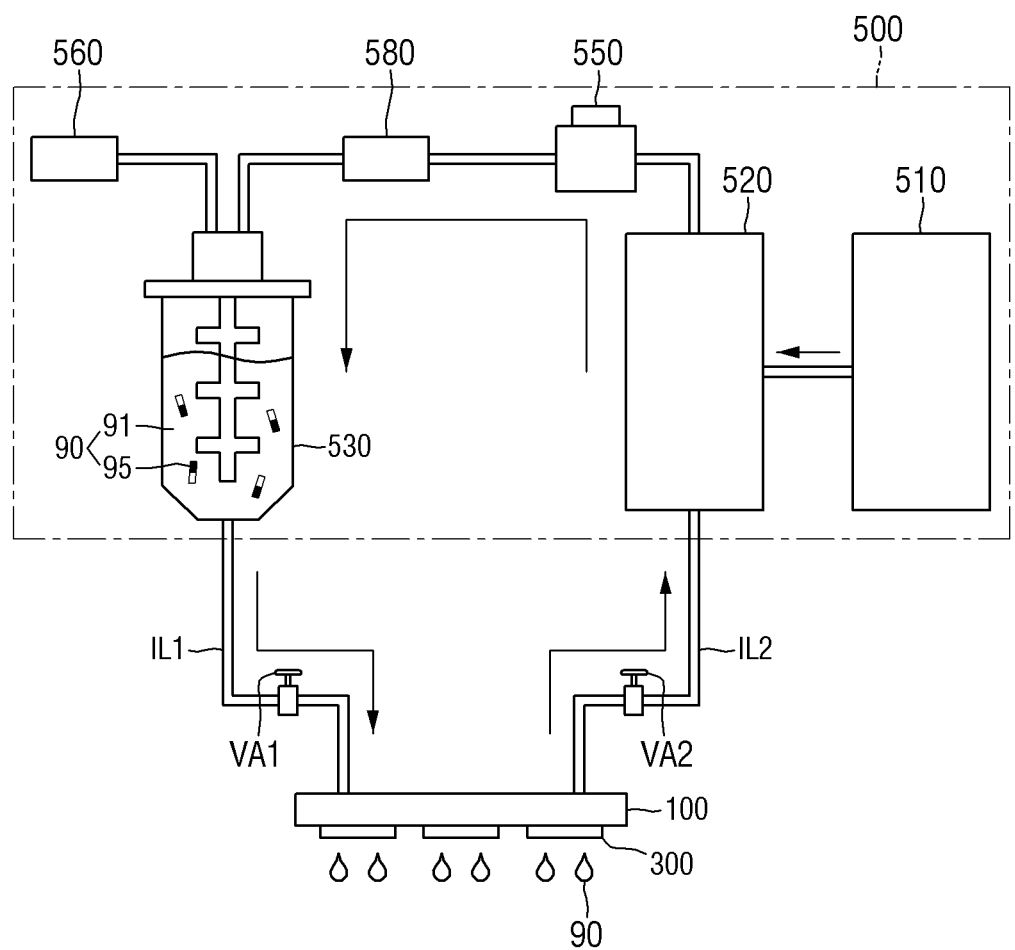
FIG. 4 is a schematic diagram illustrating an ink circulation part and a printhead part according to an embodiment.

FIG. 1 is a schematic plan view of an inkjet printing device according to an embodiment. FIG. 2 is a schematic view of a printhead part according to an embodiment. FIG. 3 is a schematic diagram illustrating an operation of a printhead part according to an embodiment. FIG. 4 is a schematic diagram illustrating an ink circulation part and a printhead part according to an embodiment. FIG. 3 illustrates a printhead part 100 according to an embodiment and a probe device 700 disposed on a stage STA when viewed from the front.

Referring to FIGS. 1 to 4, an inkjet printing device 1000 according to an embodiment includes a printhead part 100 including inkjet heads 300. The inkjet printing device 1000 may further include a stage STA, an ink circulation part 500, a probe device 700, and a base frame 600.

In FIG. 1, a first direction DR1, a second direction DR2, and a third direction DR3 are defined. The first direction DR1 and the second direction DR2 are located on a same plane and cross each other orthogonally, and the third direction DR3 is perpendicular to each of the first and second directions DR1 and DR2. The first direction DR1 may refer to a horizontal direction in the drawing, the second direction DR2 may refer to a vertical direction in the drawing, and the third direction DR3 may refer to an upward/downward direction.

The inkjet printing device 1000 may spray ink 90 onto a target substrate SUB by using the printhead part 100. The probe device 700 may generate an electric field on the target substrate SUB onto which the ink 90 is sprayed, and particles, such as bipolar elements, included in the ink may be aligned on the target substrate SUB.

The target substrate SUB may be provided on the probe device 700, the probe device 700 forms an electric field on the target substrate SUB, and the electric field may be transferred to the ink 90 sprayed onto the target substrate SUB. The particles, such as bipolar elements 95, included in the ink 90 may have a shape extending in a direction, and may be aligned by the electric field so that the extending direction is oriented in a direction.

The inkjet printing device 1000 according to an embodiment may include an inkjet head 300 and a sensing part (or detection part) 400 (see FIG. 5) at least between the ink circulation part 500 and the inkjet head 300. The inkjet head 300 may spray, eject, or print the ink 90 containing the bipolar elements 95 onto the target substrate SUB, and the sensing part 400 may detect the number of bipolar elements 95 in the ink 90 printed or ejected from the inkjet head 300. The inkjet printing device 1000 may detect a change in the number of bipolar elements 95 in the ejected ink 90, and feed it back, thereby maintaining a uniform number of bipolar elements 95 per unit droplet of the ink 90 ejected from the inkjet head 300. Hereinafter, the inkjet printing device 1000 will be described in detail with reference to the drawings.

The stage STA may provide an area in which the probe device 700 is disposed. The inkjet printing device 1000 may include a first rail RL1 and a second rail RL2 that extend in the second direction DR2, and the stage STA is disposed on the first rail RL1 and the second rail RL2. The stage STA may move in the second direction DR2 through a separate moving member on the first rail RL1 and the second rail RL2. The probe device 700 may move in the second direction DR2 together with the stage STA and pass through the printhead part 100, and the ink 90 may be sprayed thereon. However, the disclosure is not limited thereto. Although the structure in which the stage STA moves is illustrated in the drawing, in some embodiments, the stage STA may be fixed and the printhead part 100 may be movable. In this case, the printhead part 100 may be mounted on a frame disposed on the first rail RL1 and the second rail RL2.

The printhead part 100 may include inkjet heads 300 and may be disposed on the base frame 600. The printhead part 100 may spray the ink 90 onto the target substrate SUB provided to the probe device 700 by using the inkjet head 300 extended to a separate ink reservoir.

The base frame 600 may include a support 610 and a moving part 630. The support 610 may include a first support 611 extending in the first direction DR1 that is a horizontal direction, and a second support 612 connected to (or extended to) the first support 611 and extending in the third direction DR3 that is a vertical direction. The extending direction of the first support 611 may be the same as the first direction DR1 that is the long side direction of the probe device 700. The printhead part 100 may be disposed on the moving part 630 mounted on the first support 611.

The moving part 630 may include a moving part 631 mounted on the first support 611 and movable in a direction, and a fixing part 632 disposed on a lower surface of the moving part 631 and having the printhead part 100 disposed thereto. The moving part 631 may move in the first direction DR1 on the first support 611, and the printhead part 100 may be fixed to the fixing part 632 and move in the first direction DR1 together with the moving part 631.

The printhead part 100 may be disposed on the base frame 600 and may spray the ink 90 provided from the ink reservoir onto the target substrate SUB through the inkjet head 300. The printhead part 100 may be spaced apart from the stage STA passing under the base frame 600 by a specific distance. The distance between the printhead part 100 and the stage STA may be adjusted by the height of the second support 612 of the base frame 600. The distance between the printhead part 100 and the stage STA may be adjusted within a range that allows the printhead part 100 to be spaced apart from the target substrate SUB by a certain distance to secure a space for printing process in case that the probe device 700 and the target substrate SUB are mounted on the stage STA.

According to an embodiment, the printhead part 100 may include an inkjet head 300 including nozzles 350. The inkjet head 300 may be disposed on a lower surface of the printhead part 100.

The inkjet heads 300 may be disposed to be spaced apart from each other in a direction, and may be disposed in a row or rows. FIG. 2 illustrates that the inkjet heads 300 are arranged in two rows, and the inkjet heads 300 of each row are alternately arranged. However, the disclosure is not limited thereto, and the inkjet heads 300 may be arranged in more rows or may be arranged to overlap each other instead of being alternately arranged. The shape of the inkjet head 300 is not particularly limited, but as an example, the inkjet head 300 may have a quadrilateral shape.

At least one inkjet head 300, e.g., two inkjet heads 300, may form a single pack and may be disposed adjacent to each other. However, the number of inkjet heads 300 included in a single pack is not limited thereto, and for example, the number of inkjet heads 300 included in a single pack may be in a range of about 1 to about 5. In addition, it is illustrated in the drawing that only six of inkjet heads 300 are disposed in the printhead part 100, but this is merely a schematic illustration of the printhead part 100, and the number of inkjet heads 300 is not limited thereto.

The inkjet head 300 disposed in the printhead part 100 may spray the ink 90 onto the target substrate SUB disposed above the stage STA. According to an embodiment, the printhead part 100 may move on the first support 611 in a direction, and the inkjet head 300 may move in a direction and spray the ink 90 onto the target substrate SUB.

The printhead part 100 may move in the first direction DR1 in which the first support 611 is extended, and the inkjet head 300 may move in the first direction DR1 and spray the ink 90 onto the target substrate SUB.

In an embodiment, the ink 90 may contain a solvent 91 and bipolar elements 95 included in the solvent 91. In an embodiment, the ink 90 may be provided in the form of a solution or colloid. For example, the solvent 91 may include acetone, water, alcohol, toluene, propylene glycol (PG), propylene glycol methyl acetate (PGMA), or the like, but the disclosure is not limited thereto. The bipolar elements 95 may be included in a dispersed state in the solvent 35 and may be supplied to the printhead part 100 so as to be ejected.

In some embodiments, the width of the target substrate SUB measured in the first direction DR1 may be greater than the width of the printhead part 100. In this case, the printhead part 100 may move in the first direction DR1 and spray the ink 90 over the entire surface of the target substrate SUB. In addition, in case that target substrates SUB are provided onto the probe device 700, the printhead part 100 may move in the first direction DR1 and spray the ink 90 onto each of the plurality of target substrates SUB.

However, the disclosure is not limited thereto, and the printhead part 100 may be positioned outside the first rail RL1 and the second rail RL2, move in the first direction DR1, and spray the ink 90 onto the target substrate SUB. In case that the stage STA moves in the second directions DR2 and is located under the base frame 600, the printhead part 100 may move between the first rail RL1 and the second rail RL2 and spray the ink 90 through the inkjet head 300. The operation of the inkjet head 300 is not limited thereto, and may vary within a range that allows a similar process to be implemented.

The inkjet printing device 1000 may further include the ink circulation part 500. The ink circulation part 500 may supply the ink 90 to the printhead part 100, and the inkjet head 300 may eject the supplied ink 90. The ink 90 may circulate between the ink circulation part 500 and the inkjet head 300, and part of the ink 90 supplied to the inkjet head 300 may be ejected from the inkjet head 300, and the remaining ink may be supplied again to the ink circulation part 500.

The ink circulation part 500 may be connected to the inkjet head 300 via a first connection tube IL1 and a second connection tube IL2. For example, the ink circulation part 500 may supply the ink 90 to the inkjet head 300 through the first connection tube ILL and the flow rate of the ink 90 supplied may be adjusted using a first valve VA1. In addition, the remaining ink 90 after the ink is ejected from the inkjet head 300 may be supplied to the ink circulation part 500 through the second connection tube IL2. The flow rate of the ink 90 supplied to the ink circulation part 500 through the second connection tube IL2 may be adjusted using a second valve VA2. The circulation of the ink 90 through the ink circulation part 500 may minimize a deviation in the number of bipolar elements 95 included in the ink 90 ejected from the inkjet head 300.

FIG. 1 illustrates that the ink circulation part 500 is mounted on the base frame 600, but the disclosure is not limited thereto. The ink circulation part 500 is provided in the inkjet printing device 1000, but the position or shape thereof is not particularly limited. For example, the ink circulation part 500 may be disposed through a separate device, and may be variously disposed as long as the ink circulation part 500 is connected to (or extended to) the inkjet head 300.

In some embodiments, the ink circulation part 500 may include a first ink reservoir 510, a second ink reservoir 520, a third ink reservoir 530, a pressure pump 550, a compressor 560, and a flow meter 580. In the ink circulation part 500, the second ink reservoir 520, the pressure pump 550, and the third ink reservoir 530 may be connected to the inkjet head 300, and they may form an ink circulation system.

The first ink reservoir 510 may be a reservoir in which the manufactured ink 90 is prepared. The ink 90 containing the solvent 91 and the bipolar elements 95 is prepared in the first ink reservoir 510 of the ink circulation part 500, and the ink 90 may be supplied to the ink circulation system.

The second ink reservoir 520 may be connected to the first ink reservoir 510 and be supplied with the prepared ink 90. Also, the remaining ink 90 after the ink is ejected from the inkjet head 300 may be supplied to the second ink reservoir 520 through the second connection tube IL2. The second ink reservoir 520 may be positioned between the third ink reservoir 530, the inkjet head 300, and the first ink reservoir 510 to form an ink circulation system. In case that the second ink reservoir 520 is omitted, an excessive amount of ink 90 is supplied to the third ink reservoir 530, so that the bipolar elements 95 may not be smoothly dispersed. The ink circulation part 500 may further include the second ink reservoir 520 to prevent excessive supply of ink 90 to the third ink reservoir 530. For example, the second ink reservoir 520 may serve as a buffer storage in which part of the ink 90 circulated in the ink circulation system is stored.

The ink 90 supplied to the second ink reservoir 520 may be supplied to the third ink reservoir 530 through the pressure pump 550. The pressure pump 550 may be a pump that transmits power to a fluid so that the ink 90 in the ink circulation system can be circulated. The ink 90 supplied to the second ink reservoir 520 may be supplied to the third ink reservoir 530 by the pressure pump 550. The flow meter 580 may be provided between the pressure pump 550 and the third ink reservoir 530, and the flow meter 580 may measure the flow rate of the ink 90 supplied to the third ink reservoir 530. The pressure pump 550 may adjust the flow rate of the ink 90 supplied to the third ink reservoir 530 according to the flow rate of the ink 90 measured by the flow meter 580.

In addition, the ink circulation part 500 may further include the compressor 560 and the compressor 560 may adjust the pressure in the third ink reservoir 530. The compressor 560 may remove gas from the third ink reservoir 530 so that the inside of the third ink reservoir 530 is in a vacuum state, or may introduce an external inert gas to have a pressure. However, the disclosure is not limited thereto, and the compressor 560 of the ink circulation part 500 may be omitted.

The third ink reservoir 530 may be connected to the second ink reservoir 520 through the pressure pump 550 and be supplied with the ink 90. Also, the third ink reservoir 530 may supply the ink 90 to the inkjet head 300 through the first connection tube IL1. In an embodiment, the third ink reservoir 530 may include a stirrer ST, and the stirrer ST may disperse the bipolar elements 95 in the ink 90. As the stirrer ST rotates, the bipolar elements 95 in the ink 90 supplied to the third ink reservoir 530 may not settle and may be kept dispersed. For example, the stirrer ST of the third ink reservoir 530 may prevent the bipolar elements 95 from settling to the bottom of the third ink reservoir 530, thus preventing a reduction in the number of bipolar elements 95 in the ink 90 ejected through the inkjet head 300. The third ink reservoir 530 may supply the ink 90 in which the bipolar elements 95 is smoothly dispersed to the inkjet head 300, and the inkjet head 300 may eject the ink 90 including a number or more of bipolar elements 95.

In the inkjet printing device 1000, a volume per ink droplet of the ink 90 ejected from the inkjet head 300 is required to be constant, and at the same time it is required to control the number of bipolar elements 95 dispersed in the volume per ink droplet to be uniform. If the number of bipolar elements 95 per unit droplet of the ink 90 is not uniform while the ink 90 is ejected from the inkjet head 300 by the ink circulation system, the reliability of the inkjet printing device 1000 may be questioned. According to an embodiment, the inkjet printing device 1000 includes at least one sensing part 400 (see FIG. 5) disposed between the ink circulation part 500 and the inkjet head 300, and the sensing part 400 may measure the number of bipolar elements 95 in the ink 90 ejected from the inkjet head 300. The inkjet printing device 1000 may detect a change in the number of bipolar elements 95 in the ink 90, and feed it back to the ink circulation part 500 or the inkjet head 300, so that a uniform number of bipolar elements 95 per unit droplet of the ink 90 can be maintained. Hereinafter, the inkjet head 300 and the sensing part 400 will be described in greater detail.

Figure 5:
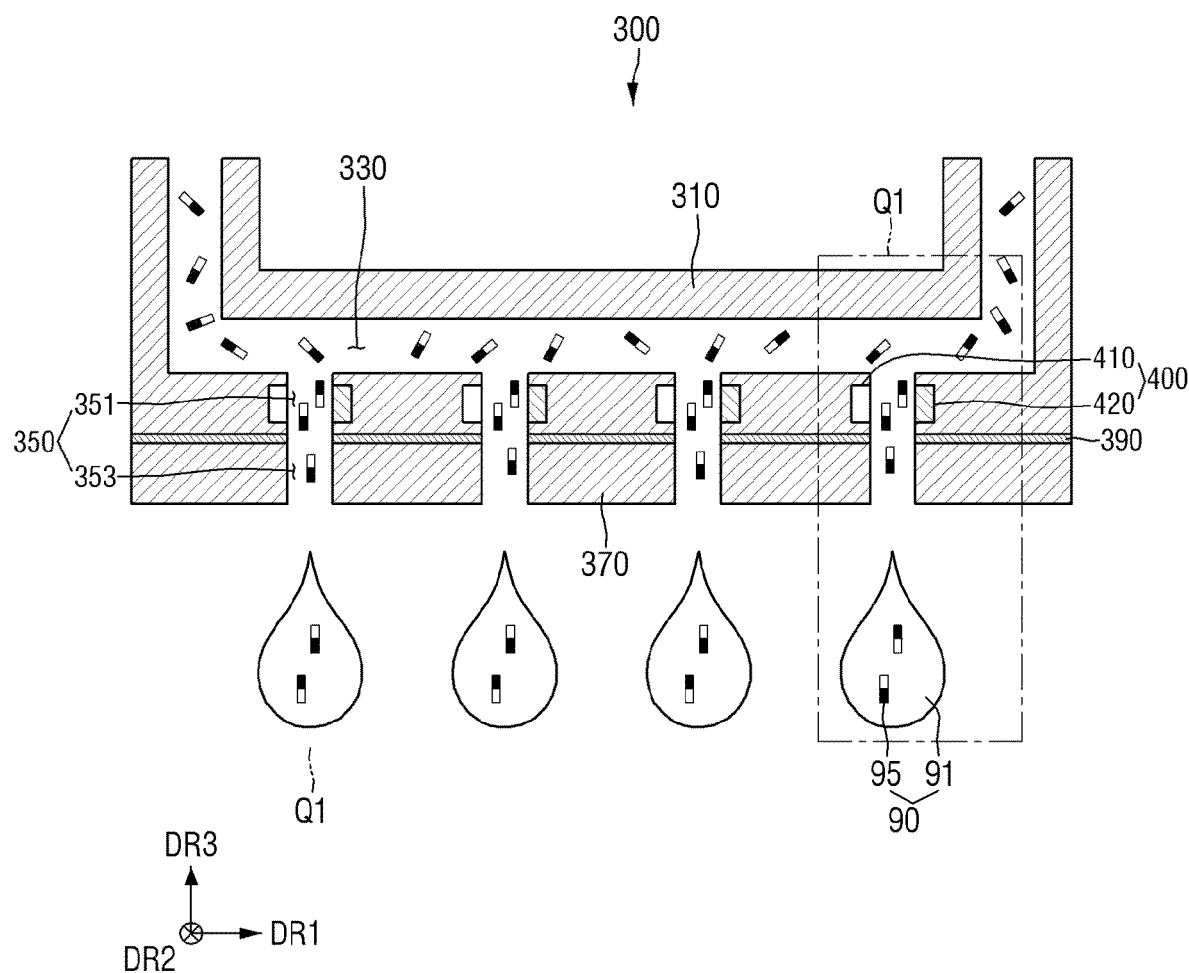
FIG. 5 is a schematic cross-sectional view of an inkjet head according to an embodiment.

FIG. 5 is a schematic cross-sectional view of an inkjet head according to an embodiment. FIG. 5 is a schematic enlarged view of portion Q1 of FIG. 5.

Figure 6:
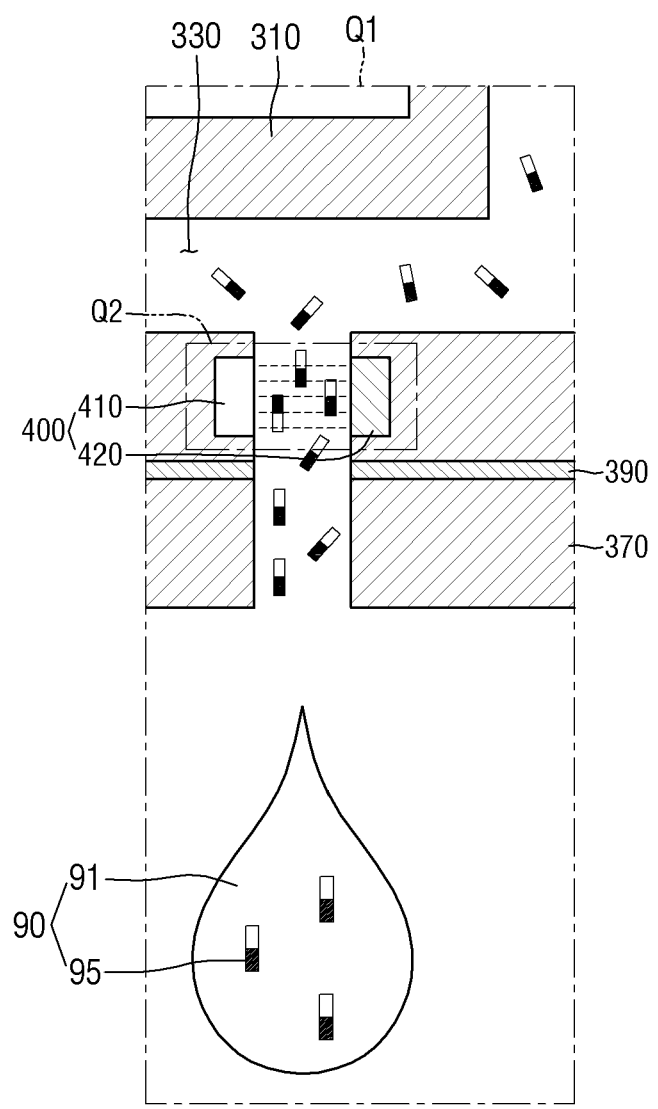
FIG. 6 is a schematic enlarged view of portion Q1 of FIG. 5.

Referring to FIGS. 5 and 6, the inkjet head 300 may include nozzles 350 and eject the ink 90 through the nozzles 350. The ink 90 ejected from the nozzles 350 may be sprayed onto the target substrate SUB provided on the stage STA or the probe device 700. The nozzles 350 may be located on the bottom surface of the inkjet head 300 and may be arranged in a direction in which the inkjet head 300 extends.

The inkjet head 300 may include a base part 310, an inner tube 330, and nozzles 350. The inkjet head 300 may further include an ejecting part 370 and an actuator 390. In some embodiments, the sensing part 400 may be disposed in the inkjet head 300.

The base part 310 may constitute a main body of the inkjet head 300. The base part 310 may be attached to the printhead part 100. As described above with reference to FIG. 2, the base part 310 may have a shape extending in the first direction DR1 and the second direction DR2. However, the disclosure is not limited thereto, and the base part 310 may have a circular shape.

The ejecting part 370 may be a portion of the base part 310 of the inkjet head 300, in which the nozzle 350 is disposed. It is illustrated in the drawings that the ejecting part 370 connected to the base part 310 and the ejecting parts 370 spaced apart therefrom are disposed and the nozzles 350 are formed therebetween. However, the ejecting parts 370 may not be spaced apart from each other and may be substantially a single integral member, and the nozzle 350 may be formed in the shape of a hole passing through the ejecting part 370. For example, the ejecting parts 370 may be formed as a single member without being spaced apart from each other. However, the disclosure is not limited thereto, and in some embodiments, parts each including the ejecting part 370 in which the nozzle 350 is formed may be disposed in the inkjet head 300. In this case, the ejecting parts 370 may be disposed to be spaced apart from each other and connected to the base part 310.

The inner tube 330 may be disposed in the base part 310 and connected to an internal conduit of the printhead part 100, and may be supplied with the ink 90 from the ink circulation part 500. The inner tube 330 may be supplied with the ink 90 through the first connection tube IL1 connected to the ink circulation part 500, and the remaining ink 90 after the ink 90 is ejected from the nozzle 350 may be supplied to the ink reservoir part 500 through the second connection tube IL2. The base part 310 may have a shape extending in a direction, and the inner tube 330 may be formed in the direction in which the base part 310 extends. The ink 90 supplied through the printhead part 100 may flow through the inner tube 330 and be ejected through the nozzle 350 of the inkjet head 300.

The nozzles 350 may be disposed on a surface, for example, a lower surface of the base part 310, and disposed in the ejecting part 370. The nozzles 350 may be spaced apart from each other and arranged in the direction in which the base part 310 extends. The nozzles 350 may pass through the ejecting part 370 and be connected to the inner tube 330 to eject the ink 90. Although not shown in the drawings, the nozzles 350 may be arranged in a row or rows. In addition, although it is illustrated in the drawing that four nozzles 350 are formed in the inkjet head 300, the disclosure is not limited thereto. In some embodiments, the number of nozzles 350 included in the inkjet head 300 may be in a range of about 128 to about 1800. The nozzle 350 may eject the ink 90 introduced along the inner tube 330. The amount of ink 90 ejected through the nozzles 350 may be adjusted according to a voltage applied to each nozzle 350. In an embodiment, the amount of the ink 90 ejected at one time through each nozzle 350 may be in a range of about 1 pl to about 50 pl (where "pl" denotes picoliter), but is not limited thereto.

According to an embodiment, the nozzle 350 may include an inlet 351 and an outlet 353. The inlet 351 may be directly connected to the inner tube 330, and may be a portion through which the ink 90 flowing along the inner tube 330 is supplied to the nozzle 350. The outlet 353 may be connected to the inlet 351, and may be a portion through which the ink 90 supplied from the inlet 351 is ejected from the nozzle 350. The inlet 351 and the outlet 353 of the nozzle 350 may have a same diameter, but the disclosure is not limited thereto. In the nozzle 350, diameters of the inlet 351 and the outlet 353 may be different from each other depending on the shape of the ejecting part 370. The ejecting part 370 may include portions that are distinct from one another, and may have a different shape depending on the diameter of the nozzle 350.

The ink 90 ejected through the nozzle 350 may include the solvent 91 and the bipolar elements 95 dispersed in the solvent 91. According to an embodiment, the bipolar element 95 may have a shape extending in a direction. The bipolar elements 95 may be randomly dispersed in the ink 90, flow along the inner tube 330, and be supplied to the nozzle 350. As the bipolar element 95 has the shape extending in a direction, the bipolar element 95 may have an orientation direction that is a direction of its long axis. In addition, the bipolar element 95 may include a first end having a first polarity and a second end having a second polarity, and the first end and the second end may be opposite ends in the direction of the long axis of the bipolar element 95. The orientation of the bipolar element 95 extending in a direction may be defined based on the direction in which the first end is directed. The bipolar elements 95 flowing in the inner tube 330 and the nozzle 350 of the inkjet head 300 may not be oriented in a constant direction, and may be dispersed in random directions. However, the disclosure is not limited thereto, and the bipolar elements 95 may flow in the inner tube 330 and the nozzle 350 while being oriented in a specific direction.

The actuator 390 may be disposed on the ejecting part 370 of the base part 310. The actuator 390 may be disposed to surround the nozzle 350. The actuator 390 may apply hydraulic pressure to the ink 90 introduced into the nozzle 350 so that the ink 90 may be smoothly ejected through the nozzle 350. The actuator 390 and the ejecting part 370 may have substantially a same length, but the disclosure is not limited thereto. The actuator 390 may be disposed to surround the nozzle 350, corresponding to the nozzle 350, and may be spaced apart from other actuators 390 by a distance between the spaced-apart nozzles 350. However, the actuator 390 may be omitted.

The sensing part 400 may be disposed in the ejecting part 370 of the base part 310. The sensing part 400 may be provided inside the ejecting part 370 and be disposed corresponding to each nozzle 350. In some embodiments, the sensing parts 400 may be inserted into the ejecting part 370, and may be arranged in the first direction DR1 along the nozzles 350 arranged in the first direction DR1. In addition, the sensing parts 400 may be arranged in the second direction DR2 along the nozzles 350 arranged in the second direction DR2. The sensing parts 400 may be spaced apart from the neighboring sensing parts 400, and may be disposed corresponding to each nozzle 350.

According to an embodiment, the sensing part 400 may be disposed above the actuator 390 disposed on the ejecting part 370. The sensing part 400 may be disposed between the actuator 390 and the inner tube 330 and adjacent to the inlet 351 of the nozzle 350, and may measure the number of bipolar elements 95 in the ink 90 introduced into the nozzle 350 from the inner tube 330, as will be described below. The sensing part 400 may measure the number of bipolar elements 95 before the ink 90 is ejected through the actuator 390, thereby measuring the number of bipolar elements 95 in the ink 90 ejected from the nozzle 350. However, the disclosure is not limited thereto, and the sensing part 400 may be further disposed at another location along the path through which the ink 90 flows. For example, the sensing part 400 may also be disposed on the base part 310 in which the inner tube 330 of the inkjet head 300 is located, or disposed on the first connection tube IL1 that connects between the ink circulation part 500 and the inkjet head 300. This will be described with reference to other embodiments.

The sensing part 400 may include a light emitting part 410 and a light receiving part 420, which may be disposed to be spaced apart from each other with the nozzle 350 interposed therebetween. The light emitting part 410 of the sensing part 400 may be disposed on a side of the nozzle 350, and the light receiving part 420 may be disposed on another side of the nozzle 350. Although it is illustrated in the drawing that the light emitting part 410 and the light receiving part 420 are disposed in contact with the outer wall of the nozzle 350, the disclosure is not limited thereto, such that the light emitting part 410 and the light receiving part 420 may be spaced apart from the outer wall of the nozzle 350.

The light emitting part 410 may emit light in a specific wavelength range, and the light receiving part 420 may receive the light emitted from the light emitting part 410 and incident thereon. The light emitting part 410 may irradiate the light to the ink 90 flowing in the nozzle 350, and the light may be incident on the light receiving part 420, passing through the nozzle 350 and the ink 90 in the nozzle 350. The type of the light emitting part 410 is not particularly limited. In some embodiments, the light emitting part 410 may be an ultraviolet laser emission device or lamp capable of emitting ultraviolet light, or a light emission device or lamp capable of emitting visible light or white light. However, the embodiment is not limited thereto, and the light emitting part 410 is a device capable of emitting light to the ink 90 flowing in the nozzle 350 and various modification thereof may be made within a range that can be employed in the art.

In case that the ink 90 flows into the nozzle 350 while flowing through the inner tube 330, the light emitted from the light emitting part 410 may be incident on the bipolar element 95. According to an embodiment, the nozzle 350 may have an outer wall made of a transparent material so that the light emitted from the light emitting part 410 of the sensing part 400 can be emitted to the bipolar element 95 in the ink 90. The outer wall of the nozzle 350, and the base part 310 or the ejecting part 370 may be made of (or include) substantially a same material, but the disclosure is not limited thereto. The outer wall of the nozzle 350 may be positioned in contact with the light emitting part 410 and the light receiving part 420, and the light emitted from the light emitting part 410 passing through the ink 90 via the transparent outer wall may be incident on the light receiving part 420.

The light may be partially scattered by interference of the bipolar elements 95, and the light receiving part 420 may receive the light emitted from the light emitting part 410 and the scattered light and measure the number of bipolar elements 95 flowing in the nozzle 350.

Figure 7:
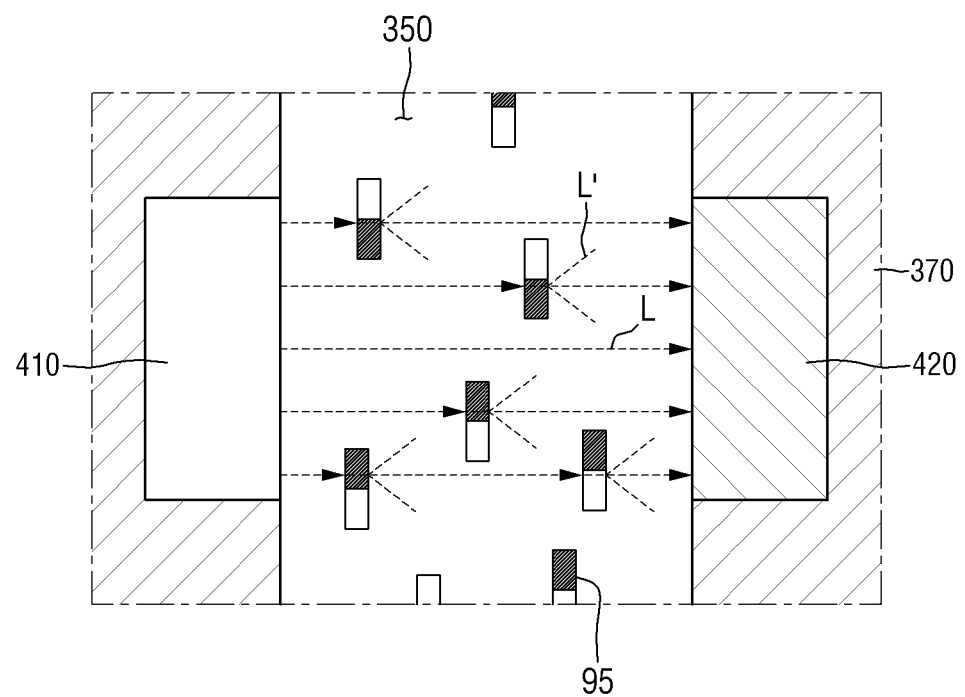
FIG. 7 is a schematic diagram illustrating portion Q2 of FIG. 6.

FIG. 7 is a schematic diagram illustrating portion Q2 of FIG. 6.

Referring to FIG. 7 in conjunction with FIG. 6, the light emitting part 410 of the sensing part 400 may emit light L (see FIG. 7) toward the light receiving part 420 disposed on an opposite side with respect to the nozzle 350. While the light L is incident on the light receiving part 420 through the nozzle 350, at least part of the light L may be irradiated to the bipolar elements 95 flowing in the nozzle 350. In case that the light L is irradiated to the bipolar elements 95 dispersed in the ink 90, part of the light L may be scattered (see light L' of FIG. 7), and in addition to the light L emitted from the light emitting part 410, the light L' scattered by the bipolar element 95 may be incident on the light receiving part 420. The light L' scattered by the bipolar element 95 may have a specific waveform according to a Brownian motion of the bipolar element 95. The light receiving part 420 may measure the size of the bipolar element 95 by analyzing the waveform of the light L' scattered by the bipolar element 95, and thereby measure the number of bipolar elements 95 flowing in a unit space within the nozzle 350. The sensing part 400 may measure the number or the degree of dispersion of bipolar elements 95 in the ejected ink 90 based on the measured number of bipolar elements 95 and the volume of ink droplets of the ink 90 ejected through the nozzle 350.

According to an embodiment, as soon as the inkjet printing device 1000 ejects the ink 90, the sensing part 400 may measure the number of bipolar elements 95 in the ejected ink 90 and detect a change in the degree of dispersion and the number of bipolar elements 95 per unit droplet of the ink 90 during the printing process. In addition, in case that the change in the number of bipolar elements 95 exceeds a reference set value, the inkjet printing device 1000 feeds back the result in real time, so that the number of bipolar elements 95 introduced into the nozzle 350 or the inkjet head, the degree of dispersion of the bipolar elements 95 in the ink 90 introduced into the inkjet head 300 may be controlled. Through this process, a uniform number of bipolar elements 95 in the ink 90 ejected from the inkjet head 300 may be maintained.

Figure 8:
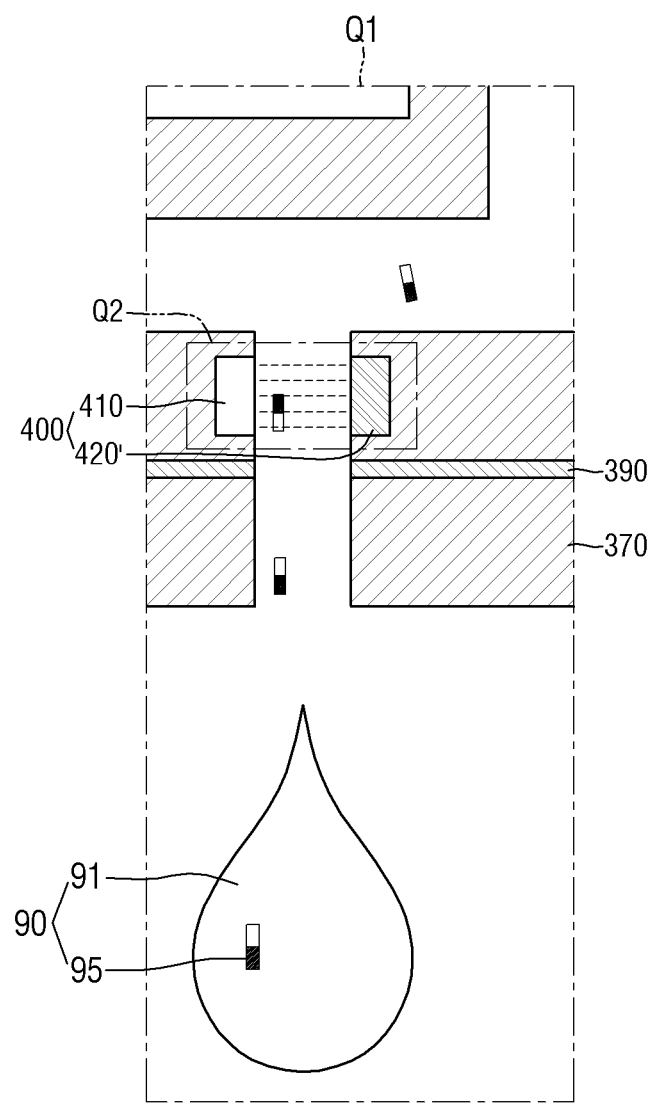
FIGS. 8 and 9 are schematic diagrams illustrating examples in which the number of bipolar elements flowing in an inkjet head varies.
Figure 9:
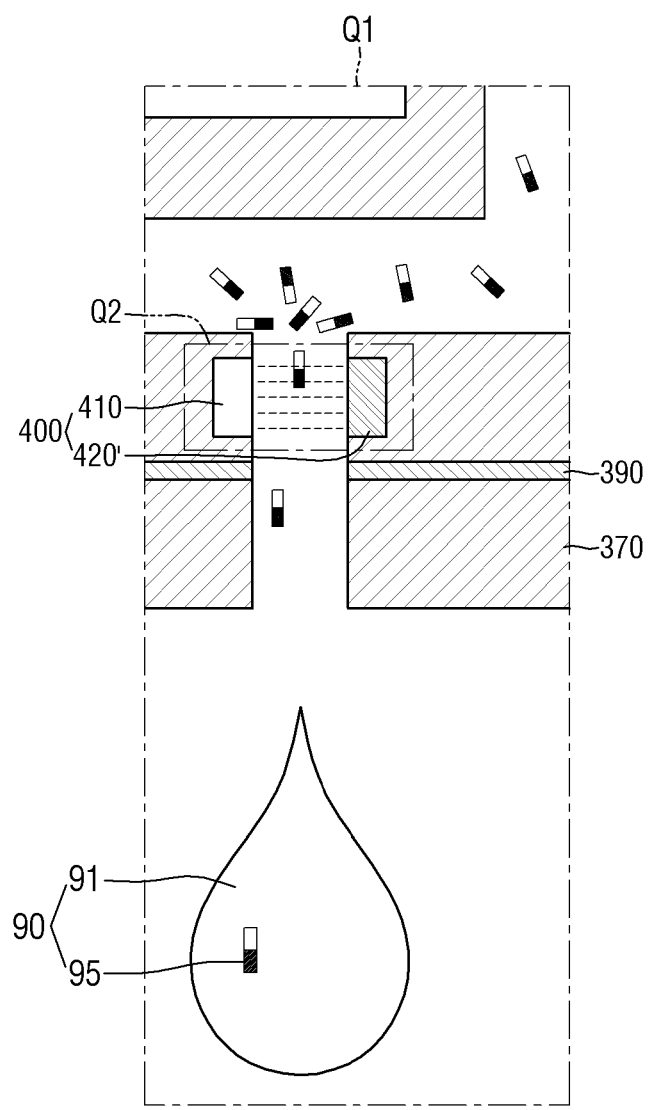

FIGS. 8 and 9 are schematic diagrams illustrating examples in which the number of bipolar elements flowing in an inkjet head varies.

Referring to FIG. 8, in case that the number of bipolar elements 95 in the ink 90 introduced into the inkjet head 300 decreases, the number of bipolar elements 95 ejected through the nozzle 350 may also decrease. For example, in case that the stirrer ST of the third ink reservoir 530 in the ink circulation part 500 does not operate smoothly and the bipolar elements 95 settle, the number of bipolar elements 95 in the ink 90 introduced into the inkjet head 300 may be reduced. Only a few bipolar elements 95 are introduced into the inner tube 330 and the nozzle 350 of the inkjet head 300, and the number of bipolar elements 95 ejected through the nozzle 350 may also be reduced.

As another example, referring to FIG. 9, as the bipolar elements 95 have a shape extending in a direction, the bipolar elements 95 are agglomerated at the inlet 351 of the nozzle 350, and thus the number of bipolar elements 95 introduced into the nozzle 350 may be reduced. In this case, the number of bipolar elements 95 introduced into the inner tube 330 does not change, but the number of bipolar elements 95 ejected through the nozzle 350 may decrease.

As described above, the light receiving part 420 may analyze the waveform of the light L' scattered by the bipolar element 95 to measure the size of the bipolar element 95, and thereby measure the number of bipolar elements 95 flowing in the unit space within the nozzle 350. As shown in FIGS. 8 and 9, in case that the number of bipolar elements 95 ejected through the nozzle 350 or the number of bipolar elements 95 introduced into the nozzle 350 decreases, the amount or the waveform of the light incident on a light receiving part 420' of the sensing part 400 may vary. The sensing part 400 may detect a change in the number of bipolar elements 95 flowing in the nozzle 350 based on a change in light incident on the light receiving part 420'.

The inkjet printing device 1000 may include the sensing part 400 disposed on the inkjet head 300 to measure the number of bipolar elements 95 ejected through at least the nozzle 350 and detect a change in the number of bipolar elements 95. In the inkjet printing device 1000, the ink circulation part 500 or the inkjet head 300 may receive the change detected by the sensing part 400 and control the number of bipolar elements 95 ejected through the nozzle 350. As in the case of FIG. 8, in case that the number of bipolar elements 95 introduced into the inkjet head 300 is reduced, the variation may be fed back to the ink circulation part 500, and as in the case of FIG. 9, in case that the number of bipolar elements 95 introduced into the nozzle 350 is reduced, the variation may be fed back to the inkjet head 300. However, the disclosure is not limited thereto, and there may be various causes for the change in the number of the bipolar elements 95. In some embodiments, the inkjet printing device 1000 may include a greater number of sensing parts 400 to provide accurate feedback with respect to a change in the number of bipolar elements 95. The inkjet printing device 1000 may maintain a uniform number of bipolar elements 95 in the ink 90 ejected from the inkjet head 300 through the feedback provided from the sensing part 400.

Figure 10:
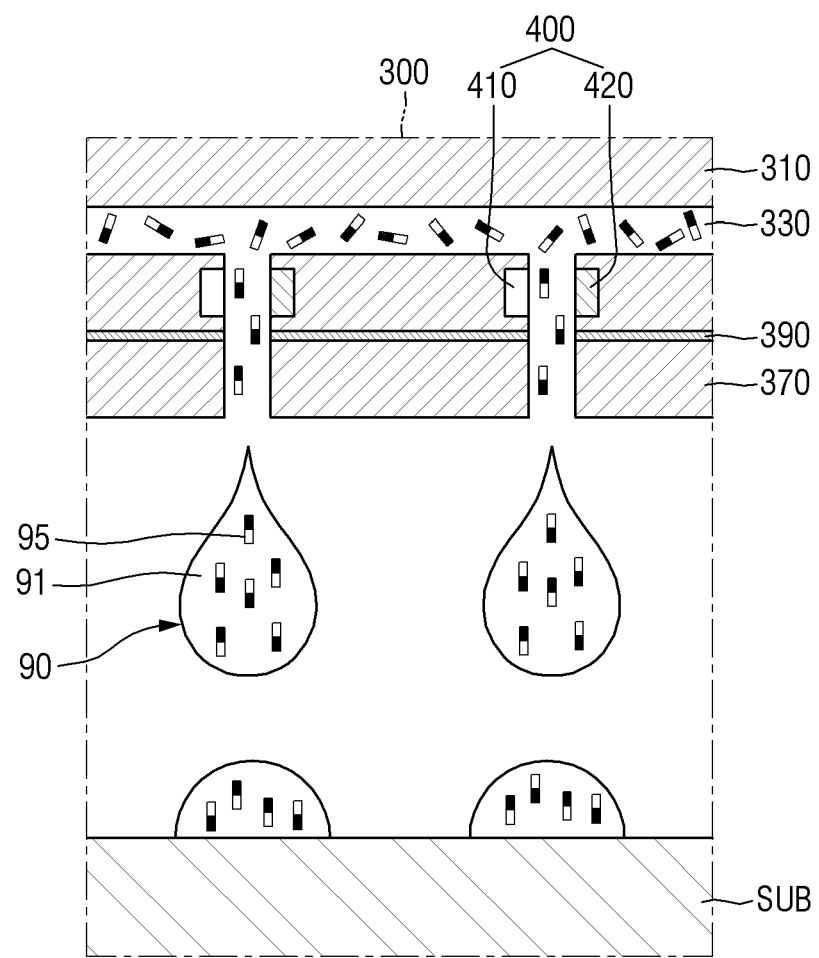
FIG. 10 is a schematic diagram illustrating ink ejected from an inkjet head according to an embodiment.

FIG. 10 is a schematic diagram illustrating ink ejected from an inkjet head according to an embodiment.

Referring to FIG. 10, the ink 90 ejected from the inkjet head 300 may be sprayed onto the target substrate SUB. The number of bipolar elements 95 in the ink 90 measured by the sensing part 400 may correspond to the number of bipolar elements 95 in the ink 90 sprayed onto the target substrate SUB. The inkjet printing device 1000 according to an embodiment may include a sensing part 400 to detect a change in the number of bipolar elements 95 to maintain a uniform number of bipolar elements 95 in the ejected ink 90, and the ink 90 containing a uniform number of bipolar elements 95 per unit area may be sprayed onto the target substrate SUB. For example, the inkjet printing device 1000 may print or eject a uniform number of bipolar elements 95 within an area. As will be described below, the inkjet printing device 1000 may minimize an error in the number of bipolar elements 95 for each area of the device including the bipolar elements 95 and improve product reliability.

After the bipolar elements 95 oriented in a specific direction are sprayed onto the target substrate SUB, they may be mounted on the target substrate SUB while being oriented in a direction by an electric field generated by the probe device 700. For example, the bipolar elements 95 may be aligned in a direction on the target substrate SUB by the electric field generated by the probe device 700. Hereinafter, the probe device 700 will be described with reference to other drawings.

Figure 11:
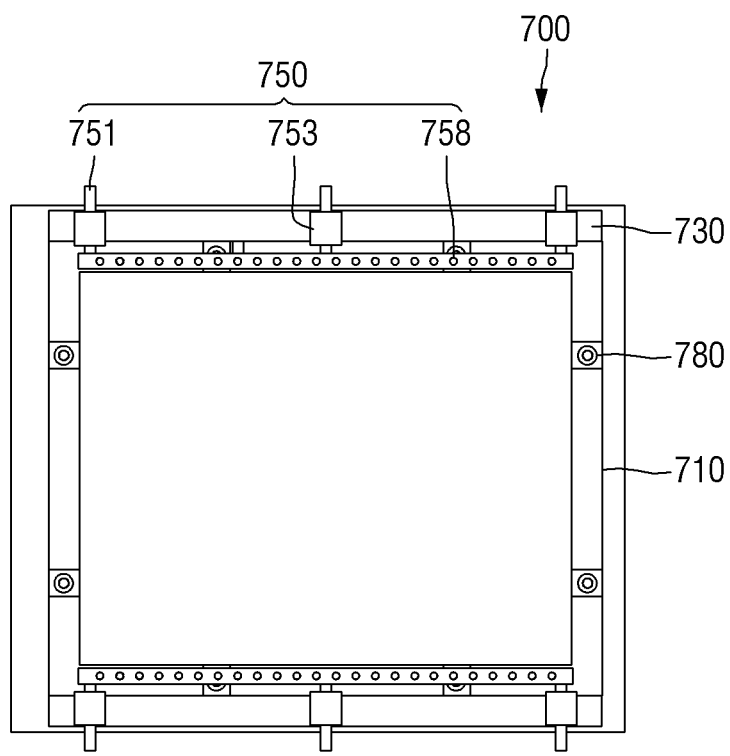
FIG. 11 is a schematic plan view of a probe device according to an embodiment.
Figure 11:
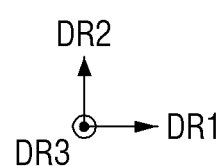

FIG. 11 is a schematic plan view of a probe device according to an embodiment.

Referring to FIGS. 1 and 11, the probe device 700 may include a sub-stage 710, a probe support 730, a probe part 750, and an aligner 780.

The probe device 700 may be disposed on the stage STA, and may move in the second direction DR2 together with the stage STA. The probe device 700 on which the target substrate SUB is disposed may move along the stage STA, and the ink 90 may be sprayed thereon. In case that the ink 90 is sprayed, the probe device 700 may generate an electric field on the target substrate SUB. However, the disclosure is not limited thereto. In some embodiments, the stage STA may not move, but the printhead part 100 may move in the second direction DR2 to spray the ink 90 onto the stage STA.

The sub-stage 710 may provide a space on which the target substrate SUB is disposed. In addition, the probe support 730, the probe part 750, and the aligner 780 may be disposed on the sub-stage 710. The shape of the sub-stage 710 is not particularly limited, but as an example, the sub-stage 710 may have a quadrilateral shape with sides extending in the first direction DR1 and the second direction DR2 as shown in the drawing. The sub-stage 710 may include long sides extending in the first direction DR1 and short sides extending in the second direction DR2. However, the overall planar shape of the sub-stage 710 may vary depending on the shape of the target substrate SUB in a plan view. For example, in case that the target substrate SUB is rectangular in a plan view, the shape of the sub-stage 710 may be rectangular as shown in the drawing, and in case that the target substrate SUB has a circular plane, the sub-stage 710 may also have a circular shape in a plan view.

At least one aligner 780 may be disposed on the sub-stage 710. The aligner 780 is disposed on each side of the sub-stage 710, and an area surrounded by aligners 780 may be an area in which the target substrate SUB is disposed. In the drawing, it is shown that two aligners 780 are disposed to be spaced apart from each other on each side of the sub-stage 710, and a total of eight aligners 780 are disposed on the sub-stage 710. However, the disclosure is not limited thereto, and the number and arrangement of the aligners 780 may vary depending on the shape or type of the target substrate SUB.

The probe support 730 and the probe part 750 are disposed on the sub-stage 710. The probe support 730 may provide a space in which the probe part 750 is disposed on the sub-stage 710. Specifically, the probe support 730 may be disposed on at least one side of the sub-stage 710 and may extend in a direction in which a side portion extends. For example, as shown in the drawing, the probe supports 730 may be disposed on left and right sides of the sub-stage 710 to extend in the second direction DR2. However, the disclosure is not limited thereto, and a greater number of probe supports 730 may be included, and in some embodiments, the probe supports 730 may also be disposed on upper and lower sides of the sub-stage 710. For example, the structure of the probe support 730 may vary depending on the number of probe parts 750 included in the probe device 700, or the arrangement or structure of the probe parts 750.

The probe part 750 may be disposed on the probe support 730 to form an electric field on the target substrate SUB prepared in the sub-stage 710. As in the probe support 730, the probe part 750 may extend in a direction, for example, the second direction DR2, and an extended length may cover the entire target substrate SUB. For example, the size and shape of each of the probe support 730 and the probe part 750 may vary depending on the target substrate SUB.

In an embodiment, the probe part 750 may include a probe driving part 753 disposed on the probe support 730, a probe jig 751 disposed on the probe driving part 753 and configured to receive an electrical signal transmitted thereto, and a probe pad 758 connected to the probe jig 751 to transmit the electrical signal to the target substrate SUB.

The probe driving part 753 may be disposed on the probe support 730 to move the probe jig 751 and the probe pad 758. In an embodiment, the probe driving part 753 may move the probe jig 751 in a horizontal direction and a vertical direction, for example, in the first direction DR1 that is the horizontal direction, and the third direction DR3 that is the vertical direction. The probe pad 758 may be connected to or separated from the target substrate SUB by the operation of the probe driving part 753. During a process of the inkjet printing device 1000, the probe driving part 753 is driven to connect the probe pad 758 to the target substrate SUB in the operation of forming an electric field on the target substrate SUB, and the probe driving part 753 is driven again to separate the probe pad 758 from the target substrate SUB in the other operations. This will be described in detail below with reference to other drawings.

The probe pad 758 may form an electric field on the target substrate SUB by using an electrical signal transmitted from the probe jig 751. The probe pad 758 may be connected to the target substrate SUB to transmit the electrical signal thereto to form the electric field on the target substrate SUB. For example, the probe pad 758 may contact an electrode, a power pad, or the like of the target substrate SUB, and the electrical signal from the probe jig 751 may be transmitted to the electrode or the power pad. The electrical signal transmitted to the target substrate SUB may form an electric field on the target substrate SUB.

However, the disclosure is not limited thereto, and the probe pad 758 may be a member that forms an electric field by using an electrical signal transmitted from the probe jig 751. For example, in case that the electric field is formed by receiving the electrical signal from the probe pad 758, the probe pad 758 may not be extended to the target substrate SUB.

The shape of the probe pad 758 is not particularly limited, but in an embodiment, the probe pad 758 may have a shape extending in a direction to cover the entire target substrate SUB.

The probe jig 751 may be extended to the probe pad 758 and may be extended to a separate voltage applying device. The probe jig 751 may transmit an electrical signal transmitted from the voltage applying device to the probe pad 758 to form the electric field on the target substrate SUB. The electrical signal transmitted to the probe jig 751 may be a voltage for forming an electric field, for example, an AC voltage.

The probe part 750 may include probe jigs 751, and the number of probe jigs 751 is not particularly limited. FIG. 11 illustrates that three probe jigs 751 and three probe driving parts 753 are disposed, but the probe part 750 may include a greater number of probe jigs 751 and probe driving parts 753 to form an electric field having a higher density on the target substrate SUB.

The probe part 750 according to an embodiment is not limited thereto. It is illustrated in the drawing that the probe part 750 is disposed on the probe support 730, for example, the probe device 700, but in some embodiments, the probe part 750 may also be disposed as a separate device. The structure or arrangement of the probe device 700 is not limited as long as an electric field can be formed on the target substrate SUB by including a device capable of forming the electric field.

Figure 12:
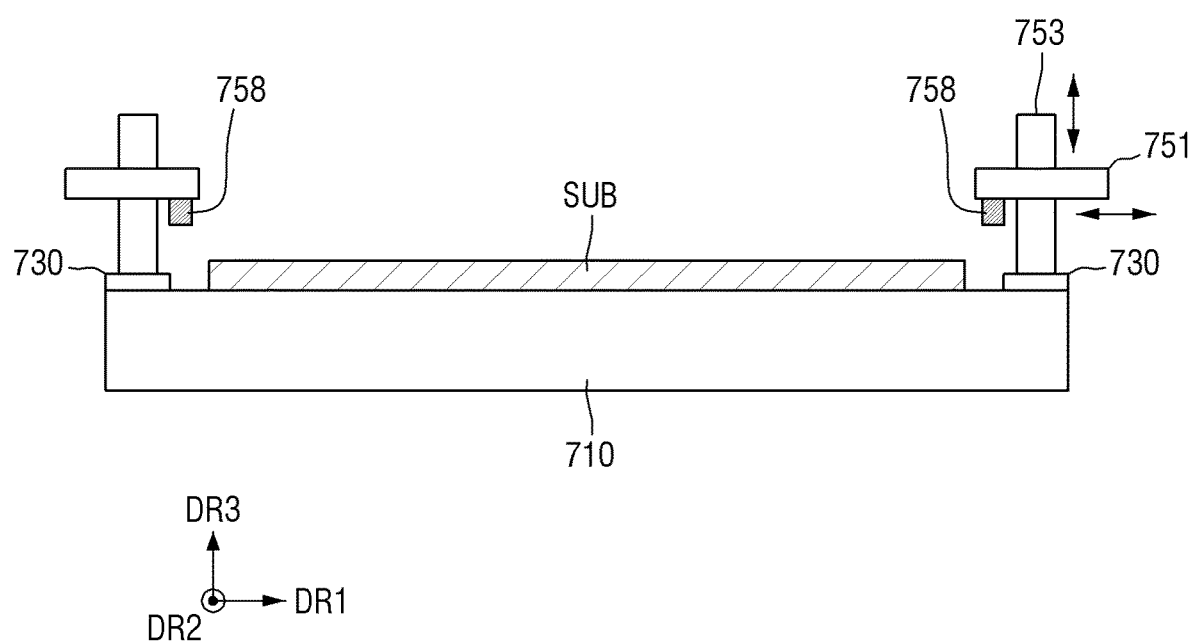
FIGS. 12 and 13 are schematic diagrams illustrating an operation of a probe part according to an embodiment.
Figure 13:
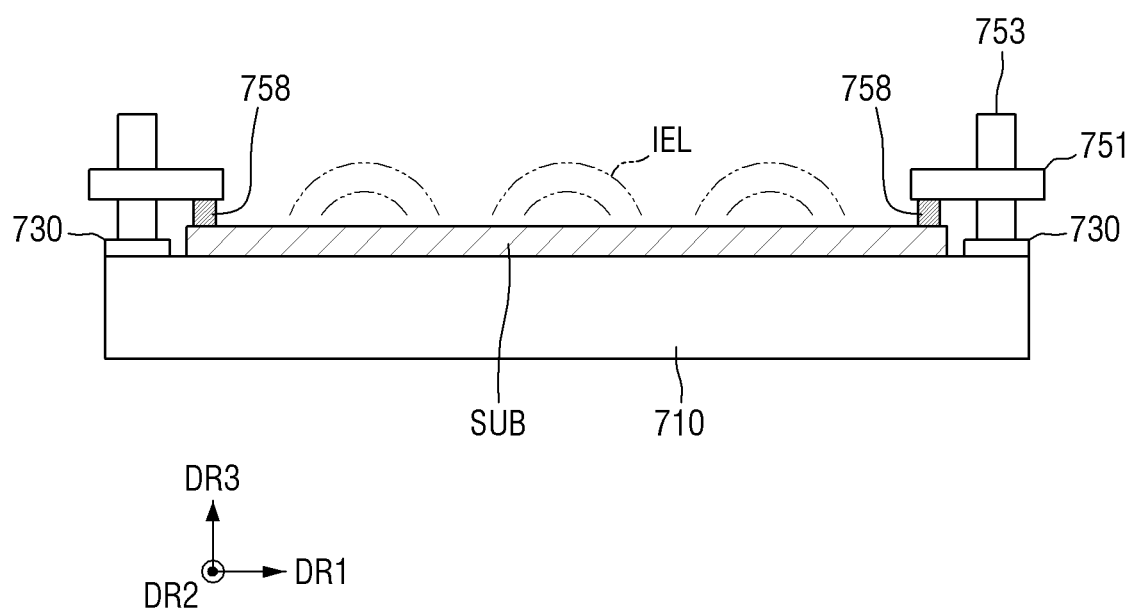

FIGS. 12 and 13 are schematic diagrams illustrating an operation of a probe part according to an embodiment.

As described above, the probe driving part 753 of the probe part 750 may operate according to the process operation of the inkjet printing device 1000. Referring to FIGS. 12 and 13, in a first state in which an electric field IEL is not formed in the probe device 700, the probe part 750 may be disposed on the probe support 730 to be spaced apart from the target substrate SUB. The probe driving part 753 of the probe part 750 is driven in the second direction DR1, which is a horizontal direction, and the third direction DR3, which is a vertical direction, to separate the probe pad 758 from the target substrate SUB.

In a second state in which the electric field IEL is formed on the target substrate SUB, the probe driving part 753 of the probe part 750 may be driven to connect the probe pad 758 to the target substrate SUB. The probe pad 758 may contact the target substrate SUB by driving the probe driving part 753 in the third direction DR3, which is a vertical direction, and the first direction DR1, which is a horizontal direction. The probe jig 751 of the probe part 750 may transmit an electrical signal to the probe pad 758, and the electric field IEL may be formed on the target substrate SUB.

Meanwhile, it is illustrated in the drawing that a probe part 750 is disposed on each of sides of the probe device 700 and two probe parts 750 are simultaneously connected to the target substrate SUB. However, the disclosure is not limited thereto, and the probe parts 750 may be separately driven. For example, in case that the target substrate SUB is prepared on the sub-stage 710 and the ink 90 is sprayed onto the target substrate SUB, first, an arbitrary first probe part 750 may form an electric field IEL on the target substrate SUB, and a second probe part 750 may not be connected to the target substrate SUB. Thereafter, the first probe part 750 may be separated from the target substrate SUB and the second probe part 750 may be connected to the target substrate SUB to form an electric field IEL. For example, the probe parts 750 may be simultaneously driven to form an electric field, or may be sequentially driven to form an electric field.

Figure 14:
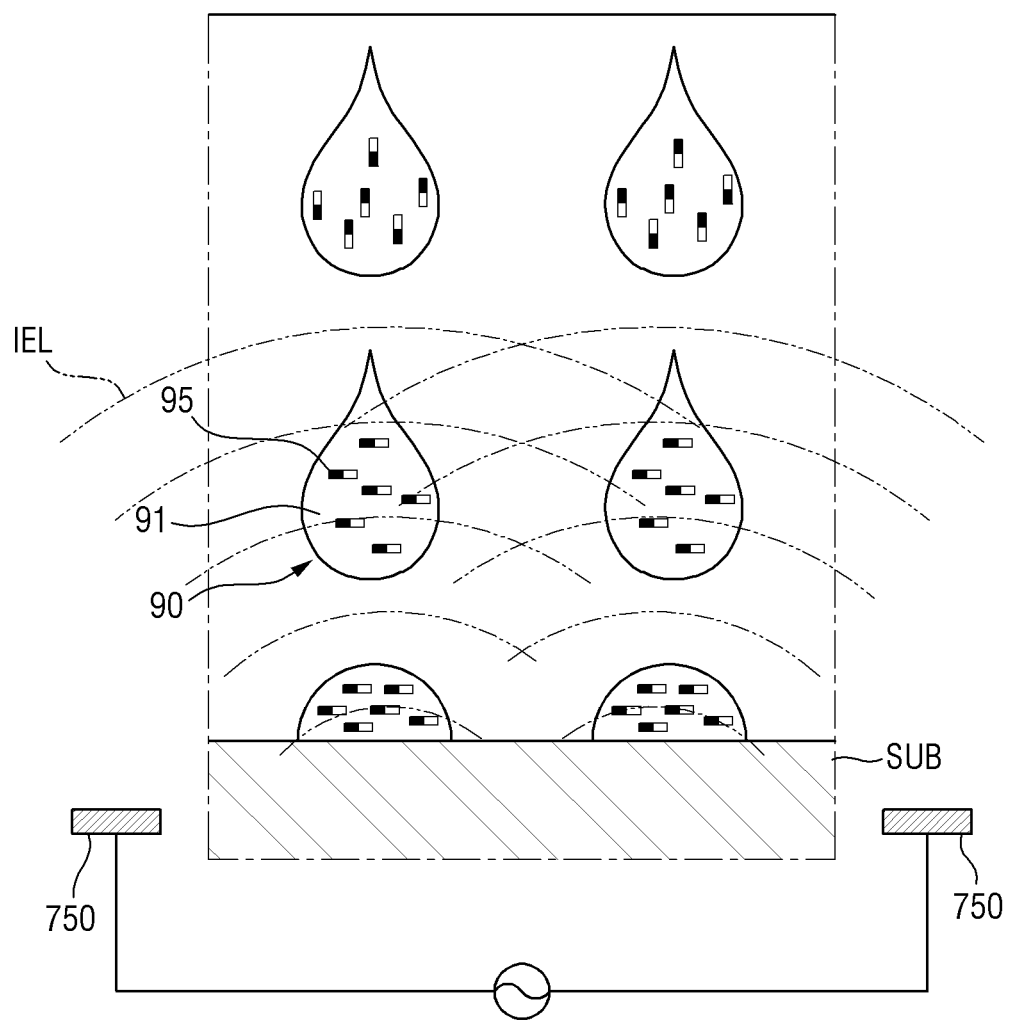
FIG. 14 is a schematic diagram illustrating an electric field generated on a target substrate by a probe device according to an embodiment.

FIG. 14 is a schematic diagram illustrating an electric field generated on a target substrate by a probe device according to an embodiment.

Referring to FIG. 14, as described above, the bipolar element 95 may include a first end and a second end each of which has a polarity, and may be subjected to a dielectrophoretic force, when placed in an electric field, so that a position or orientation direction may change. Bipolar elements 95 in the ink 90 sprayed onto the target substrate SUB may be mounted on the target substrate SUB while positions and orientation directions thereof are changed by an electric field IEL generated by the probe device 700.

The probe device 700 may generate the electric field IEL on the target substrate SUB, and the ink 90 ejected through the nozzle 350 of the inkjet head 300 may be sprayed onto the target substrate SUB, passing through the electric field IEL. The bipolar elements 95 may be subjected to a dielectrophoretic force due to the electric field IEL until the ink 90 reaches the target substrate SUB, or even after the ink 90 reaches the target substrate SUB. According to an embodiment, after the bipolar element 95 is ejected from the inkjet head 300, the orientation direction and position of the bipolar element 95 may be changed by the electric field IEL generated by the probe device 700.

The electric field IEL generated by the probe device 700 may be formed in a direction parallel to the upper surface of the target substrate SUB. The bipolar element 95 sprayed onto the target substrate SUB may be oriented by the electric field IEL such that a direction in which the long axis extends is directed in a direction parallel to the upper surface of the target substrate SUB. In addition, the first ends of the bipolar elements 95 having a polarity may be oriented in a specific direction and the bipolar elements 95 may be mounted on the target substrate SUB.

In case that the bipolar elements 95 are mounted on the target substrate SUB, an alignment degree may be measured by taking into consideration a deviation in the orientation directions of the bipolar elements 95, or a deviation in the mounted positions on the target substrate SUB. Based on a bipolar element 95 among the bipolar elements 95 mounted on the target substrate SUB, the deviations in the orientation direction and the mounted position of the other bipolar elements 95 may be measured, and by using the deviations, the alignment degree of the bipolar elements 95 may be measured. The "alignment degree" of the bipolar elements 95 may refer to the deviations in the orientation direction and mounted position of the bipolar elements 95 aligned on the target substrate SUB. For example, in case that the deviation in the orientation direction and mounted position of the bipolar elements 95 is great, it may be understood that the alignment degree of the bipolar elements 95 is low, and in case that the deviation in the orientation direction and mounted position of the bipolar elements 95 is small, it may be understood that the alignment degree of the bipolar elements 95 is high or is improved.

The timing when the probe device 700 generates the electric field IEL on the target substrate SUB is not particularly limited. It is illustrated in the drawing that the probe part 750 generates the electric field IEL while the ink 90 is ejected through the nozzle 350 and reaches the target substrate SUB. Accordingly, the bipolar elements 95 ejected through the nozzle 350 may be subjected to a dielectrophoretic force by the electric field IEL until they reach the target substrate SUB. However, the disclosure is not limited thereto, and in some embodiments, the probe part 750 may generate an electric field IEL after the ink 90 is mounted on the target substrate SUB. For example, the probe device 700 may generate the electric field IEL in case that the ink 90 is sprayed from the inkjet head 300, or thereafter.

Although not illustrated in the drawing, in some embodiments, an electric field generating member may be further disposed on the sub-stage 710. As in the probe part 750, which will be described in more detail below, the electric field generating member may generate an electric field in an upper portion (for example, the third direction DR3), or on the target substrate SUB. In an embodiment, the electric field generating member may an antenna part, a device including electrodes, or the like.

Although not shown in the drawings, the inkjet printing device 1000 according to an embodiment may further include a heat treatment part in which a process of volatilizing the ink 90 sprayed onto the target substrate SUB is performed. The heat treatment part may emit heat to the ink 90 sprayed on the target substrate SUB, so that the solvent 91 of the ink 90 is volatilized and removed, and the bipolar element 95 may be disposed on the target substrate SUB. The process of removing the solvent 91 by irradiating the ink 90 with heat may be performed using a suitable heat treatment part. A detailed description thereof will be omitted.

Hereinafter, a printing method of a bipolar element 95 by using the inkjet printing device 1000 according to an embodiment will be described in detail.

Figure 15:
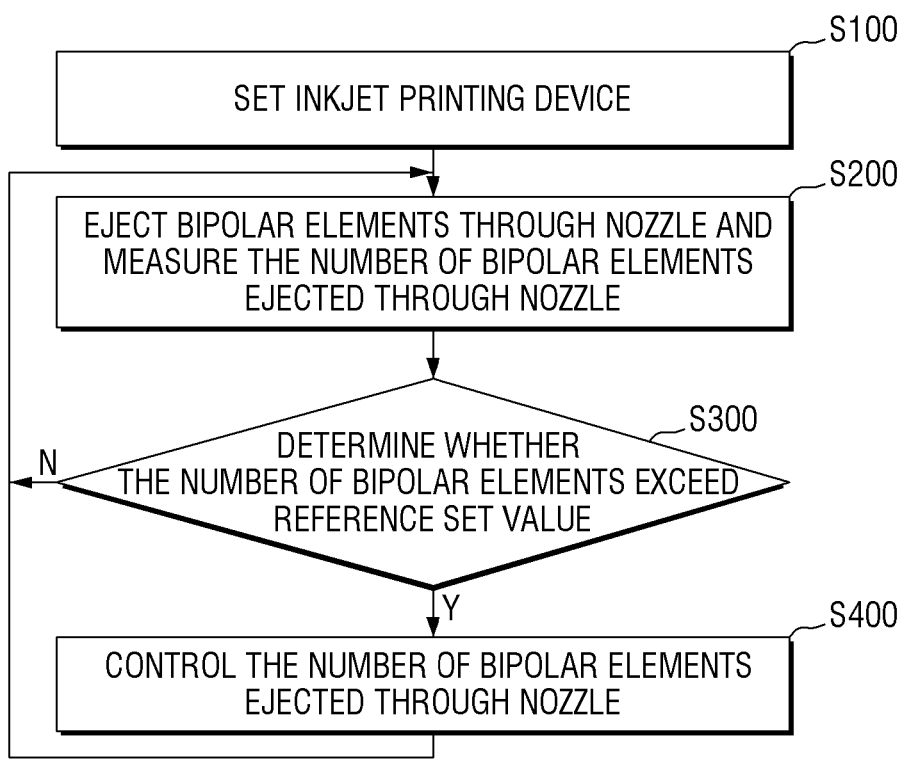
FIG. 15 is a schematic flowchart illustrating a printing method of a bipolar element according to an embodiment.

FIG. 15 is a schematic flowchart illustrating a printing method of a bipolar element according to an embodiment. FIGS. 16 to 21 are schematic cross-sectional views illustrating a method of printing a bipolar element by using an inkjet printing device according to an embodiment.

Referring to FIGS. 1 and 15 to 21, a method of aligning the bipolar elements 95 according to an embodiment may include setting the inkjet printing device 1000 (operation S100), ejecting the bipolar elements 95 through the nozzle 350 and measuring the number of bipolar elements 95 ejected through the nozzle 350 (operation S200), determining whether the number of bipolar elements 95 exceeds a reference set value (operation S300), and controlling the number of bipolar elements 95 flowing through the nozzle 350 based on the determination (operation S400).

A printing method of a bipolar element 95 according to an embodiment may be performed using the inkjet printing device 1000 described above with reference to FIG. 1, and the bipolar elements 95 may be ejected while the number of bipolar elements 95 per unit droplet in the ink 90 ejected from the inkjet head 300 is measured. In this specification, "printing" of the bipolar elements 95 may mean that the bipolar elements 95 are ejected or sprayed on an object by using the inkjet printing device 1000. For example, printing of the bipolar elements 95 may mean that the bipolar elements 95 may be ejected directly through the nozzle 350 of the inkjet head 300 or may be ejected in a state in which the bipolar elements 95 are dispersed in the ink 90. The printing of the bipolar elements 95 is not limited thereto, and the printing of the bipolar elements 95 may mean that the bipolar elements 95 or the ink 90 in which the bipolar elements 95 are dispersed are sprayed onto the target substrate SUB (see FIG. 10) so that the bipolar elements 95 or the ink 90 are mounted on the target substrate SUB.

The printing method of a bipolar element 95 by using the inkjet printing device 1000 may include measuring the number of bipolar elements 95 flowing in the inkjet head 300 and determining whether the number of bipolar elements exceeds a reference set value. Based on the determination, a change in the number of bipolar elements 95 ejected through the nozzle 350 may be detected, and this may be fed back to the ink circulation part 500 or the inkjet head 300. In case that it is necessary to control the number of bipolar elements 95, after feedback to the ink circulation part 500 and the inkjet head 300, printing of the bipolar elements 95 may be continued.

First, the inkjet printing device 1000 is set (operation S100). The setting of the inkjet printing device 1000 (operation S100) is an operation of tuning the inkjet printing device 1000 according to a target process. For precise tuning, an inkjet printing test process may be performed on a substrate for inspection, and setting values of the inkjet printing device 1000 may be adjusted according to the result of the process.

Specifically, a substrate for inspection may be prepared first. The substrate for inspection and a target substrate SUB may have a same structure, but a bare substrate such as a glass substrate may also be used.

An upper surface of the substrate for inspection may be treated with a water repellent. The water-repellent treatment may be performed by fluorine coating or plasma surface treatment.

An ink 90 containing bipolar elements 95 may be applied to an upper surface of the substrate for inspection by using the inkjet printing device 1000, and the volume of droplets for each inkjet head 300 may be measured. The volume of droplets for each inkjet head 300 may be measured by checking sizes of droplets at the time of spraying and sizes of the droplets applied to the substrate by using a camera. In case that the measured volume of droplets is different from a reference volume of droplets, a voltage for each corresponding inkjet head 300 may be adjusted so that the reference volume of droplets can be ejected. This inspection method may be repeated a number of times until each inkjet head 300 eject a correct volume of droplets.

Here, according to an embodiment, the setting of the inkjet printing device 1000 may include measuring the number of bipolar elements 95 in a droplet sprayed onto the substrate for inspection. The number of bipolar elements 95 included in the reference volume of droplets sprayed onto the substrate for inspection may refer to a reference set value of the number of bipolar elements 95 per unit droplet of the ink 90 in the inkjet printing device 1000. Based on the reference set value set in the inkjet printing device 1000, a change in the number of bipolar elements 95 is detected and the number of bipolar elements 95 flowing in the nozzle 350 or ejected through the nozzle 350 may be controlled.

In addition, in the operation of setting the inkjet printing device 1000, in case that the setting of the reference set value is completed, the ink 90 in which the bipolar elements 95 are dispersed is prepared in the ink circulation part 500, and the ink 90 may be supplied to the inkjet head 300. The ink circulation part 500 and the inkjet head 300 may be maintained by the ink circulation system so that the bipolar elements 95 in the ink 90 have uniform dispersion.

However, the disclosure is not limited thereto, and the above-described operation (S100) of setting the inkjet printing device may be omitted.

Figure 16:
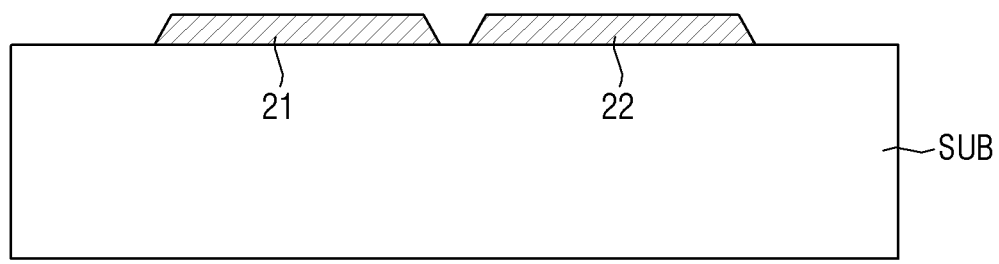
FIGS. 16 to 21 are schematic cross-sectional views illustrating a printing method of a bipolar element using an inkjet printing device according to an embodiment.
Figure 16:
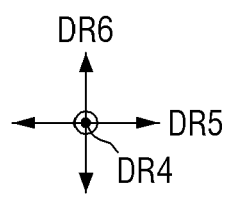

In case that the setting of the inkjet printing device 1000 is completed, as shown in FIG. 16, a target substrate SUB is prepared. In an embodiment, a first electrode 21 and a second electrode 22 may be disposed on the target substrate SUB. Although it is illustrated in the drawing that a pair of electrodes is disposed, a greater number of electrode pairs may be formed on the target substrate SUB, and inkjet heads 300 may spray the ink 90 on each electrode pair in a same manner.

Figure 17:
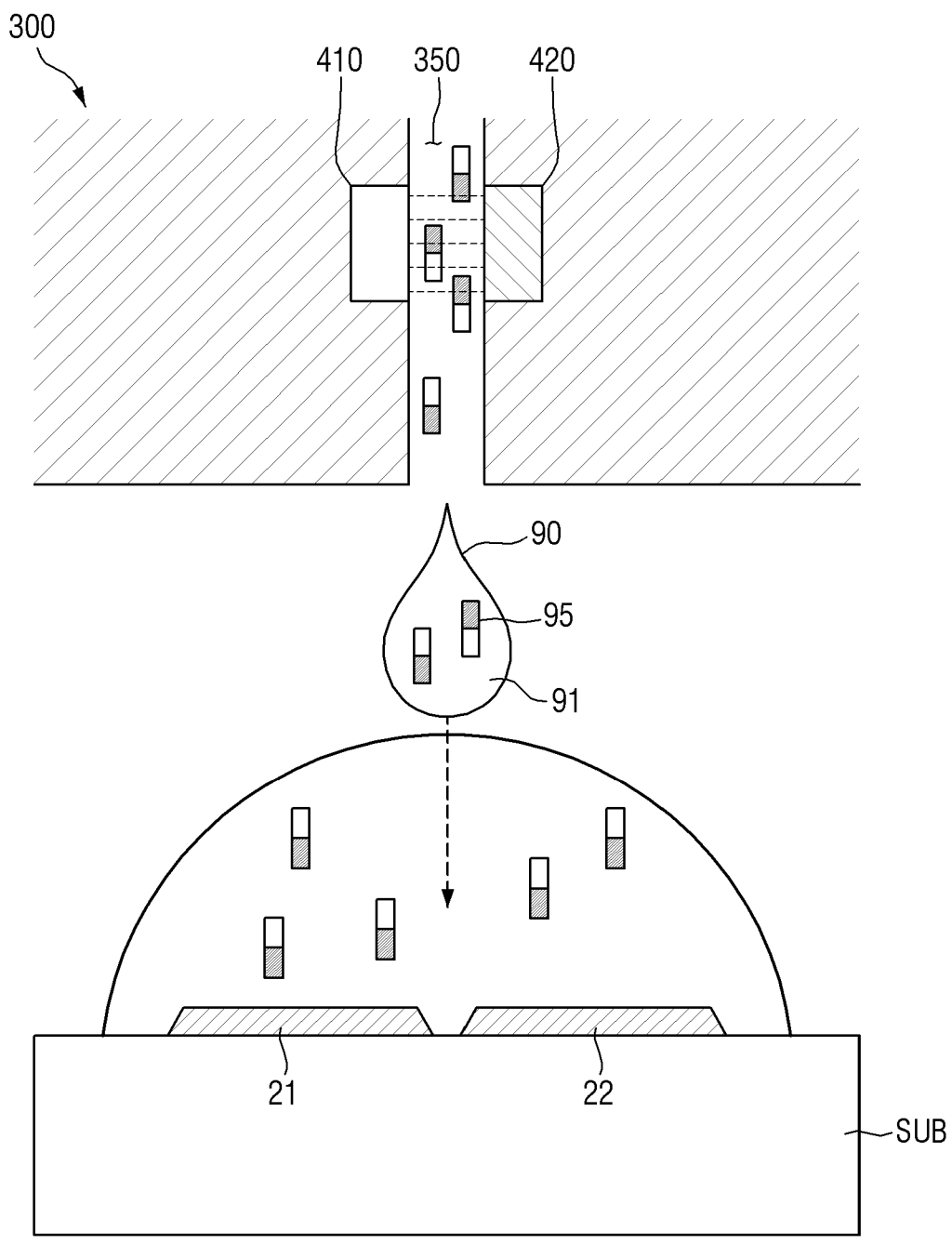

Thereafter, as shown in FIG. 17, the ink 90 containing the solvent 91 in which the bipolar elements 95 are dispersed is sprayed onto the target substrate SUB. The ink 90 may be ejected from the inkjet head 300 and may be sprayed onto the first electrode 21 and the second electrode 22 that are disposed on the target substrate SUB. The ink 90 may be sprayed onto the first electrode 21 and the second electrode 22 that are disposed on the target substrate SUB, and the bipolar elements 95 dispersed in the ink 90 may be sprayed onto the target substrate SUB while being extended in a direction. In some embodiments, the bipolar elements 95 dispersed in the ink 90 may be oriented in a direction perpendicular to the upper surface of the target substrate SUB. Further, in some embodiments, each of the bipolar elements 95 may be sprayed in a state in which a first end having a first polarity or a second end having a second polarity is aligned to have a same direction. However, the disclosure is not limited thereto.

The inkjet printing device 1000 according to an embodiment may include a sensing part 400 to eject or spray the ink 90 through the nozzle 350 and to measure the number of bipolar elements 95 ejected through the nozzle 350. The sensing part 400 may measure the number of bipolar elements 95 introduced into at least the nozzle 350 and thus measure the number of bipolar elements 95 per unit droplet of the ink 90 ejected through the nozzle 350. However, the disclosure is not limited thereto, and in some embodiments, in order to measure the number of bipolar elements 95 flowing in the inkjet head 300, the number of bipolar elements 95 flowing in the inner tube 330 and the number of bipolar elements 95 introduced into the inner tube 330, in addition to the number of bipolar elements 95 introduced into the nozzle 350, may be measured. Information on the measured number of bipolar elements 95 may be collected by each sensing part 400 and may be utilized to measure the number of bipolar elements 95 per unit droplet of the ink 90 ejected through the nozzle 350. This will be described with reference to other embodiments.

Figure 18:
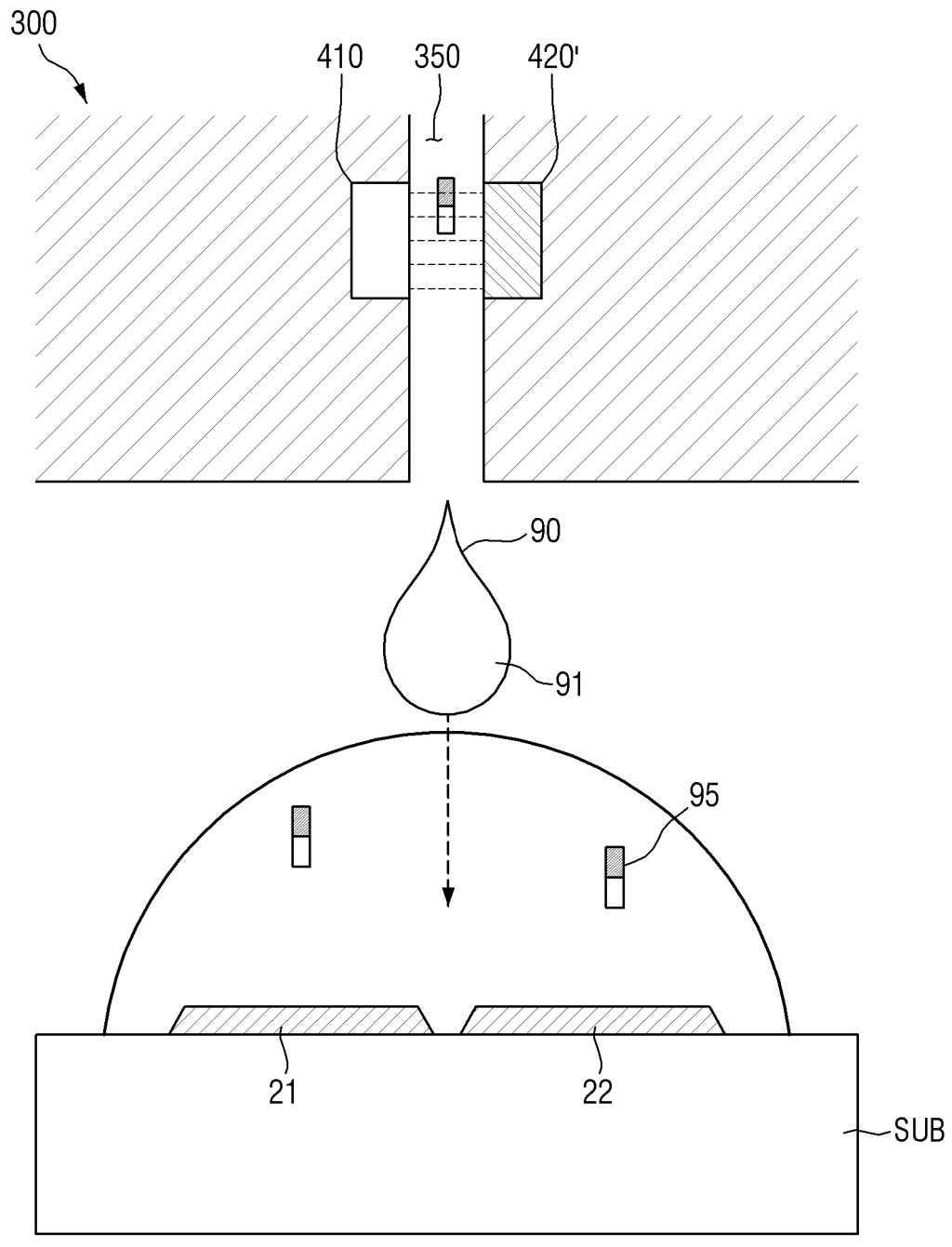

The sensing part 400 may measure the number of bipolar elements 95 ejected through the nozzle 350, and detect a change thereof. For example, as shown in FIG. 18, in case that the number of bipolar elements 95 per unit droplet of the ink 90 ejected through the nozzle 350 decreases, the sensing part 400 may determine whether the reduction exceeds a reference set value (operation S300). As another example, in case that the number of bipolar elements 95 per unit droplet of the ink 90 ejected through the nozzle 350 increases, the sensing part 400 may determine whether the increment exceeds a reference set value (operation S300). As described above, the light receiving part 420' of the sensing part 400 may detect a change in the number of bipolar elements 95 flowing in the nozzle 350 from a change in the amount or waveform of the incident light, determine whether the reference set value is exceeded according to the change in the number of bipolar elements 95, and feed back the result to the ink circulation part 500 or the inkjet head 300. As described above with reference to FIGS. 8 and 9, there may be various causes for the change in the number of bipolar elements 95, and the inkjet printing device 1000 includes the sensing part 400 and thus may provide an appropriate feedback regarding the change in the number of bipolar elements 95.

Figure 19:
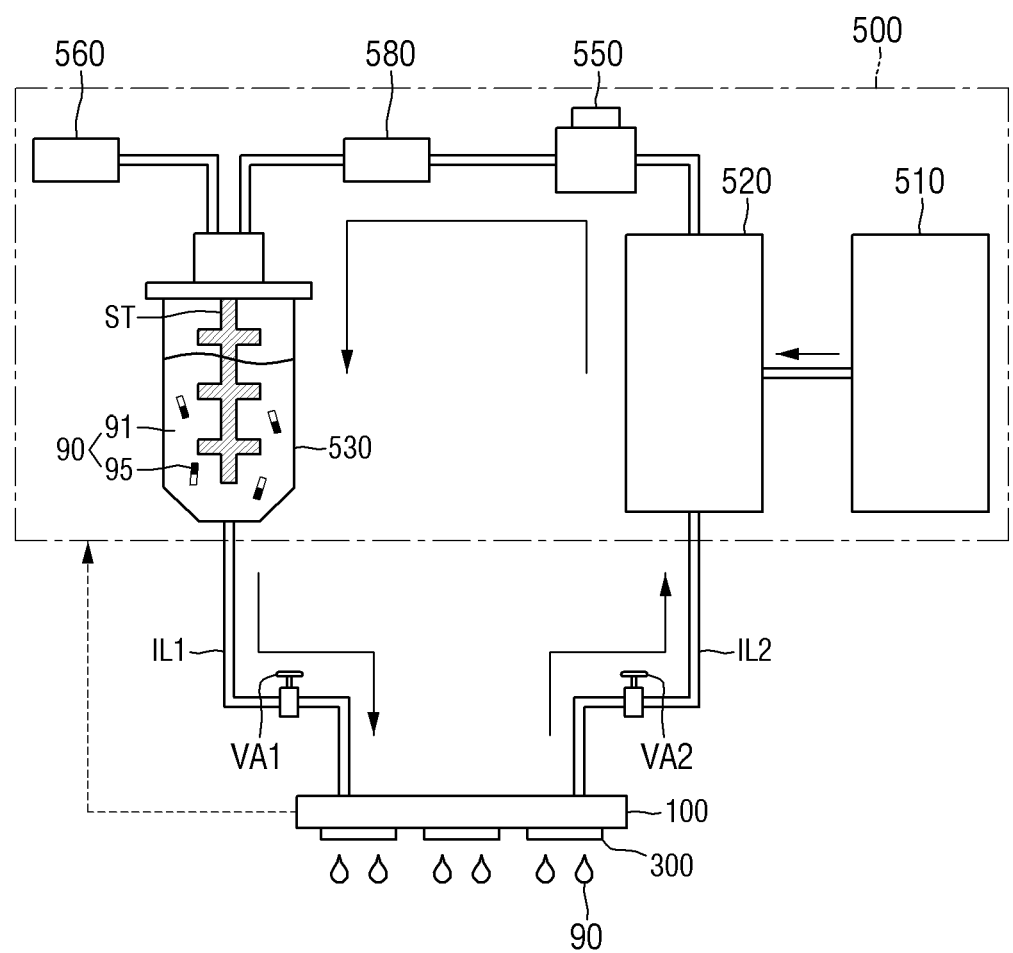

For example, as shown in FIG. 19, the sensing part 400 may detect a change in the number of bipolar elements 95 and feed it back to the ink circulation part 500. The ink circulation part 500 may receive the change in the number of the bipolar elements 95 provided from the sensing part 400 to control the operating conditions of the stirrer ST of the third ink reservoir 530, or to control the operation of a pressure pump 550, or valves VA1 and VA2 of the respective connection tubes IL1 and IL2. Such feedback may be repeated until the number of bipolar elements 95 measured by the sensing part 400 or the degree of dispersion in the ink 90 falls within a range that does not exceed a reference set value. Therefore, the inkjet printing device 1000 according to an embodiment can maintain a uniform number of bipolar elements 95 per unit droplet of the ejected ink 90, and can improve the reliability of the manufactured product.

As described above, the bipolar element 95 may have a shape extending in a direction, and each end in the extending direction may have a different polarity. The printing method of a bipolar element 95 according to an embodiment may further include mounting the bipolar elements 95 such that the extending direction of the bipolar elements 95 is directed in a direction.

Figure 20:
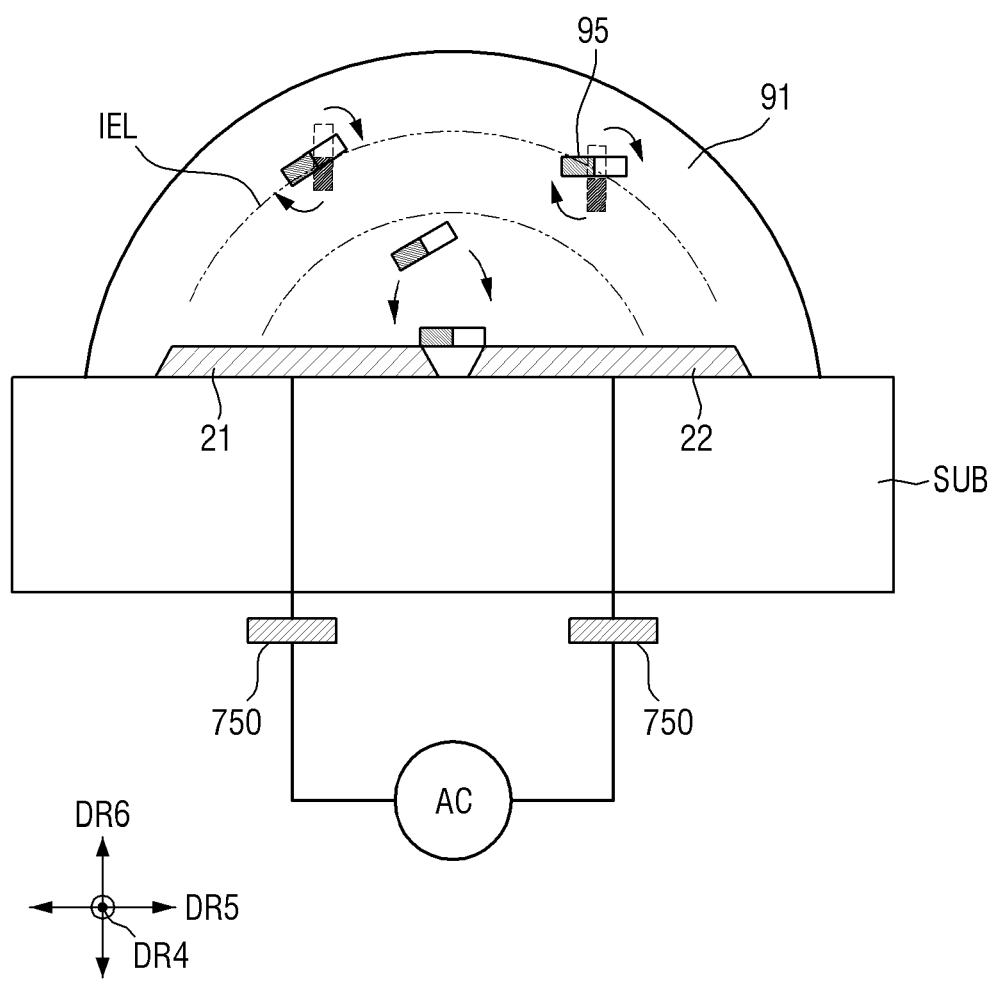

Referring to FIG. 20, in case that the ink 90 in which the bipolar elements 95 are dispersed is sprayed onto the target substrate SUB, an electric field IEL is generated on the target substrate SUB. The bipolar elements 95 may be oriented in a direction by the electric field IEL and may be mounted on the target substrate SUB. In some embodiments, the bipolar elements 95 may be subjected to a dielectrophoretic force due to the electric field IEL generated above the target substrate SUB so that the bipolar elements 95 may be disposed between the first electrode 21 and the second electrode 22.

Specifically, an electrical signal is applied to the first electrode 21 and the second electrode 22 by using a probe part 750. The probe part 750 may be connected to a pad provided on the target substrate SUB and may apply an electrical signal to the first and second electrodes 21 and 22 connected to the pad. In an embodiment, the electrical signal may be an AC voltage, and the AC voltage may have a voltage of about ±10V to about ±50V and a frequency of about 10 kHz to about 1 MHz. In case that the AC voltage is applied to the first electrode 21 and the second electrode 22, an electric field IEL may be generated between them, and the bipolar elements 95 may be subjected to a dielectrophoretic force due to the electric field IEL. The bipolar elements 95 subjected to the dielectrophoretic force may be disposed on the first electrode 21 and the second electrode 22 while their orientation directions and positions may be changed.

As shown in the drawing, the bipolar elements 95 having a shape extending in a direction within the ink 90 may vary in their orientation directions according to the direction of the electric field IEL. According to an embodiment, the bipolar element 95 may be aligned such that the direction in which the bipolar element 95 extends is directed in a direction of the electric field IEL. In case that the electric field IEL generated on the target substrate SUB is generated in parallel to the upper surface of the target substrate SUB, the direction in which the bipolar element 95 extends may be aligned to be parallel to the target substrate SUB and be disposed between the first electrode 21 and the second electrode 22. In some embodiments, orienting the bipolar elements 95 may be an operation of mounting the bipolar elements 95 between the first electrode 21 and the second electrode, and at least one end of the bipolar element 95 may be disposed on at least one of the first electrode 21 or the second electrode 22. However, the disclosure is not limited thereto, and the bipolar element 95 may be disposed directly on the target substrate SUB between the first electrode 21 and the second electrode 22.

Figure 21:
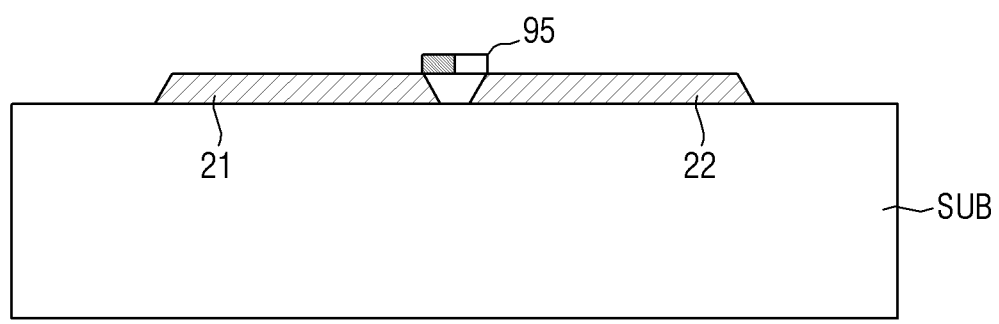
Figure 21:
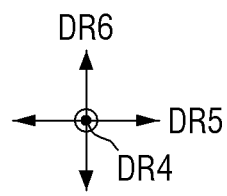

As shown in FIG. 21, the solvent 91 of the ink 90 sprayed on the target substrate SUB is removed. Removing the solvent 91 may be performed using a heat treatment device, and the heat treatment device may emit heat or infrared rays onto the target substrate SUB. The removal of the solvent 91 from the ink 90 sprayed on the target substrate SUB may prevent a flow of the bipolar elements 95 and allow the bipolar elements 95 to be mounted on the electrodes 21 and 22.

The printing method of a bipolar element 95 according to an embodiment may maintain a uniform number of bipolar elements 95 per unit droplet of the ejected ink 90 by using the inkjet printing device 1000 of FIG. 1. In addition, the printing method of a bipolar element 95 may further include mounting the bipolar elements 95 such that they are oriented in a direction. The inkjet printing device 1000 may manufacture a device including bipolar elements 95 oriented in a direction, and the device includes a uniform number of bipolar elements 95 per unit area so that the reliability of the product can be improved.

Hereinafter, various embodiments of the inkjet printing device 1000 will be described.

As described above, the inkjet printing device 1000 includes at least one sensing part 400 disposed between the inkjet head 300 and the ink circulation part 500. The sensing part 400 may measure the number of bipolar elements 95 per unit droplet of the ink 90 ejected through the nozzle 350 based on the number of bipolar elements 95 per unit volume of the ink 90 flowing in the inkjet head 300. According to an embodiment, the inkjet printing device 1000 includes a greater number of sensing parts 400 to precisely measure the number of bipolar elements 95 in the ejected ink 90, and may accurately determine the cause of the change in the number of bipolar elements 95.

Figure 22:
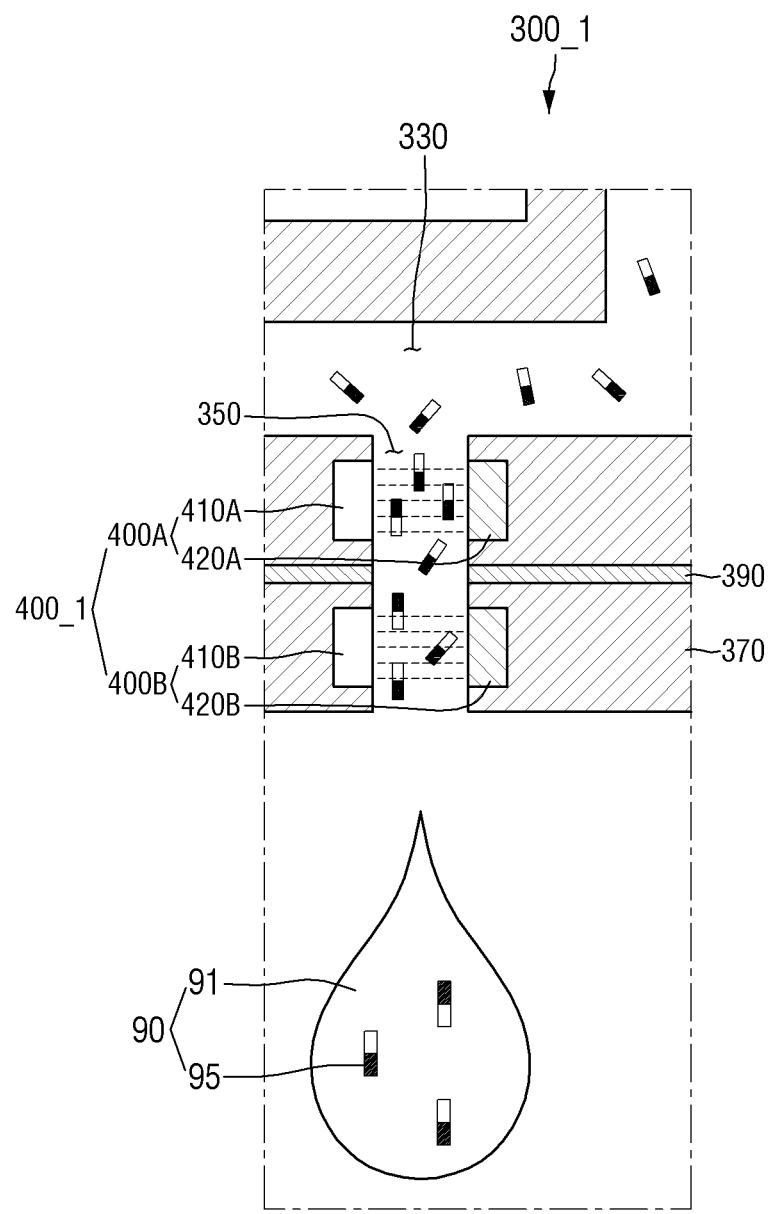
FIGS. 22 and 23 are schematic partial cross-sectional view of an inkjet head according to an embodiment.
Figure 23:
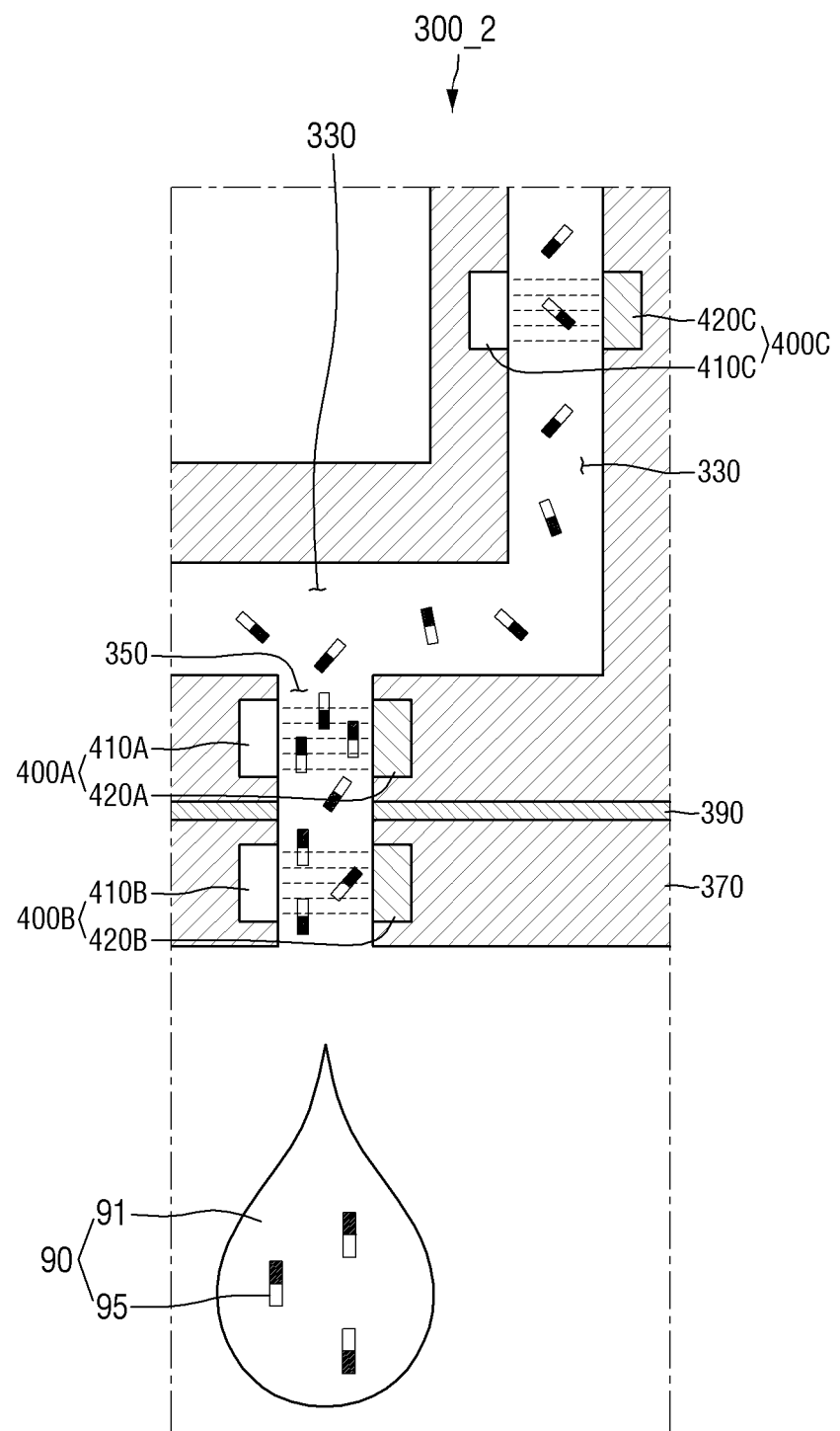

FIGS. 22 and 23 are schematic partial cross-sectional views of an inkjet head according to an embodiment.

Referring to FIG. 22, a sensing part 400_1 may include a first sensing part 400A disposed above an actuator 390 of an inkjet head 300_1 and a second sensing part 400B disposed under the actuator 390. The embodiment of FIG. 22 is different from the embodiment of FIG. 6 in that the second sensing part 400B is disposed in the inkjet head 300_1. Hereinafter, redundant descriptions will be omitted and the following description will focus on differences.

The first sensing part 400A may be disposed between the actuator 390 and the inner tube 330 and disposed adjacent to an inlet 351 of a nozzle 350. The first sensing part 400A may measure the number of bipolar elements 95 in at least the ink 90 introduced into the nozzle 350. The second sensing part 400B may be disposed to be spaced apart from the first sensing part 400A with the actuator 390 interposed therebetween, and may be disposed adjacent to an outlet 353 of the nozzle 350. The second sensing part 400B may measure the number of bipolar elements 95 in the ink 90 just before passing through the actuator 390 and being ejected from the inkjet head 300.

The inkjet printing device 1000 according to an embodiment may include a greater number of sensing parts 400_1 to more precisely measure the number of bipolar elements 95 in the ejected ink 90. In addition, a more accurate analysis of causes of a change in the number of bipolar elements 95 is possible. For example, since the first sensing part 400A and the second sensing part 400B are spaced apart from each other with the actuator 390 interposed therebetween, whether the number of bipolar elements 95 is changed by the actuator 390 may be determined based on the number of bipolar elements 95 detected by the first sensing part 400A and the second sensing part 400B.

Similarly, the inkjet printing device 1000 may include a greater number of sensing parts 400 to more precisely detect a change in the number of bipolar elements 95.

Referring to FIG. 23, a sensing part 400_2 of the inkjet printing device 1000 may further include a third sensing part 400C in which a light emitting part 410 and a light receiving part 420 of an inkjet head 300_2 are disposed on a base part 310 with the inner tube 330 interposed therebetween. For example, the first to third sensing parts 400A to 400C may include first to third light emitting parts 410A to 410C and first to third receiving parts 410A to 410C. The embodiment of FIG. 23 is different from the embodiment of FIG. 22 in that a third sensing part 400C is disposed on the inkjet head 300_2. Hereinafter, redundant descriptions will be omitted and the following description will focus on differences.

In the third sensing part 400C, the light emitting part 410 and the light receiving part 420 may be disposed on the base part 310 with the inner tube 330 interposed therebetween. The sensing part 400_2 further includes the third sensing part 400C in addition to the first sensing part 400A and the second sensing part 400B, and thus may measure the number of bipolar elements 95 in the ink 90 flowing along the inner tube 330.

As described above, the ink 90 may be introduced into the inkjet head 300_2 in case that the degree of dispersion of the bipolar elements 95 is lowered at the time of supply of the ink 90 from the ink circulation part 500. In case that the sensing part 400_2 includes only the first sensing part 400A and the second sensing part 400B, it may be difficult to accurately determine whether the number of bipolar elements 95 in the ink 90 supplied from the ink circulation part 500 is reduced or the reduction in number is due to clogging of the bipolar element 95 at the inlet 351 of the nozzle 350. According to an embodiment, the sensing part 400_2 may further include the third sensing part 400C capable of measuring the number of bipolar elements 95 in the ink 90 flowing through the inner tube 330 and thus may more accurately determine a change in the number of bipolar elements 95 due to the ink 90 supplied to the inkjet head 300_2.

Figure 24:
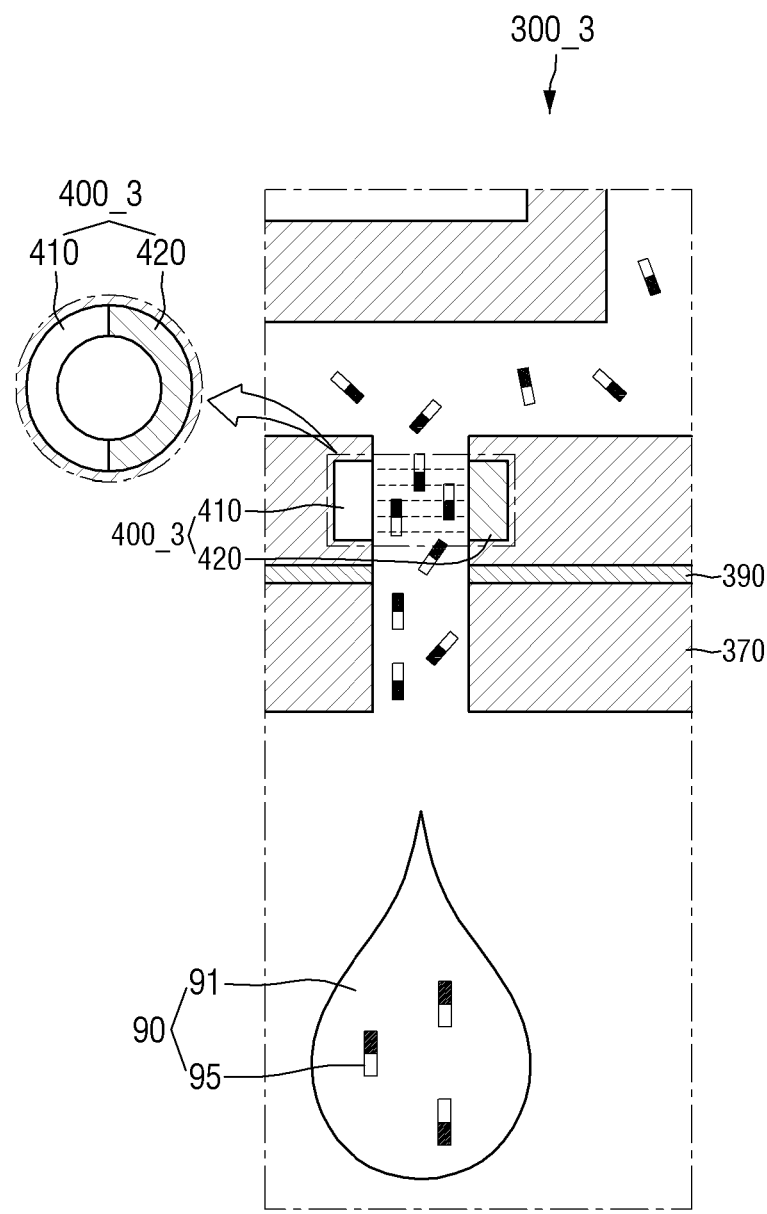
FIG. 24 is a schematic partial cross-sectional view of an inkjet head according to another embodiment.

FIG. 24 is a schematic partial cross-sectional view of an inkjet head according to another embodiment.

Referring to FIG. 24, a sensing part 400_3 according to an embodiment may be disposed such that a light emitting part 410 and a light receiving part 420 surround the nozzle 350. A nozzle 350 of an inkjet head 300_3 may extend in a direction and may have a circular shape in a cross-sectional view, and the light emitting part 410 and the light receiving part 420 may be disposed to partially surround the outer wall of the nozzle 350. Accordingly, light emitted by the light emitting part 410 may be emitted to the ink 90 over a wider range, and most of the light L emitted by the light emitting part 410 and light L' scattered by the bipolar elements 95 may be incident on the light receiving part 420. The sensing part 400_3 may be formed to surround the nozzle 350 to accurately measure the number of bipolar elements 95 in the ink 90. Hereinafter, redundant descriptions will be omitted.

The light emitting part 410 and the light receiving part 420 of the sensing part 400 may not be necessarily disposed within an ejecting part 370 of a base part 310. In some embodiments, at least one of the light emitting part 410 and the light receiving part 420 of the sensing part 400 may be inserted into the ejecting part 370 and the other may be disposed on the outer surface of the base part 310.

Figure 25:
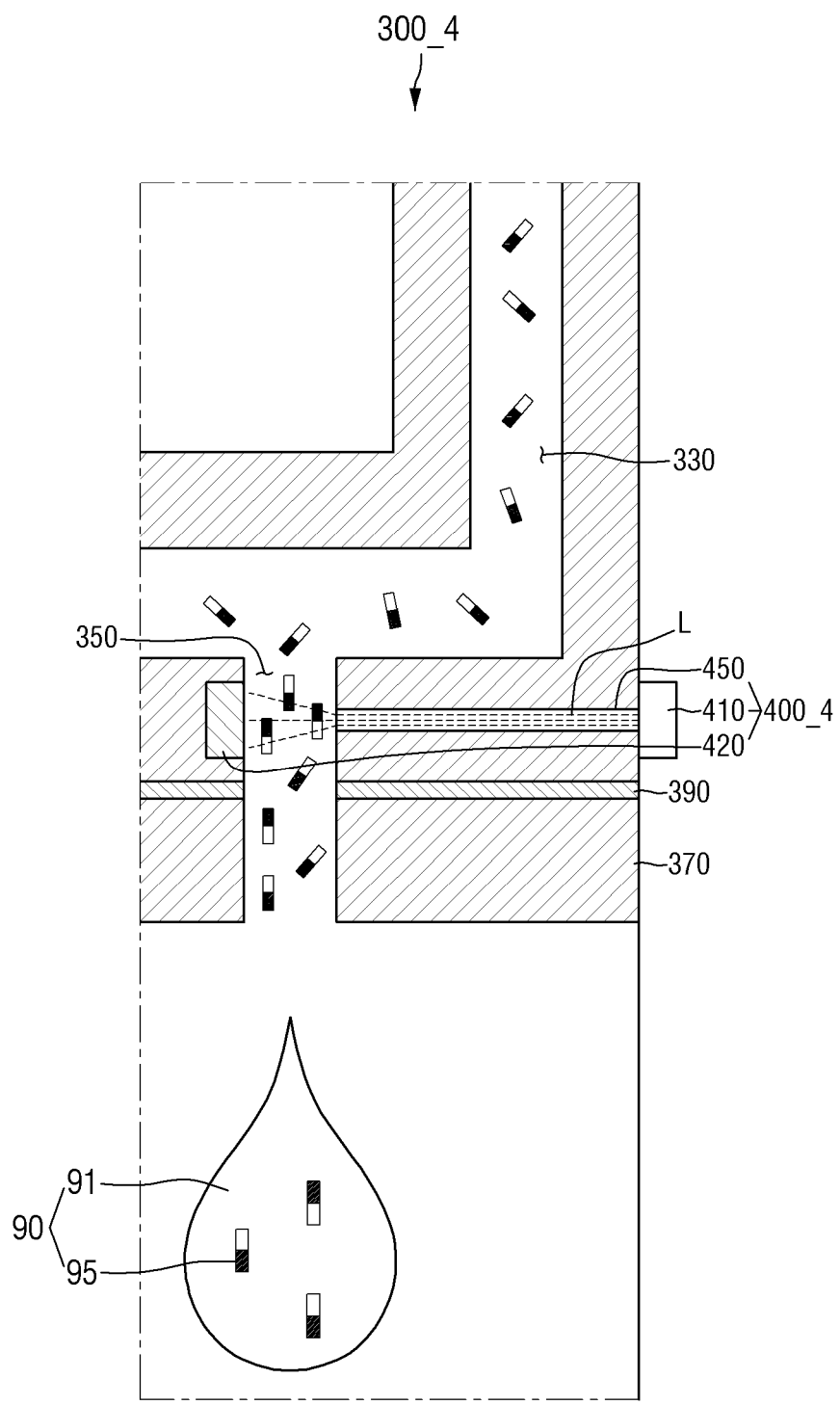
FIG. 25 is a schematic partial cross-sectional view of an inkjet head according to another embodiment.

FIG. 25 is a schematic partial cross-sectional view of an inkjet head according to another embodiment.

Referring to FIG. 25, a sensing part 400_4 according to an embodiment may include a light emitting part 410 which is disposed on the outer surface of the base part 310 and a light receiving part 420 which is inserted into an ejecting part 370 of a base part 310. The sensing part 400_4 may further include a light transmitting part 450 which is inserted into the ejecting part 370 and disposed between the nozzle 350 and the light emitting part 410 to transmit light L emitted by the light emitting part 410 into the nozzle 350. The embodiment of FIG. 25 is different from the embodiment of FIG. 6 in that the sensing part 400_4 further includes the light transmitting part 450 and the arrangement of the light emitting part 410 and the light receiving part 420 is different. Hereinafter, redundant descriptions will be omitted and the following description will focus on differences.

Since the base part 310 of the inkjet head 300_4 is integrally formed with the ejecting part 370, it may not be easy to insert the sensing part 400_4 into the ejecting part 370. In some embodiments, the light emitting part 410 and the light receiving part 420 of the sensing part 400_4 may be disposed to be spaced apart from each other with the nozzle 350 interposed therebetween, and the sensing part 400_4 may further include the light transmitting part 450 which is disposed between the light emitting part 410 and the light receiving part 420 and transmits the light L of the light emitting part 410 into the nozzle 350.

The light transmitting part 450 may be inserted into the ejecting part 370, and may be disposed between the nozzle 350 and the light emitting part 410. The light transmitting part 450 is disposed in contact with at least the outer wall of the nozzle 350, and the light emitted by the light emitting part 410 may be smoothly emitted into the nozzle 350. In some embodiments, the light transmitting part 450 may be formed of an optical fiber to minimize a change in the waveform of the light L emitted by the light emitting part 410. The light L emitted by the light emitting part 410 may be emitted to the ink 90 in the nozzle 350 through the light transmitting part 450. However, the disclosure is not limited thereto.

In addition, although it is illustrated in the drawing that the light receiving part 420 is inserted into the ejecting part 370, the disclosure is not limited thereto, and the light emitting part 410 may be inserted into the ejecting part 370. However, while the light L emitted from the light emitting part 410 and the light L' scattered by the bipolar elements 95 are incident on the light receiving part 420 through the light transmitting part 450, the wavelength may change. Accordingly, the light receiving part 420 of the sensing part 400_4 including the light transmitting part 450 may be inserted into the ejecting part 370.

Figure 26:
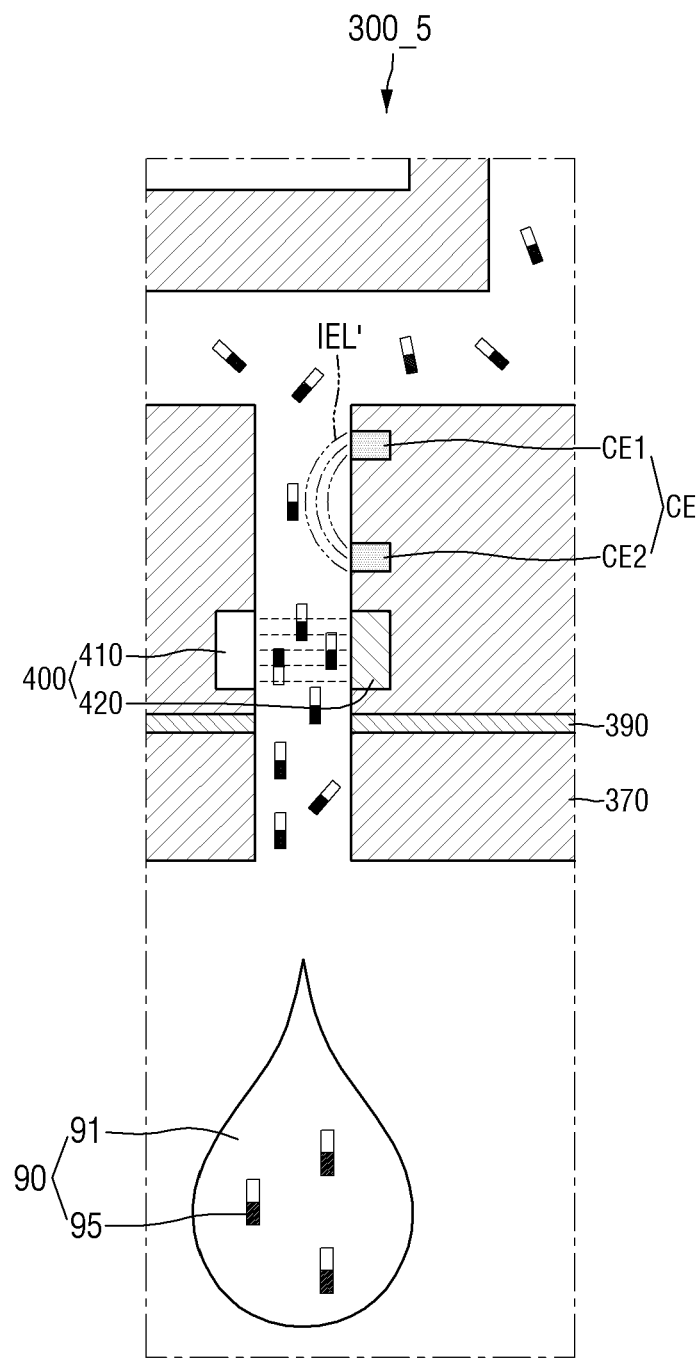
FIG. 26 is a schematic partial cross-sectional view of an inkjet head according to another embodiment.

FIG. 26 is a schematic partial cross-sectional view of an inkjet head according to another embodiment.

Referring to FIG. 26, an inkjet head 300_5 may include an electric field generating electrode CE disposed on an ejecting part 370, and the electric field generating electrode CE may generate an electric field IEL in a nozzle 350 or an inner tube 330 of the inkjet head 300_5. Bipolar elements 95 may flow along the inner tube 330 and pass through the electric field IEL' generated by the electric field generating electrode CE before being ejected through the nozzle 350. The bipolar element 95 may include a first end and a second end having polarities, and may be oriented such that a long axis thereof is directed in a direction while passing through the electric field IEL'.

The electric field generating electrode CE may be disposed on a base part 310 of the inkjet head 300. For example, the electric field generating electrode CE may be disposed on an ejecting part 370 of the base part 310 on which the nozzle 350 is disposed.

According to an embodiment, the electric field generating electrode CE may be disposed in the ejecting part 370 which is disposed on a side with respect to the nozzle 350. For example, the electric field generating electrode CE may be disposed in the ejecting part 370, may be disposed on a portion positioned on a side of the nozzle 350, and may not be disposed on a portion positioned on another side of the nozzle 350. However, the disclosure is not limited thereto, and the electric field generating electrode CE may be disposed over the entire surface of the ejecting part 370. As described above, the inkjet head 300 may have a shape extending in the first direction DR1 and the second direction DR2, and the electric field generating electrode CE may be disposed on the ejecting part 370 and extend in at least a direction.

In some embodiments, the electric field generating electrode CE may be inserted into the ejecting part 370 of the inkjet head 300, and may have a shape extending in the second direction DR2 along nozzles 350 arranged in the second direction DR2. Also, the electric field generating electrode CE may be disposed between the nozzles 350 spaced apart from each other in the first direction DR1. For example, an electric field generating electrode CE may extend in the second direction DR2 and may be disposed to be spaced apart from electric field generating electrodes CE neighboring in the first direction DR1. At least one nozzle 350 may be arranged between an electric field generating electrode CE and another electric field generating electrode CE neighboring in the first direction DR1. Accordingly, an electric field IEL' may be generated in a nozzle 350 by an electric field generating electrode CE. It is illustrated in the drawing that an electric field generating electrode CE is disposed on a side of the nozzle 350, corresponding to the at least one nozzle 350, but the disclosure is not limited thereto. In case that the electric field generating electrode CE is disposed over the entire surface of the ejecting part 370, each of the nozzles 350 may have a shape surrounded by the electric field generating electrode CE.

The electric field generating electrode CE may include a first electric field generating electrode CE1 and a second electric field generating electrode CE2. An electrical signal may be applied to the first electric field generating electrode CE1 and the second electric field generating electrode CE2, and an electric field IEL' may be generated between them. The first electric field generating electrode CE1 and the second electric field generating electrode CE2 may be spaced apart from each other in a direction in which the nozzle 350 extends, and the electric field IEL' may be generated in a direction in which they are spaced apart from each other. Although not shown in the drawing, the electric field generating electrode CE may be connected to a power device included in the inkjet head 300 or the printhead part 100, and an electrical signal for generating the electric field IEL' may be applied to the electric field generating electrode CE. In some embodiments, the electrical signal may be an AC voltage.

With the electric signal applied, the electric field generating electrode CE disposed in the ejecting part 370 may generate the electric field IEL' in at least the nozzle 350. The bipolar element 95 ejected through the nozzle 350 may be aligned so that the first end and the second end having polarities are directed in a specific direction by the electric field IEL' generated by the electric field generating electrode CE. For example, the inkjet head 300 includes the electric field generating electrode CE so that not only aggregation of the bipolar elements 95 at an inlet 351 of the nozzle 350 is prevented but also the bipolar elements 95 are oriented in a specific direction within the ink 90 ejected from an outlet 353 of the nozzle 350.

The bipolar elements 95 may pass through the electric field IEL' generated by the electric field generating electrode CE, before they are ejected through the nozzle 350. As the bipolar elements 95 dispersed in a solvent 91 of the ink 90 passes through the electric field TEL', induced dipole moments may be formed, and the bipolar elements 95 with the induced dipole moments may be subjected to a dielectrophoretic force due to the electric field IEL'. The orientation directions of the bipolar elements 95 subjected to the dielectrophoretic force may be changed in the ink 90. The induced dipole moment may be formed in a direction toward which a first end having a first polarity of the bipolar element 95 or a second end having a second polarity is directed. As described above, the bipolar elements 95 dispersed in the ink 90 supplied to the inner tube 330 may have random orientation directions. However, in the bipolar elements 95 passing through the electric field IEL' generated in the nozzle 350, an end, for example, the first end or the second end having a polarity, may be oriented in a specific direction by the dielectrophoretic force. For example, the directions in which the long axes of the bipolar elements 95 ejected through the nozzle 350 are directed may be oriented in a same direction. The electric field generating electrode CE may generate an electric field IEL' in a direction in which the nozzle 350 extends, and the bipolar element 95 may be arranged such that a direction of the long axis is directed in a direction in which the electric field IEL' is directed, for example, the direction in which the nozzle 350 extends.

In addition, in the inkjet printing device 1000, even in case that the bipolar elements 95 with random orientation directions are supplied to the inner tube 330, the bipolar elements 95 may be oriented in a direction by the electric field IEL' generated by the electric field generating electrode CE. Accordingly, even in case that the nozzle 350 has a narrower diameter than that of the inner tube 330, the inkjet head 300 may prevent the clogging of the inlet 351 of the nozzle 350 due to aggregation of the bipolar elements 95.

Accordingly, as shown in FIG. 9, a change in the number of bipolar elements 95 due to the aggregation of the bipolar elements 95 in the process of introducing the bipolar elements 95 into the inlet 351 of the nozzle may be prevented. As another example, even in case that the inlet 351 of the nozzle 350 is clogged as the bipolar elements 95 are aggregated, the sensing part 400 may detect a change in the number of the bipolar elements 95 and feed it back to the electric field generating electrode CE. The electric field generating electrode CE may receive the feedback transmitted from the sensing part 400 and generate a stronger electric field IEL' to solve the clogging of the inlet 351 of the nozzle 350.

In addition, the bipolar elements 95 may each include a first end having a first polarity and a second end having a second polarity and a direction in which the first end having the first polarity is directed may be controlled according to the direction of the electric field IEL'. According to an embodiment, the bipolar elements 95 ejected from the inkjet head 300 may be oriented such that an end of each bipolar element 95 having an arbitrary polarity is directed in a same direction. The inkjet head 300 including the electric field generating electrode CE may eject the ink 90 in which the bipolar elements 95 with a constant orientation direction are dispersed, and the ink 90 ejected from the inkjet head 300 may be sprayed onto the target substrate SUB, as described above.

Figure 27:
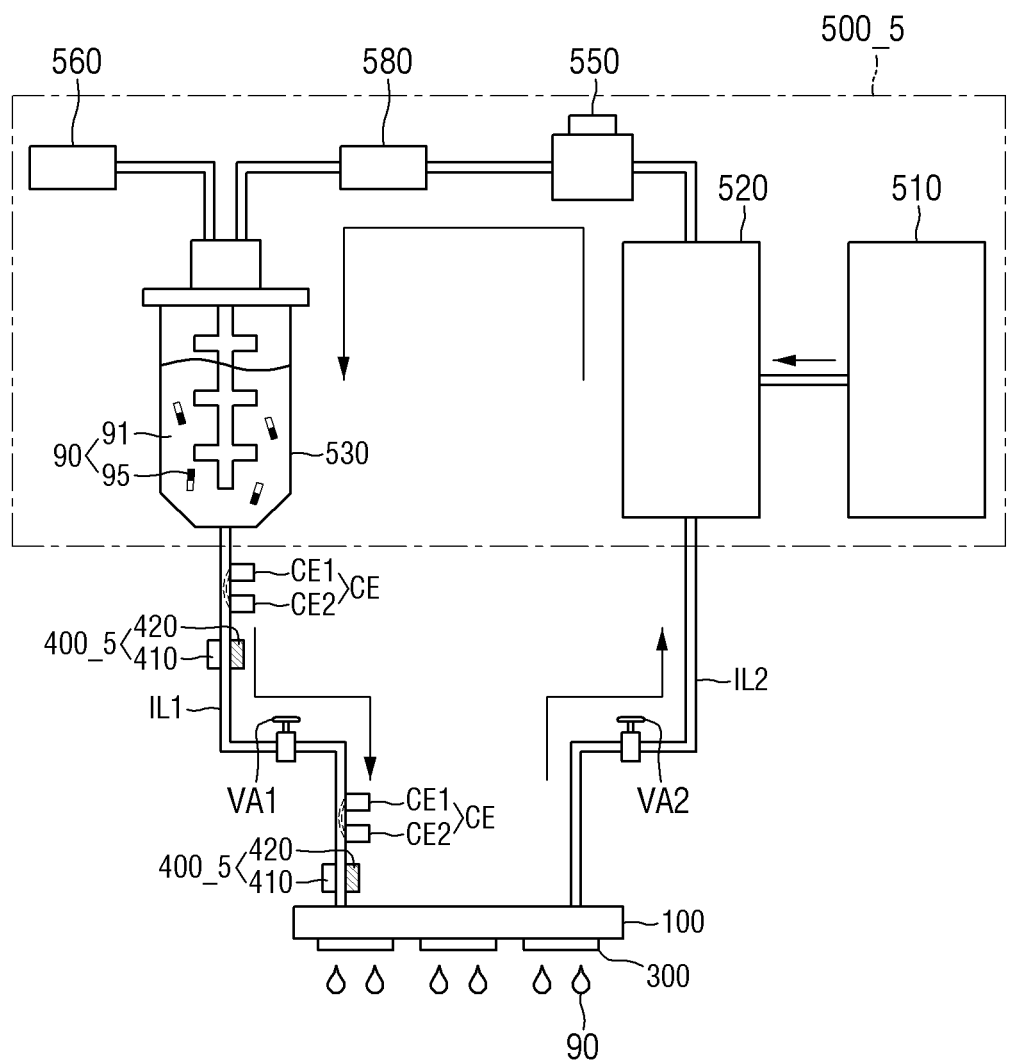
FIG. 27 is a schematic diagram illustrating an ink circulation part and a printhead part according to an embodiment.

FIG. 27 is a schematic diagram illustrating an ink circulation part and a printhead part according to an embodiment.

Referring to FIG. 27, the inkjet printing device 1000 according to an embodiment may further include a sensing part 400_5 and an electric field generating electrode CE disposed between an ink circulation part 500_5 and an inkjet head 300. At least one sensing part 400_5 and at least one electric field generating electrode CE may be respectively disposed in a first connection tube IL1 through which ink 90 is supplied from the ink circulation part 500_5 to the inkjet head 300. It is illustrated in the drawing that a sensing part 400_5 and an electric field generating electrode CE are disposed adjacent to a third ink reservoir 530 of the ink circulation part 500_5 and the inkjet head 300, but the disclosure is not limited thereto.

In case that the number of bipolar elements 95 in the ink 90 supplied to the inkjet head 300 is small, the ink circulation part 500 and the electric field generating electrode CE operate by receiving a change in the number of the bipolar elements 95 which is detected by the sensing part 400_5. For example, the ink circulation part 500 may increase the degree of dispersion of the bipolar elements 95 by adjusting the operating conditions of the stirrer ST of the third ink reservoir 530, or the electric field generating electrode CE may generate an electric field IEL' in the first connection tube IL1 to prevent aggregation of the bipolar elements 95 in the first connection tube IL1. A detailed description thereof is the identical to that given above.

The inkjet printing device 1000 of FIG. 27 may measure the number of bipolar elements 95 in the ink 90 flowing through the first connection tube IL1 by using the sensing part 400_5. According to an embodiment, the inkjet printing device 1000 may more accurately determine a case in which the change in the number of bipolar elements 95 in the ink 90 is caused by the degree of dispersion of the bipolar elements 95 in the ink 95 supplied from the ink circulation part 500.

Through the above method, the inkjet printing device 1000 according to an embodiment may print the bipolar elements 95 on the target substrate SUB.

The above-described bipolar element 95 may be a light emitting element including semiconductor layers, and according to an embodiment, a display device including the light emitting element may be manufactured using the inkjet printing device 1000.

Figure 28:
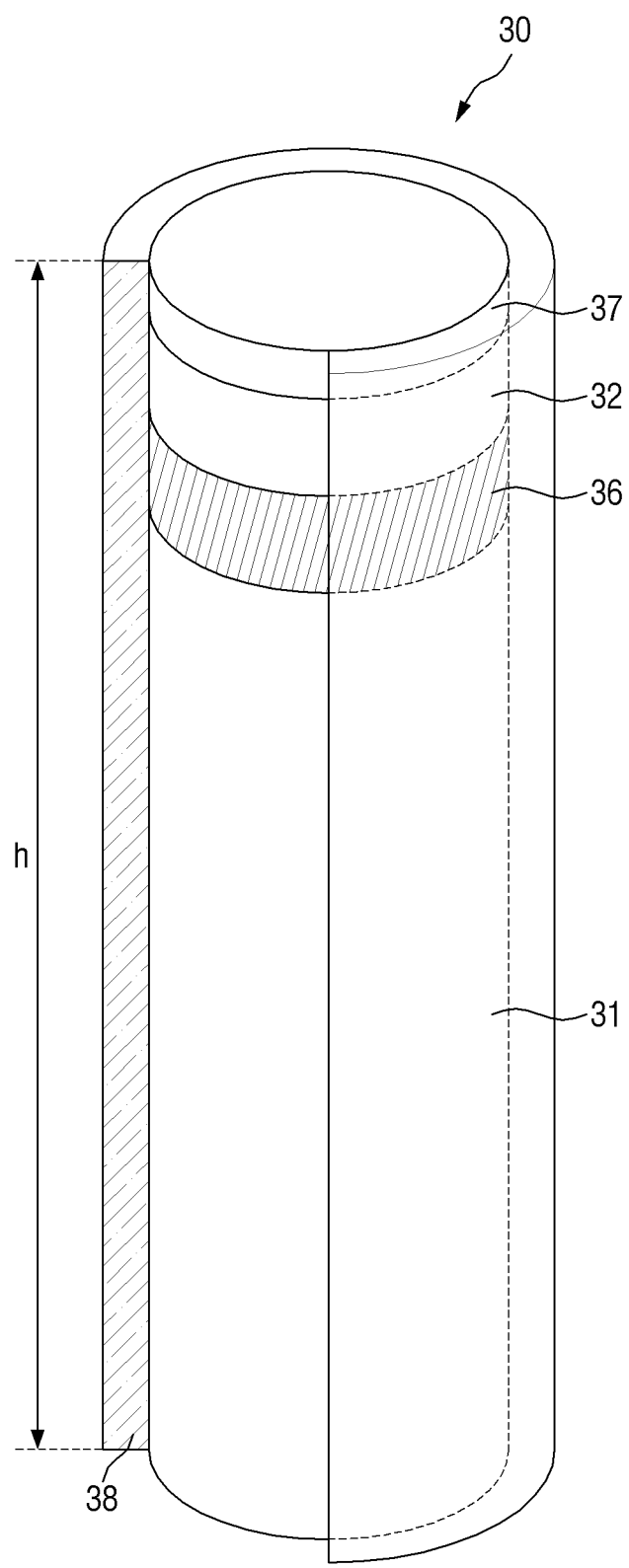
FIG. 28 is a schematic diagram illustrating a light emitting element according to an embodiment.

FIG. 28 is a schematic diagram illustrating a light emitting element according to an embodiment.

A light emitting element 30 may be a light emitting diode (LED). Specifically, the light emitting element 30 may be an inorganic LED having a size of micrometers or nanometers and may be made of an inorganic material. In case that an electric field is formed in a specific direction between two electrodes facing each other, the inorganic LED may be aligned between the two electrodes of which polarity is formed. The light emitting element 30 may be aligned between the two electrodes by the electric field formed on the electrodes.

The light emitting element 30 according to an embodiment may have a shape extending in a direction. The light emitting element 30 may be in a shape of a rod, a wire, a tube, or the like. In an embodiment, the light emitting element 30 may have a cylindrical or rod shape. However, the shape of the light emitting element 30 is not limited thereto, and the light emitting element 30 may have a polygonal prism shape, such as a regular cube, a rectangular parallelepiped, and a hexagonal prism, or may have various other suitable shapes, such as a shape extending in a direction and having a partially inclined outer surface. Semiconductors included in the light emitting element 30, which will be described in more detail below, may have a structure in which they are sequentially arranged or stacked in the a direction.

The light emitting element 30 may include a semiconductor layer doped with any conductivity type (e.g., p-type or n-type) impurities. The semiconductor layer may emit light in a specific wavelength range by receiving an electrical signal applied from an external power source.

In some embodiments, the light emitting element 30 may have a shape extending in a direction. The light emitting element 30 may have a shape of a nanorod, a nanowire, a nanotube, or the like. In an embodiment, the light emitting element 30 may have a cylindrical or rod shape. However, the shape of the light emitting element 30 is not limited thereto, and the light emitting element 30 may have various shapes, such as a regular cube, a rectangular parallelepiped, a hexagonal prism, and the like.

Referring to FIG. 28, the light emitting element 30 may include a first semiconductor layer 31, a second semiconductor layer 32, an active layer 36, an electrode layer 37, and an insulating layer 38.

The first semiconductor layer 31 may be an n-type semiconductor. For example, in case that the light emitting element 30 emits light of a blue wavelength band, the first semiconductor layer 31 may include a semiconductor material having a chemical formula of $Al_xGa_yIn_{1-x-y}N$ ($0 \leq x \leq 1$, $0 \leq y \leq 1$, $0 \leq x+y \leq 1$). For example, the material may be one or more of n-type doped AlGaInN, GaN, AlGaN, InGaN, AlN, and InN. The first semiconductor layer 31 may be doped with an n-type dopant, and the n-type dopant may be, for example, Si, Ge, Sn, or the like. In an embodiment, the first semiconductor layer 31 may be n-GaN doped with n-type Si.

The length of the first semiconductor layer 31 may be in a range of about 1.5 μm to about 5 μm, but is not limited thereto.

The second semiconductor layer 32 is disposed on the active layer 36, which will be described in more detail below. The second semiconductor layer 32 may be a p-type semiconductor. For example, in case that the light emitting element 30 emits light of a blue or green wavelength band, the second semiconductor layer 32 may include a semiconductor material having a chemical formula of $Al_xGa_yIn_{1-x-y}N$ ($0 \leq x \leq 1$, $0 \leq y \leq 1$, $0 \leq x+y \leq 1$). For example, the material may be any one or more of p-type doped AlGaInN, GaN, AlGaN, InGaN, AlN, and InN. The second semiconductor layer 32 may be doped with a p-type dopant, and the p-type dopant may be, for example, Mg, Zn, Ca, Se, Ba, or the like. In an embodiment, the second semiconductor layer 32 may be p-GaN doped with p-type Mg. The length of the second semiconductor layer 32 may be in a range of about 0.05 μm to about 0.10 μm, but is not limited thereto.

Although FIG. 28 illustrates that the first semiconductor layer 31 and the second semiconductor layer 32 are formed as a layer, the disclosure is not limited thereto. According to some embodiments, depending on the material of the active layer 36, the first semiconductor layer 31 and the second semiconductor layer 32 may include a greater number of layers (e.g., may further include other layers), such as a cladding layer or a tensile strain barrier reducing (TSBR) layer.

The active layer 36 is disposed between the first semiconductor layer 31 and the second semiconductor layer 32. The active layer 36 may include a material having a single or multiple quantum well structure. In case that the active layer 36 includes a material having a multiple quantum well structure, the active layer 36 may have a structure in which quantum layers and well layers may be alternately stacked. The active layer 36 may emit light by the coupling of electron-hole pairs according to an electrical signal applied through the first semiconductor layer 31 and the second semiconductor layer 32. The active layer 36 may include a material, such as AlGaN or AlGaInN. Particularly, in case that the active layer 36 has a structure in which quantum layers and well layers are alternately stacked in a multiple quantum well structure, the quantum layer may include a material, such as AlGaN or AlGaInN, and the well layer may include a material, such as GaN or AlInN.

However, the disclosure is not limited thereto, and the active layer 36 may have a structure in which semiconductor materials having large band gap energy and semiconductor materials having small band gap energy are alternately stacked, and the active layer 36 may include other Group III to V semiconductor materials according to the wavelength band of the emitted light. The active layer 36 is not limited to emitting light of a blue wavelength band, and it may emit light of a red or green wavelength band in some embodiments. The length of the active layer 36 may be in a range of about 0.05 μm to about 0.10 μm, but is not limited thereto.

The active layer 36 may emit light at side surfaces as well as the outer surface of the light emitting element 30 in a length direction. The directionality of light emitted from the active layer 36 is not limited to a direction.

The electrode layer 37 may be an ohmic contact electrode. However, the disclosure is not limited thereto, and the electrode layer 37 may be a Schottky contact electrode. The light emitting element 30 may include at least one electrode layer 37. Although the light emitting element 30 shown in FIG. 28 includes an electrode layer 37, the disclosure is not limited thereto. In some embodiments, the light emitting element 30 may include a greater number of electrode layers 37 or may be omitted. The following description of the light emitting element 30 may be equally applied even in case that the number of electrode layers 37 is different or further includes other structures.

In the display device 10 according to one embodiment, in case that the light emitting element 30 is electrically connected to an electrode or a contact electrode, the electrode layer 37 may reduce the resistance between the light emitting element 30 and the electrode or contact electrode. The electrode layer 37 may include a conductive metal. For example, the electrode layer 37 may include at least one of aluminum (Al), titanium (Ti), indium (In), gold (Au), silver (Ag), indium tin oxide (ITO), indium zinc oxide (IZO), or indium tin zinc oxide (ITZO). Further, the electrode layer 37 may include an n-type or p-type doped semiconductor material. The electrode layer 37 may include a same material or different materials, but the disclosure is not limited thereto.

The insulating layer 38 is disposed to surround the outer surfaces of the semiconductor layers and electrode layers of the light emitting element 30 described above. In an embodiment, the insulating layer 38 may be disposed to surround at least the outer surface of the active layer 36, and may extend in the direction in which the light emitting element 30 extends. The insulating layer 38 may function to protect the members. For example, the insulating layer 38 may be formed to surround side surfaces of the members while exposing ends of the light emitting element 30 in the length direction.

Although FIG. 28 illustrates that the insulating layer 38 extends in the length direction of the light emitting element 30 to cover a region from the first semiconductor layer 31 to the side surface of the electrode layer 37, the disclosure is not limited thereto. The insulating layer 38 may cover only the outer surfaces of some of the semiconductor layers and the active layer 36 or may cover only a portion of the outer surface of the electrode layer 37 to partially expose the outer surface of the electrode layer 37. Further, in a cross-sectional view, the insulating layer 38 may have an upper surface, which is rounded in a region adjacent to at least one end portion of the light emitting element 30.

The thickness of the insulating layer 38 may be in a range of about 10 nm to about 1.0 μm, but is not limited thereto. The thickness of the insulating layer 38 may be about 40 nm.

The insulating layer 38 may include materials having insulating properties. For example, the insulating layer 38 may include at least one of silicon oxide ($SiO_x$), silicon nitride ($SiN_x$), silicon oxynitride ($SiO_xN_y$), aluminum nitride ($AlN_x$), aluminum oxide ($AlO_x$), zirconium oxide ($ZrO_x$), hafnium oxide ($HfO_x$), or titanium oxide ($TiO_x$). Although FIG. 28 illustrates that the insulating layer 38 is formed as a single layer, the disclosure is not limited thereto. In some embodiments, the insulating layer 38 may be formed in a multilayer structure in which layers are stacked. Accordingly, an electrical short circuit that may occur in case that the active layer 36 directly contacts the electrode through which the electrical signal is transmitted to the light emitting element 30 may be prevented. In addition, because the insulating layer 38 protects the outer surface of the light emitting element 30 including the active layer 36, a reduction in luminous efficiency may be prevented.

Further, in some embodiments, the insulating layer 38 may have an outer surface subjected to surface treatment. In case that the display device 10 is manufactured, the light emitting element 30 dispersed in ink may be sprayed onto electrodes and aligned. Here, the surface of the insulating film 38 may be hydrophobic or hydrophilic-treated so that the light emitting element 30 is kept separate in the ink without being aggregated with other adjacent light emitting elements 30.

The light emitting element 30 may have a length h in a range of about 1 µm to about 10 µm, or in a range of about 2 µm to about 6 µm, and, e.g., in a range of about 3 µm to about 5 µm. Further, a diameter of the light emitting element 30 may be in a range of about 30 nm to about 700 nm, and an aspect ratio of the light emitting element 30 may be in a range of about 1.2 to about 100. However, the disclosure is not limited thereto, and the light emitting elements 30 included in the display device 10 may have different diameters according to a difference in composition of the active layer 36. The diameter of the light emitting element 30 may be about 500 nm.

According to an embodiment, the inkjet printing device 1000 may disperse the light emitting elements 30 in the ink 90 and spray or eject the ink 90 onto the target substrate SUB, and thereby may manufacture the display device 10 including the light emitting elements 30.

Figure 29:
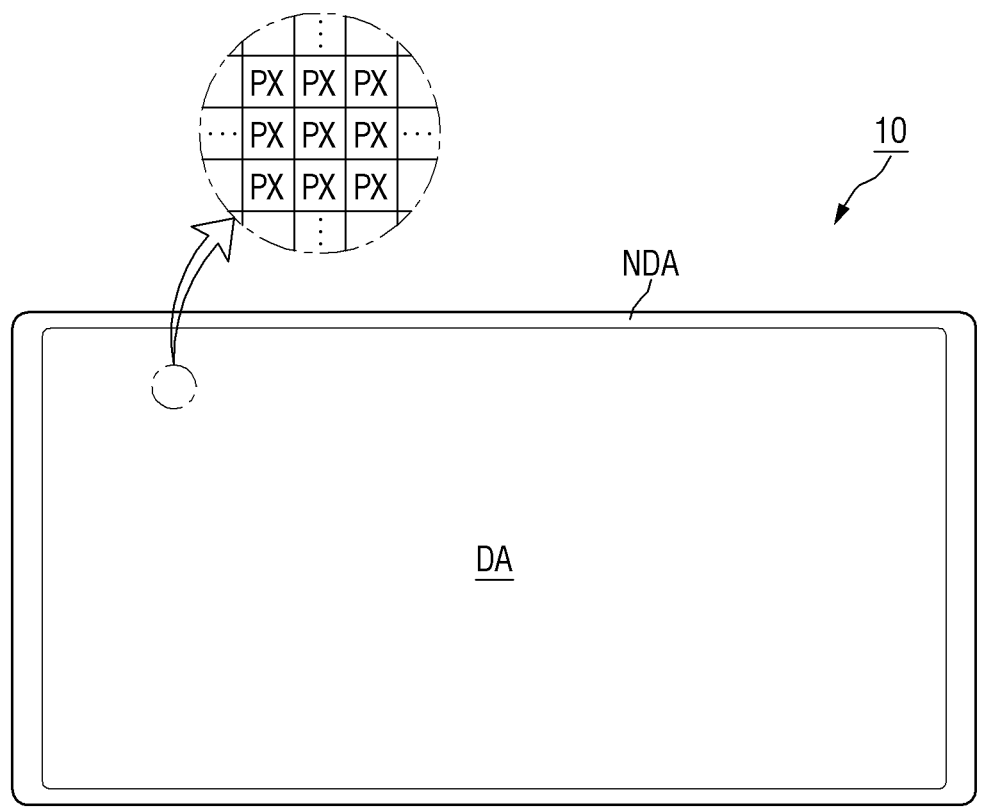
FIG. 29 is a schematic plan view of a display device according to an embodiment.

FIG. 29 is a schematic plan view of a display device according to an embodiment.

Referring to FIG. 29, a display device 10 displays moving images or still images. The display device 10 may refer to any electronic device that includes a display screen. Non-limiting examples of the display device 10 may include televisions, laptop computers, monitors, billboards, Internet of things (IoT) devices, mobile phones, smartphones, tablet personal computers (PCs), electronic watches, smart watches, watch phones, head mounted displays, mobile communication terminals, electronic notebooks, electronic books, portable multimedia players (PMPs), navigation devices, game machines, digital cameras, and camcorders, all of which provide a display screen.

The shape of the display device 10 can be variously modified. For example, the display device 10 may have various shapes such as a horizontally long rectangle, a vertically long rectangle, a square, a quadrilateral with rounded corners (vertices), other polygons, and a circle. The shape of a display area DA of the display device 10 may also be similar to the overall shape of the display device 10. FIG. 29 illustrates that each of the display device 10 and the display area DA has a shape of a horizontally long rectangle.

The display device 10 may include the display area DA and a non-display area NDA. The display area DA may be an area where an image can be displayed, and the non-display area NDA may be an area where no image is displayed. The display area DA may also be referred to as an active area, and the non-display area NDA may also be referred to as an inactive area.

The display area DA may generally occupy a center portion of the display device 10. The display area DA may include pixels PX. The pixels PX may be arranged in matrix directions. Each of the pixels PX may be rectangular or square in a plan view. However, the shape of each of the pixels PX is not limited thereto and may also be a rhombic shape having each side inclined with respect to a direction. Each of the pixels PX may include one or more light emitting elements 30 which emit light of a specific wavelength range to display a specific color.

Figure 30:
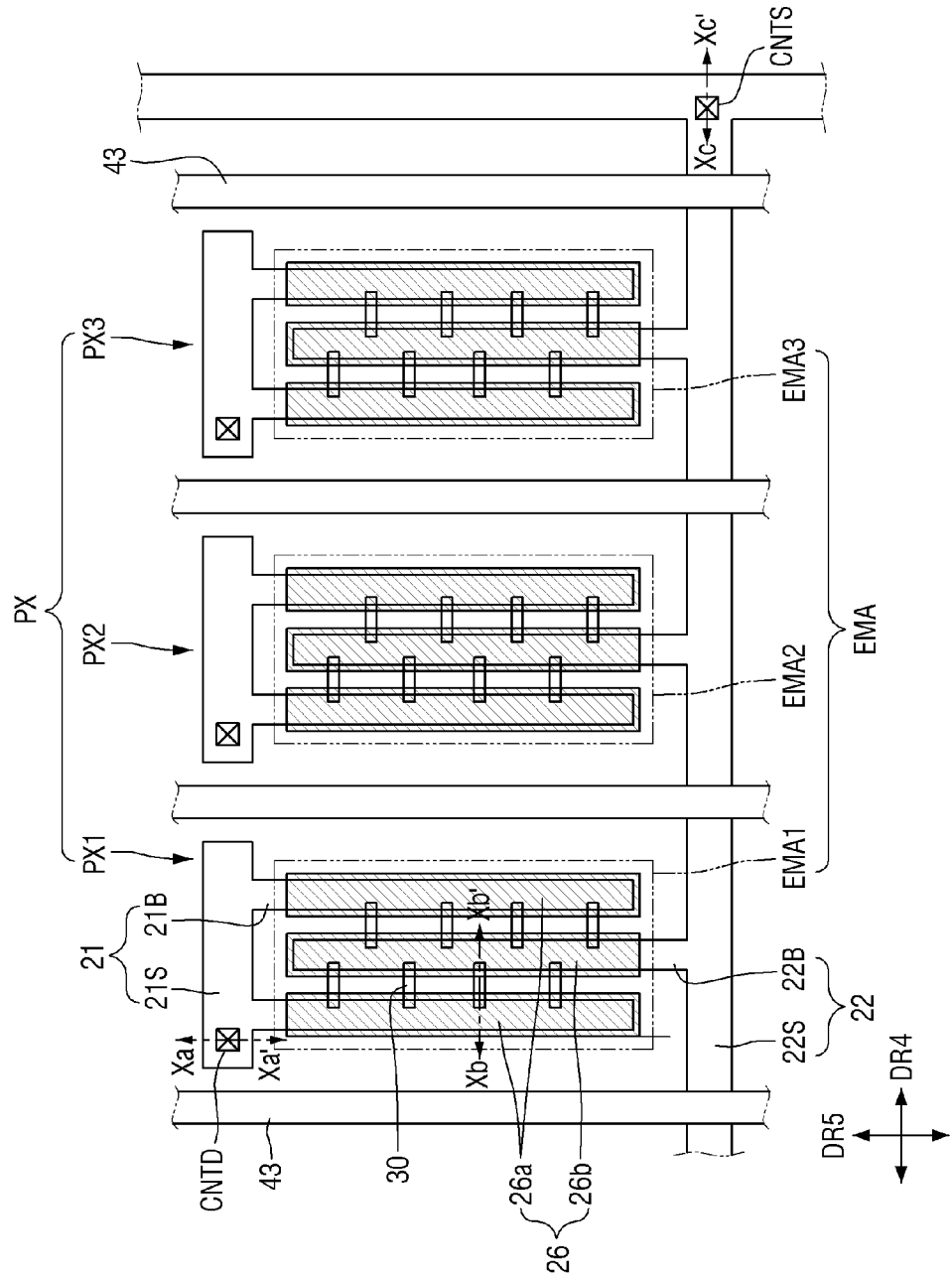
FIG. 30 is a schematic plan view of one pixel of a display device according to an embodiment.

FIG. 30 is a schematic plan view of a pixel of a display device according to an embodiment.

Referring to FIG. 30, each of the pixels PX may include a first sub-pixel PX1, a second sub-pixel PX2, and a third sub-pixel PX3. The first sub-pixel PX1 may emit light of a first color, the second sub-pixel PX2 may emit light of a second color, and the third sub-pixel PX3 may emit light of a third color. The first color may be blue, the second color may be green, and the third color may be red. However, the disclosure is not limited thereto, and each sub-pixel PXn may emit light of a same color (where n is a natural number). In addition, FIG. 30 illustrates that the pixel PX includes three sub-pixels PXn, but the disclosure is not limited thereto, and the pixel PX may include a greater number of sub-pixels PXn.

Each sub-pixel PXn of the display device 10 may include an area defined as an emission area EMA. The first sub-pixel PX1 may include a first emission area EMA1, the second sub-pixel PX2 may include a second emission area EMA2, and the third sub-pixel PX3 may include a third emission area EMA2. The emission area EMA may be defined as an area in which a light emitting element 30 included in the display device 10 is disposed to emit light in a specific wavelength range.

Although not illustrated in the drawing, each sub-pixel PXn of the display device 10 may include a non-emission area defined as the area other than the emission area EMA. The non-emission area may be an area where the light emitting element 30 is not disposed and light emitted from the light emitting element 30 does not reach, and thus light is not emitted therefrom.

Figure 31:
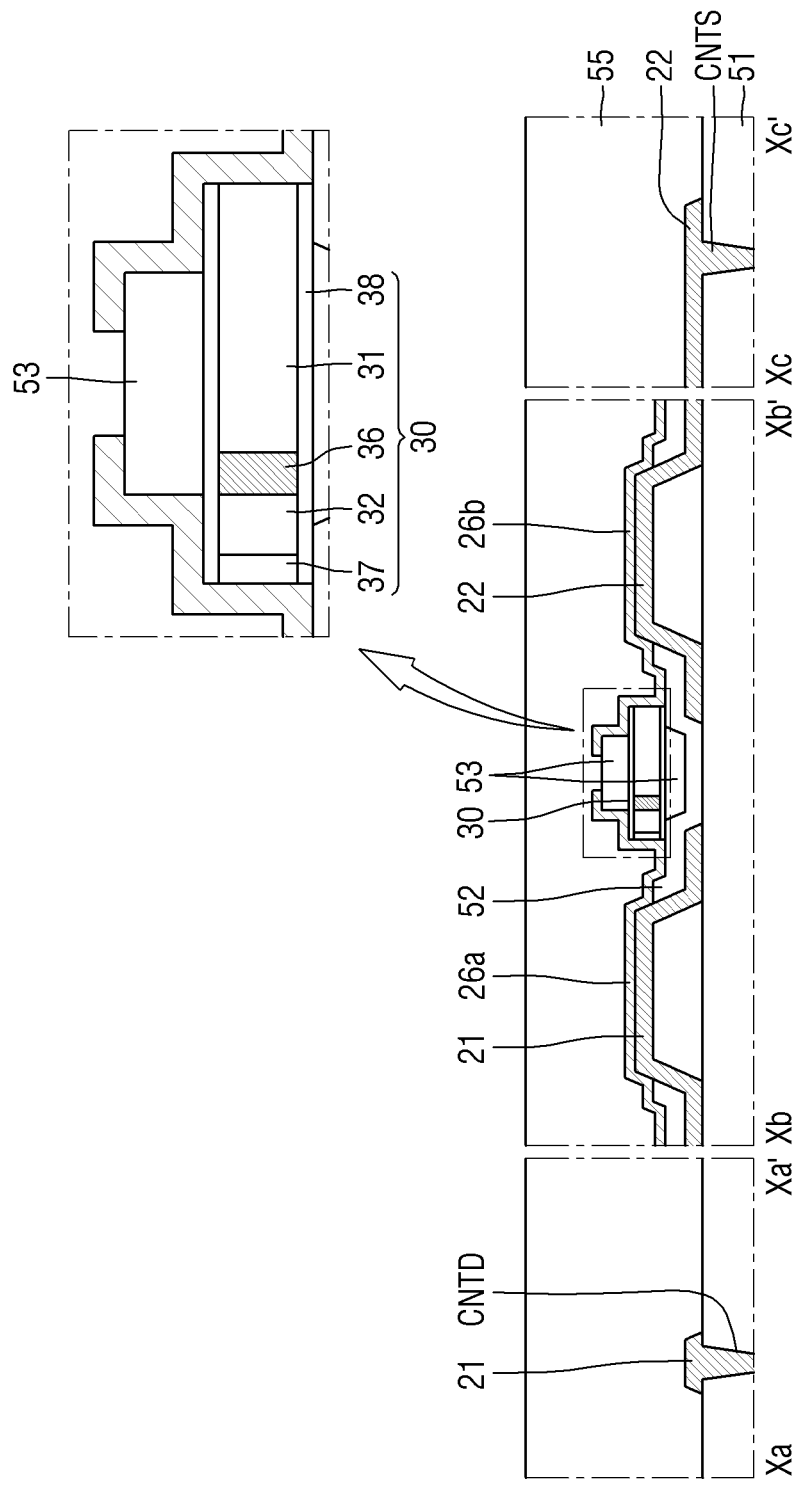
FIG. 31 is a schematic cross-sectional view taken along lines Xa-Xa', Xb-Xb', and Xc-Xc' of FIG. 30.

Each sub-pixel PXn of the display device 10 may include electrodes 21 and 22, the light emitting elements 30, contact electrodes 26, inner banks 41 and 42 (see FIG. 32), an outer bank 43, and at least one insulating layer 51, 52, 53, and 55 (see FIG. 31).

The electrodes 21 and 22 may be electrically connected to the light emitting elements 30 and may receive a voltage so that the light emitting elements 30 can emit light in a specific wavelength range. In addition, at least a portion of each of the electrodes 21 and 22 may be utilized to form an electric field in each sub-pixel PXn so as to align the light emitting elements 30.

The electrodes 21 and 22 may include a first electrode 21 and a second electrode 22. In an embodiment, the first electrode 21 may be a pixel electrode separated in each sub-pixel PXn, and the second electrode 22 may be a common electrode commonly connected along each sub-pixel PXn. One of the first electrode 21 and the second electrode 22 may be an anode electrode of the light emitting elements 30 and the other may be a cathode electrode of the light emitting elements 30. However, the disclosure is not limited thereto, and the opposite case may also be true.

The first electrode 21 and the second electrode 22 may include electrode stems 21S and 22S extended in a fourth direction DR4, respectively, and one or more electrode branches 21B and 22B branching off from the electrode stems 21S and 22S, respectively, and extended in a fifth direction DR5 intersecting the fourth direction DR4.

The first electrode 21 may include a first electrode stem 21S extended in the fourth direction DR4, and at least one first electrode branch 21B branching off from the first electrode stem 21S, and extended in the fifth direction DR5.

The first electrode stem 21S of an arbitrary pixel may have ends that are spaced apart from each other and terminated between the sub-pixels PXn, and may be substantially collinear with the first electrode stem 21S of a neighboring sub-pixel that belongs to a same row (e.g., is adjacent in the fourth direction DR4). The first electrode stem 21S disposed in each sub-pixel PXn may have ends spaced apart from each other, so that a different electrical signal can be applied to each first electrode branch 21B and the first electrode branches 21B can each be driven separately.

The first electrode branch 21B may branch off from at least a portion of the first electrode stem 21S, may be extended in the fifth direction DR5, and may be terminated while being spaced apart from a second electrode stem 22S that is disposed opposite to the first electrode stem 21S.

The second electrode 22 may include the second electrode stem 22S extended in the fourth direction DR4 and spaced apart from and facing the first electrode stem 21S in the fifth direction DR5, and a second electrode branch 22B branching off from the second electrode stem 22S and extended in the fifth direction DR5. Another end of the second electrode stem 22S may be connected to the second electrode stem 22S of another sub-pixel PXn adjacent in the fourth direction DR4. For example, unlike the first electrode stem 21S, the second electrode stem 22S may extend in the fourth direction DR4 and be disposed across each sub-pixel PXn. The second electrode stem 22S extending across each sub-pixel PXn may be connected to an outer portion of the display area DA in which each pixel PX or each sub-pixel PXn is disposed, or a portion extending from the non-display area NDA in a direction.

The second electrode branch 22B may be spaced apart from and facing the first electrode branch 21B, and may be terminated while being spaced apart from the first electrode stem 21S. The second electrode branch 22B may be connected to the second electrode stem 22S and an end thereof in the extending direction may be disposed within the sub-pixel PXn while being spaced apart from the first electrode stem 21S.

The first electrode 21 and the second electrode 22 may be electrically connected to a circuit element layer of the display device 10 through contact holes, e.g., a first electrode contact hole CNTD and a second electrode contact hole CNTS, respectively. FIG. 30 illustrates that the first electrode contact hole CNTD is formed in every first electrode stem 21S of each sub-pixel PXn and a second electrode contact hole CNTS is formed in a second electrode stem 22S extending across each of the sub-pixels PXn. However, the disclosure is not limited thereto, and in some embodiments, the second electrode contact hole CNTD may be formed in each sub-pixel PXn.

The outer bank 43 may be disposed at the boundary between the sub-pixels PXn, and the inner banks 41 and 42 may be disposed adjacent to the center of each sub-pixel PXn and may be disposed under the electrodes 21 and 22, respectively. Although the inner banks 41 and 42 are not illustrated in the drawing, a first inner bank 41 and a second inner bank 42 may be disposed under the first electrode stem 21B and the second electrode stem 22B, respectively.

The outer bank 43 may be disposed at the boundary between the sub-pixels PXn. First electrode stems 21S may have ends that are spaced apart from each other with respect to the outer bank 43 and may be terminated. The outer bank 43 may extend in the fifth direction DR5 and be disposed at the boundary between the sub-pixels PXn arranged in the fourth direction DR4. However, the disclosure is not limited thereto, and the outer bank 43 may extend in the fourth direction DR4 and may also be disposed at the boundary between the sub-pixels PXn arranged in the fifth direction DR5. The outer bank 43 and the inner banks 41 and 42 may include a same material, and thus may be simultaneously formed by a process.

The light emitting elements 30 may be disposed between the first electrode 21 and the second electrode 22. One end of the light emitting elements 30 may be electrically connected to the first electrode 21, and another end may be electrically connected to the second electrode 22. The light emitting elements 30 may be electrically connected to each of the first electrode 21 and the second electrode 22 via the contact electrodes 26 which will be described in more detail below.

The light emitting elements 30 may be disposed to be spaced apart from each other and may be aligned to be substantially parallel to each other. A distance by which the light emitting elements 30 are spaced apart from each other is not particularly limited. In some embodiments, some of the light emitting elements 30 may be disposed close to each other to form a group, and some other of the light emitting elements 30 may be disposed close to each other to form another group while are spaced apart from the group. As another example, the light emitting elements 30 may be arranged such that they are orientated in a direction with non-uniform density. In addition, in an embodiment, the light emitting elements 30 may have a shape extending in a direction, and the direction in which each electrode, e.g., the first electrode branch 21B and the second electrode branch 22B may be substantially perpendicular to the direction in which the light emitting elements 30 extend. However, the disclosure is not limited thereto, and the light emitting elements 30 may not be perpendicular but may be oblique to the direction in which the first electrode branch 21B and the second electrode branch 22B extend.

The light emitting elements 30 according to an embodiment may include active layers 36 including different materials to emit light in different wavelength ranges. In the display device 10, each light emitting element 30 of the first sub-pixel PX1 may emit first light of which the central wavelength band is a first wavelength, each light emitting element 30 of the second sub-pixel PX2 may emit second light whose central wavelength band is a second wavelength, and each light emitting element 30 of the third sub-pixel PX3 may emit third light whose central wavelength band is a third wavelength. Accordingly, the first light may be output from the first sub-pixel PX1, the second light may be output from the second sub-pixel PX2, and the third light may be output from the third sub-pixel PX3. In some embodiments, the first light may be blue color light whose central wavelength band is in a range of about 450 nm to about 495 nm, the second light may be green color light of which the central wavelength band is in a range of about 495 nm to about 570 nm, and the third light may be red color light whose central wavelength band is in a range of about 620 nm to about 750 nm. However, the disclosure is not limited thereto.

Although not illustrated in FIG. 30, the display device 10 may include a second insulating layer 52 that covers at least a portion of the first electrode 21 and the second electrode 22.

The second insulating layer 52 may be disposed in each sub-pixel PXn of the display device 10. The second insulating layer 52 may be disposed to substantially cover the entire area of each sub-pixel PXn, and may also be extended to other adjacent sub-pixels PXn. The second insulating layer 52 may be disposed to cover at least a portion of the first electrode 21 and the second electrode 22. The second insulating layer 52 may be disposed to expose a portion of the first electrode 21 and the second electrode 22, specifically, a portion of the first electrode branch 21B and the second electrode branch 22B.

The contact electrodes 26 may each have a shape in which at least a part thereof extends in a direction. Each of the contact electrodes 26 may contact the light elements 30 and the electrodes 21 and 22, and the light emitting elements 30 may receive electrical signals from the first electrode 21 and the second electrode 22 via the contact electrodes 26.

The contact electrodes 26 may include a first contact electrode 26a and a second contact electrode 26b. The first contact electrode 26a and the second contact electrode 26b may be disposed on the first electrode branch 21B and the second electrode branch 22B, respectively.

The first contact electrode 26a may be disposed on the first electrode 21 or the first electrode branch 21B and extend in the fifth direction DR5. The first contact electrode 26a may contact one end of the light emitting element 30. Also, the first contact electrode 26a may contact the first electrode 21 exposed due to the second insulating layer 52 not being disposed thereon. As a result, the light emitting elements 30 may be electrically connected to the first electrode 21 through the first contact electrode 26a.

The second contact electrode 26b may be disposed on the second electrode 22 or the second electrode branch 22B and extend in the fifth direction DR5. The second contact electrode 26b may be spaced apart from the first contact electrode 26a in the fourth direction DR4. The second contact electrode 26b may contact another end of the light emitting elements 30. Also, the second contact electrode 26b may contact the second electrode 22 exposed due to the second insulating layer 52 not being disposed thereon. Accordingly, the light emitting elements 30 may be electrically connected to the second electrode 22 through the second contact electrode 26b. Although FIG. 30 illustrates that two first contact electrodes 26a and a second contact electrode 26b are disposed in a sub-pixel PXn, the disclosure is not limited thereto. The number of first contact electrodes 26a and second contact electrodes 26b may vary according to the number of first electrodes 21 and second electrodes 22 disposed in each sub-pixel PXn, or the number of first electrode branches 21B and second electrode branches 22B.

In some embodiments, a width of each of the first contact electrode 26a and the second contact electrode 26b measured in a direction may be greater than a width of each of the first electrode 21 and the second electrode 22, or a width of each of the first electrode branch 21B and the second electrode branch 22B, measured in the direction. However, the disclosure is not limited thereto, and in some embodiments, the first contact electrode 26a and the second contact electrode 26b may be disposed to cover at least a side portion of the first electrode branch 21B or the second electrode branch 22B.

The display device 10 may include a circuit element layer located under each of the electrodes 21 and 22, a third insulating layer 53 (see FIG. 31) disposed to cover at least a part of each of the electrodes 21 and 22 and the light emitting elements 30, and a passivation layer 55 (see FIG. 31), in addition to the second insulating layer 52. Hereinafter, the structure of the display device 10 will be described in detail with reference to FIG. 31.

FIG. 31 is a schematic cross-sectional view taken along lines Xa-Xa', Xb-Xb', and Xc-Xc' of FIG. 30.

FIG. 31 illustrates a schematic cross-sectional view of the first sub-pixel PX1, but the following description of the first sub-pixel PX1 may also be applicable to other pixels PX or other sub-pixels PXn. FIG. 31 illustrates a schematic cross-sectional view taken along line that extends from one end to another end of a light emitting element 30 disposed in the first sub-pixel PX1.

Although not illustrated in FIG. 31, the display device 10 may further include the circuit element layer disposed under each of the electrodes 21 and 22. The circuit element layer may include semiconductor layers and conductive patterns and may include at least one transistor and a power line. However, hereinafter, detailed description thereof will be omitted.

Referring to FIGS. 30 and 31, the display device 10 may include a first insulating layer 51, the electrodes 21 and 22 disposed on the first insulating layer 51, the light emitting elements 30, and the like. A circuit element layer (not shown) may be further disposed under the first insulating layer 51. The first insulating layer 51 may include an organic insulating material and perform a surface planarization function.

The inner banks 41 and 42, the outer bank 43, the electrodes 21 and 22, and the light emitting element 30 may be disposed on the first insulating layer 51.

In case that ink in which the light emitting elements 30 are dispersed is sprayed by using the above-described inkjet printing device 1000 of FIG. 1 during manufacture of the display device 1, the outer bank 43 may serve to prevent or reduce the ink from flowing over the boundary between the sub-pixels PXn. The outer bank 43 may separate inks, in which different light emitting elements 30 are dispersed for each sub-pixel PXn, from each other not to be mixed with each other. However, the disclosure is not limited thereto.

The inner banks 41 and 42 may include first and second inner banks 41 and 42 that are disposed adjacent to the center of each sub-pixel PXn.

The first inner bank 41 and the second inner bank 42 may be disposed to be spaced apart from and face each other. The first electrode 21 may be disposed on the first inner bank 41, and the second electrode 22 may be disposed on the second inner bank 42. Referring to FIGS. 30 and 31, it may be understood that the first electrode branch 21B is disposed on the first inner bank 41 and the second electrode branch 22B is disposed on the second inner bank 42.

The first inner bank 41 and the second inner bank 42 may extend in the fifth direction DR5 within each sub-pixel PXn. However, the disclosure is not limited thereto, and the first inner bank 41 and the second inner bank 42 may be disposed in each sub-pixel PXn to form a pattern on the entire surface of the display device 10. The inner banks 41 and 42 and the outer banks 43 may include polyimide (PI), but are not limited thereto.

The first inner bank 41 and the second inner bank 42 may have a structure in which at least a part thereof protrudes from the first insulating layer 51. The first inner bank 41 and the second inner bank 42 may each have a structure in which at least a part thereof protrudes upward from the plane on which the light emitting element 30 is disposed, and at least a part of the protruding portion may be inclined. Since the inner banks 41 and 42 have the side surface protruding and inclined with respect to the first insulating layer 51, the light emitted from the light emitting element 30 may be reflected from the inclined side surfaces of the inner banks 41 and 42. As will be described below, in case that the electrodes 21 and 22 disposed on the inner banks 41 and 42 include a highly reflective material, the light emitted from the light emitting element 30 may be reflected from the electrodes 21 and 22 and may travel in an upward direction of the first insulating layer 51.

The outer bank 43 may be disposed along the boundary between the sub-pixels PXn to form a lattice pattern, whereas the inner banks 41 and 42 may be disposed in each sub-pixel PX1 to extend in a direction.

The electrodes 21 and 22 may be disposed on the first insulating layer 51 and the inner banks 41 and 42. As described above, the electrode 21 includes the electrode stem 21S and the electrode branch 21B, and the electrode 22 includes the electrode stem 22S and the electrode branch 22B.

Parts of the first and second electrodes 21 and 22 may be disposed on the first insulating layer 51 and parts of the first and second electrodes 21 and 22 may be disposed on the first inner bank 41 and the second inner bank 42, respectively. As described above, the first and second electrode stems 21S and 22S of the first and second electrodes 21 and 22 may extend in the fourth direction DR4, and the first and second inner banks 41 and 42 may extend in the fifth direction DR5 to be disposed even in the sub-pixels PXn adjacent in the fifth direction DR5.

A first electrode contact hole CNTD may be formed in the first electrode stem 21S of the first electrode 21 to penetrate the first insulating layer 51 and thus to expose a part of the circuit element layer. The first electrode 21 may be electrically connected to a transistor of the circuit element layer through the first electrode contact hole CNTD. The first electrode 21 may receive an electrical signal from the transistor.

The second electrode stem 22S of the second electrode 22 may extend in a direction to be disposed even in the non-emission area where the light emitting elements 30 are not disposed. A second electrode contact hole CNTS may be formed in the second electrode stem 22S to penetrate the first insulating layer 51 and thus to expose a part of the circuit element layer. The second electrode 22 may be electrically connected to a power supply electrode through the second electrode contact hole CNTS. The second electrode 22 may receive an electrical signal from the power supply electrode.

Parts of the first and second electrodes 21 and 22, e.g., the first and second electrode branches 21B and 22B, may be disposed on the first inner bank 41 and the second inner bank 42, respectively. Light emitting elements 30 may be disposed in the region between the first and second electrodes 21 and 22, for example, the region where the first and second electrode branches 21B and 22B are spaced apart from and facing each other.

Each of the electrodes 21 and 22 may include a transparent conductive material. For example, each of the electrodes 21 and 22 may include a material such as indium tin oxide (ITO), indium zinc oxide (IZO), and/or indium tin zinc Oxide (ITZO), but is not limited thereto. In some embodiments, for example, each of the electrodes 21 and 22 may include a metal such as silver (Ag), copper (Cu), aluminum (Al), or the like, as a highly reflective material. In this case, light incident on each of the electrodes 21 and 22 may be reflected and thus be emitted in an upward direction of each sub-pixel PXn.

In addition, each of the first and second electrodes 21 and 22 may have a structure in which one or more layers including a transparent conductive material and a metal with a high reflectivity are stacked or may include a single layer containing both a transparent conductive material and a metal with a high reflectivity. In an embodiment, each of the first and second electrodes 21 and 22 may have a stack of ITO/Ag/ITO/IZO or may include an alloy of Al, nickel (Ni), lanthanum (La), or the like. However, the disclosure is not limited thereto.

The second insulating layer 52 is disposed on the first insulating layer 51 and on the first and second electrodes 21 and 22. The second insulating layer 52 is disposed to partially cover the first and second electrodes 21 and 22. The second insulating layer 52 may be disposed to cover most of the upper surface of each of the first and second electrodes 21 and 22, but may expose parts of the first and second electrodes 21 and 22. The second insulating layer 52 may be disposed to expose parts of the upper surface of the first and second electrodes 21 and 22, for example, the upper surfaces of the first and second electrode branches 21B and 22B, which are disposed on the first and second inner banks 410 and 420, respectively. For example, the second insulating layer 52 may be formed on substantially the entire area of the first insulating layer 51, but may include openings that expose parts of the first and second electrodes 21 and 22.

In an embodiment, the second insulating layer 52 may have a step (or height difference) so that portions of the upper surfaces of the first and second electrodes 21 and 22 are recessed between the first and second electrodes 21 and 22. In some embodiments, the second insulating layer 52 may include an inorganic insulating material, and a portion of the upper surface of the second insulating layer 52, which covers the first and second electrodes 21 and 22, may be recessed due to a step of a member disposed under the second insulating layer 52. The light emitting element 30 on the second insulating layer 52 between the first electrode 21 and the second electrode 22 and the recessed upper surface of the second insulating layer 52 may form an empty space therebetween. The light emitting element 30 may be partially spaced apart from the upper surface of the second insulating layer 52, and the empty space may be filled with a material that forms a third insulating layer 53 which will be described in more detail below. However, the disclosure is not limited thereto. The second insulating layer 52 may form a substantially flat upper surface so as to allow the light emitting element 30 to be disposed thereon.

The second insulating layer 52 may not only protect the first electrode 21 and the second electrode 22 but also insulate them from each other. Further, the second insulating layer 52 may prevent or reduce damage to the light emitting element 30 thereon from directly contacting other members. However, the shape and structure of the second insulating layer 52 are not limited thereto.

The light emitting element 30 may be disposed on the second insulating layer 52 between the electrodes 21 and 22. For example, at least one light emitting element 30 may be disposed on the second insulating layer 52 disposed between the electrode branches 21B and 22B. However, the disclosure is not limited thereto. Although not illustrated, at least some of the light emitting elements 30 disposed within each sub-pixel PXn may be disposed in an area other than the area between the electrode branches 21B and 22B. The light emitting elements 30 may be disposed in an area where the first electrode branch 21B and the second electrode branch 22B face each other, and may be electrically connected to each of the electrodes 21 and 22 via the contact electrodes 26.

The light emitting element 30 may include layers arranged horizontally on the first insulating layer 51. The light emitting element 30 of the display device 10 according to an embodiment may have a shape extending in a direction and may have a structure in which semiconductor layers are sequentially arranged in a direction. As described above, the first semiconductor layer 31, the active layer 36, the second semiconductor layer 32, and the electrode layer 37 may be sequentially disposed in a direction in the light emitting element 30, and the insulating layer 38 may surround the outer surface of the stack of the first semiconductor layer 31, the active layer 36, the second semiconductor layer 32, and the electrode layer 37. The direction in which the light emitting element 30 disposed in the display device 10 extends may be parallel to the first insulating layer 51, and the semiconductor layers of the light emitting element 30 may be sequentially arranged in a direction parallel to the upper surface of the first insulating layer 51. However, the disclosure is not limited thereto. In some embodiments, in case that the light emitting element 30 has a different structure, the layers may be arranged perpendicular to the first insulating layer 51.

In addition, one end of the light emitting element 30 may contact the first contact electrode 26a and another end may contact the second contact electrode 26b. According to an embodiment, since the insulating layer 38 is not formed at the extended ends of the light emitting element 30 and thus the ends of the light emitting element 30 are exposed, the exposed ends may be electrically connected to the first contact electrode 26a and the second contact electrode 26b. However, the disclosure is not limited thereto. In some embodiments, the insulating layer 38 may be partially removed from the light emitting element 30 so that side surfaces at ends of the light emitting element 30 may be exposed.

The third insulation layer 53 may be disposed, in part, on the light emitting element 30 which is disposed between the first electrode 21 and the second electrode 22. The third insulating layer 53 may be disposed to partially surround an outer surface of the light emitting element 30. The third insulating layer 53 may not only protect the light emitting element 30, but also fix the light emitting element 30 during manufacture of the display device 10. In addition, in an embodiment, a portion of the material of the third insulating layer 53 may be disposed between the bottom surface of the light emitting element 30 and the second insulating layer 52. As described above, the third insulating layer 53 may be formed to fill the empty space formed between the second insulating layer 52 and the light emitting element 30 during manufacture of the display device 10. Accordingly, the third insulating layer 53 may be formed to surround the outer surface of the light emitting element 30. However, the disclosure is not limited thereto.

The third insulating layer 53 may extend in the fifth direction DR5 between the first electrode branch 21B and the second electrode branch 22B in a plan view. For example, the third insulating layer 53 may have an island shape or a linear shape on the first insulating layer 51 in a plan view. According to an embodiment, the third insulating layer 53 may be disposed above the light emitting element 30.

The first contact electrode 26a and the second contact electrode 26b are disposed on the electrodes 21 and 22, respectively, and on the third insulating layer 53. The first contact electrode 26a and the second contact electrode 26b may be disposed to be spaced apart from each other on the third insulating layer 53. The third insulating layer 53 may insulate the first contact electrode 26a and the second contact electrode 26b from each other so that the first contact electrode 26a and the second contact electrode 26b directly contact each other.

The first contact electrode 26a may contact the exposed portion of the first electrode 21 on the first inner bank 41, and the second contact electrode 26b may contact the exposed portion of the second electrode 22 on the second inner bank 42. The first contact electrode 26a and the second contact electrode 26b may transmit an electrical signal, transmitted from each of the electrodes 21 and 22, to the light emitting element 30.

The contact electrodes 26 may include a conductive material. For example, the material may include ITO, IZO, ITZO, aluminum (Al), and the like. However, the disclosure is not limited thereto.

The passivation layer 55 may be disposed on the contact electrodes 26 and the third insulating layer 53. The passivation layer 55 may function to protect members, disposed on the first insulating layer 51, from the external environment.

Each of the second insulating layer 52, the third insulating layer 53, and the passivation layer 55 described above may include an inorganic insulating material or an organic insulating material. In an embodiment, each of the second insulating layer 52, the third insulating layer 53, and the passivation layer 55 may include an inorganic insulating material, such as silicon oxide ($SiO_x$), silicon nitride ($SiN_x$), silicon oxynitride ($SiO_xN_y$), aluminum oxide ($Al_2O_3$), or aluminum nitride (AlN). Further, each of the second insulating layer 52, the third insulating layer 53, and the passivation layer 55 may include an organic insulating material, such as acrylic resin, epoxy resin, phenolic resin, polyamide resin, polyimide resin, unsaturated polyester resin, polyphenylene resin, polyphenylene sulfide resin, benzocyclobutene, cardo resin, siloxane resin, silsesquioxane resin, polymethyl methacrylate, polycarbonate, or polymethyl methacrylate-polycarbonate synthetic resin. However, the disclosure is not limited thereto.

Figure 32:
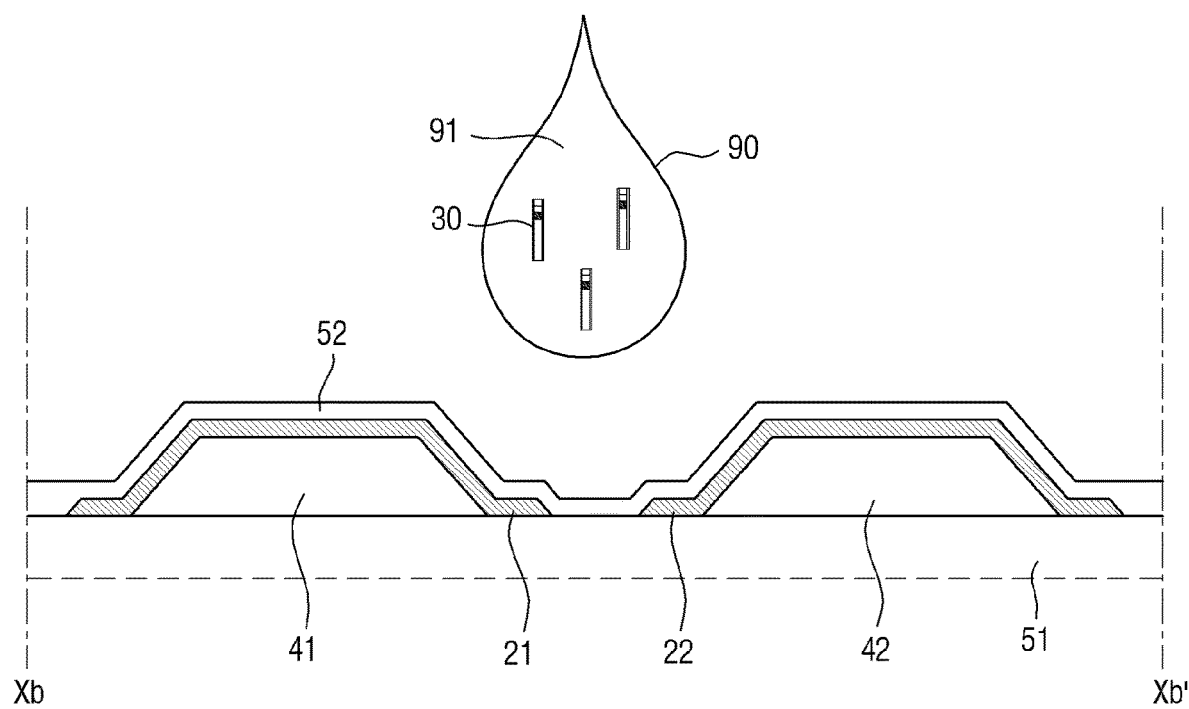
FIGS. 32 to 34 are schematic cross-sectional views illustrating a part of a method of manufacturing a display device according to an embodiment.
Figure 33:
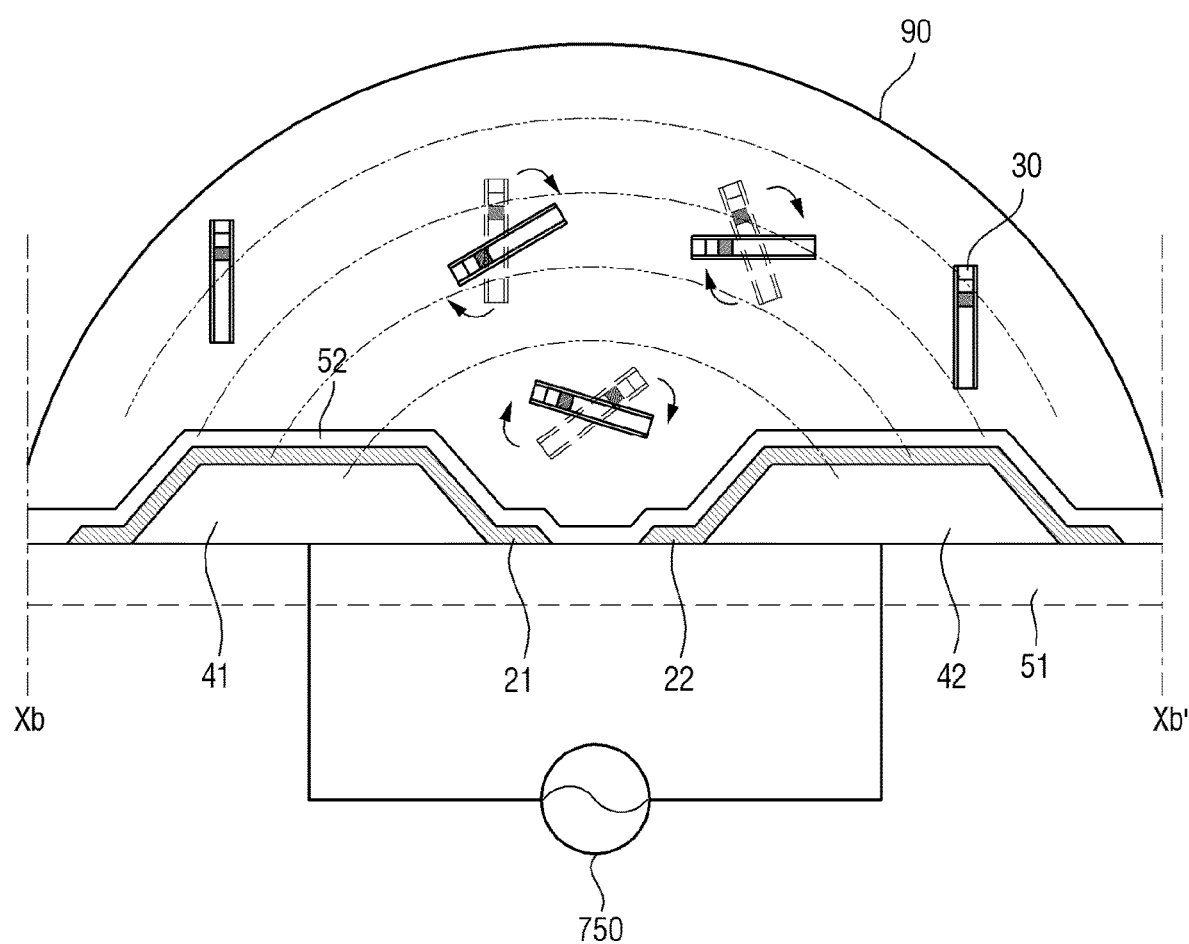
Figure 34:
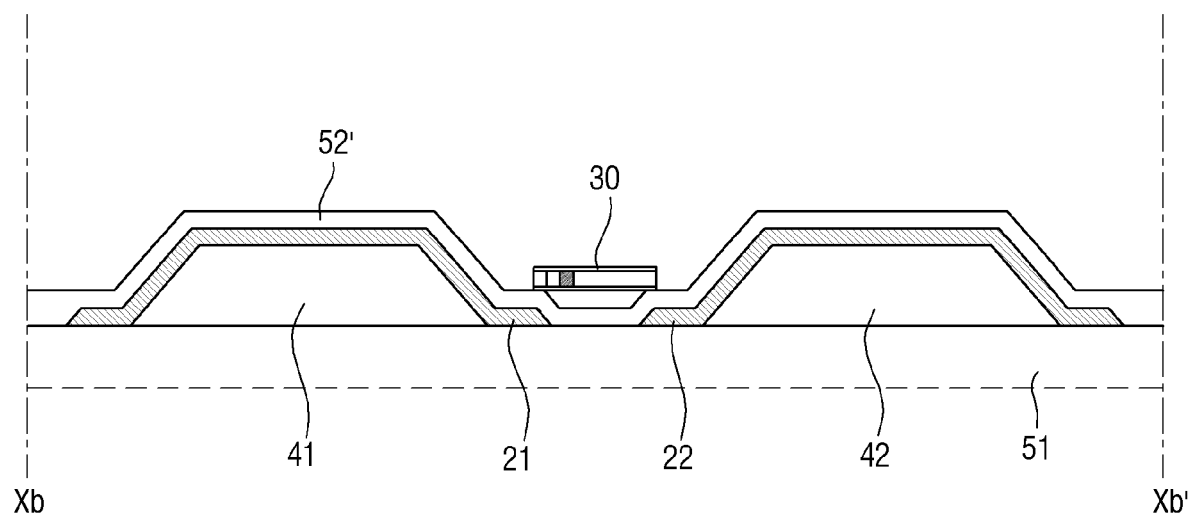

FIGS. 32 to 34 are schematic cross-sectional views illustrating a part of a method of manufacturing a display device according to an embodiment.

Referring to FIGS. 32 to 34, a display device 10 according an embodiment may be manufactured using the inkjet printing device 1000 described above with reference to FIG. 1. The inkjet printing device 1000 may spray ink 90 in which light emitting elements 30 are dispersed, and the light emitting elements 30 may be disposed between a first electrode 21 and a second electrode 22 of the display device 10.

First, as shown in FIG. 32, a first insulating layer 51, a first inner bank 41 and a second inner bank 42 that are spaced apart from each other on the first insulating layer 51, the first electrode 21 and the second electrode 22 that are disposed on the first inner bank 41 and the second inner bank 42, respectively, and a second insulating material layer 52' that covers the first electrode 21 and the second electrode 22 are prepared. A part of the second insulating material layer 52' may be patterned in a subsequent process to form a second insulating layer 52 of the display device 10. The above members may be formed by patterning a metal, an inorganic material, or an organic material by using a suitable mask process.

Thereafter, the ink 90 in which the light emitting elements 30 are dispersed is sprayed onto the first electrode 21 and the second electrode 22. The light emitting element 30 is a type of bipolar element, and the ink 90 in which the light emitting elements 30 are dispersed may be sprayed by using the inkjet printing device 1000 and the printing method of a bipolar element described above. As shown in the drawing, the inkjet printing device 1000 according to an embodiment may eject the ink 90 while maintaining a uniform number of light emitting elements 30 in the ink 90. A description thereof is substantially identical to that given above, and thus a detailed description thereof will not be provided.

As shown in FIG. 33, by applying an electric signal to the first electrode 21 and the second electrode 22, an electric field IEL is provided to the ink 90 in which the light emitting element 30 is dispersed. As a dielectrophoretic force is transmitted due to the electric field IEL and an orientation direction and position of the light emitting element 30 are changed, the light emitting elements may be mounted between the first electrode 21 and the second electrode 22.

As shown in FIG. 34, a solvent 91 of the ink 90 is removed. Through the above process, the light emitting elements 30 may be disposed between the first electrode 21 and the second electrode 22. Thereafter, although not illustrated in the drawing, the second insulating material layer 52' may be patterned to form the second insulating layer 52, and a third insulating layer 53, a first contact electrode 26a, a second contact electrode 26b, and a passivation layer 55 may be formed to manufacture the display device 10.

The shape and material of the light emitting element 30 are not limited to those described with reference to FIG. 28. In some embodiments, the light emitting element 30 may include a greater number of layers, or may have a different shape.

Figure 35:
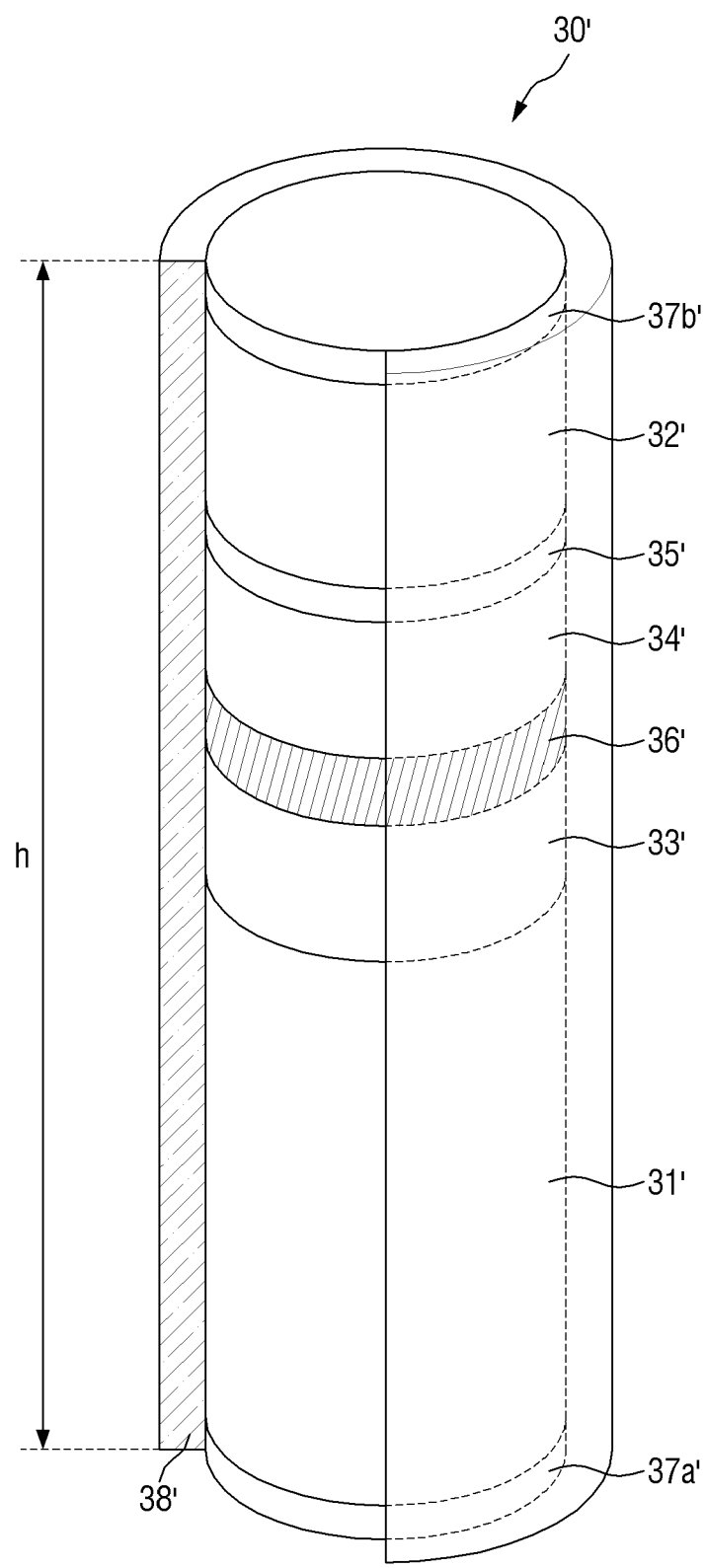
FIGS. 35 and 36 are schematic diagrams illustrating a light emitting element according to another embodiment.
Figure 36:
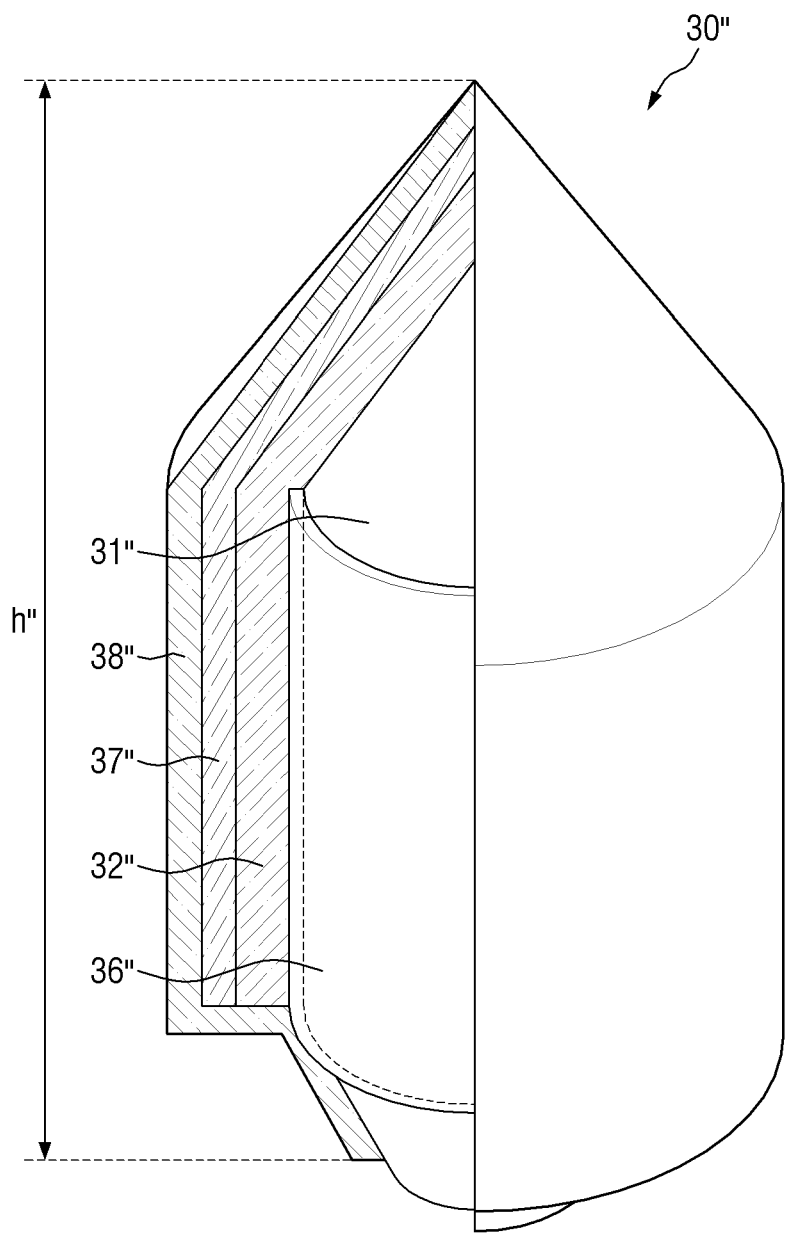

FIGS. 35 and 36 are schematic diagrams illustrating a light emitting element according to another embodiment.

First, referring to FIG. 35, a light emitting element 30' according to an embodiment may further include a third semiconductor layer 33' disposed between a first semiconductor layer 31' and an active layer 36', and a fourth semiconductor layer 34' and a fifth semiconductor layer 35' disposed between the active layer 36' and a second semiconductor layer 32'. The light emitting element 30' of FIG. 35 is different from that of the embodiments of FIG. 28 in that semiconductor layers 33', 34', and 35' and electrode layers 37a' and 37b' are further disposed, and the active layer 36' contains other elements. Other than the difference described above, the arrangement and structure of the insulating layer 38' is substantially the same as that in FIG. 28. FIG. 35 illustrates that some of the members are the same as those of FIG. 28, but new reference numerals are denoted for convenience of description. Hereinafter, redundant descriptions will be omitted and the following description will focus on differences.

As described above, in the light emitting element 30 of FIG. 28, the active layer 36 may include nitrogen (N) to emit blue color or green color light. In the light emitting element 30' of FIG. 35, the active layer 36' and other semiconductor layers may each be a semiconductor including at least phosphorus (P). For example, the light emitting element 30' according to an embodiment may emit red color light having a central wavelength band of about 620 nm to about 750 nm. However, it should be understood that the central wavelength band of red color light is not limited to the above-described range, and includes all wavelength ranges that may be recognized as a red color in the art.

Specifically, the first semiconductor layer 31' is an n-type semiconductor layer, and in case that the light emitting element 30' emits red color light, the first semiconductor layer 31' may include a semiconductor material having a chemical formula of $In_xAl_yGa_{1-x-y}P$ ($0 \leq x \leq 1$, $0 \leq y \leq 1$, $0 \leq x+y \leq 1$). For example, the first semiconductor layer 31' may be any one or more of n-type doped InAlGaP, GaP, AlGaP, InGaP, AlP, and InP. The first semiconductor layer 31' may be doped with an n-type dopant, and for example, the n-type dopant may be Si, Ge, Sn, or the like. In an embodiment, the first semiconductor layer 31' may be n-AlGaInP doped with n-type Si. A length of the first semiconductor layer 31' may be in a range of about 1.5 um to about 5 um, but is not limited thereto.

The second semiconductor layer 32' is a p-type semiconductor layer, and in case that the light emitting element 30' emits red color light, the second semiconductor layer 32' may include a semiconductor material having a chemical formula of $In_xAl_yGa_{1-x-y}P$ ($0 \leq x \leq 1$, $0 \leq y \leq 1$, $0 \leq x+y \leq 1$). For example, the second semiconductor layer 32' may be one or more of p-type doped InAlGaP, GaP, AlGaNP, InGaP, AlP, and InP. The second semiconductor layer 32' may be doped with a p-type dopant, and for example, the p-type dopant may be Mg, Zn, Ca, Se, Ba, or the like. In an embodiment, the second semiconductor layer 32' may be p-GaP doped with p-type Mg. A length of the second semiconductor layer 32' may be in a range of about 0.08 um to about 0.25 um, but is not limited thereto.

The active layer 36' may be disposed between the first semiconductor layer 31' and the second semiconductor layer 32'. As in the active layer 36 of FIG. 28, the active layer 36' of FIG. 35 may also emit light of a specific wavelength band by including a material having a single or multiple quantum well structure. For example, in case that the active layer 36' emits light in a red wavelength band, the active layer 36' may include a material, such as AlGaP or AlInGaP. Particularly, in case that the active layer 36' has a structure in which quantum layers and well layers are alternately stacked in a multiple quantum well structure, the quantum layer may include a material, such as AlGaP or AlInGaP, and the well layer may include a material, such as GaP or AlInP. In an embodiment, the active layer 36' may emit red color light having a central wavelength band of about 620 nm to about 750 nm by including AlGaInP as the quantum layer and AlInP as the well layer.

The light emitting element 30' of FIG. 35 may include a cladding layer disposed adjacent to the active layer 36'. As shown in the drawing, the third semiconductor layer 33' and the fourth semiconductor layer 34' disposed between the first semiconductor layer 31' and the second semiconductor layer 32' above and below the active layer 36' may be cladding layers.

The third semiconductor layer 33' may be disposed between the first semiconductor layer 31' and the active layer 36'. The third semiconductor layer 33' may be an n-type semiconductor, similar to the first semiconductor layer 31', and for example, the third semiconductor layer 33' may include a semiconductor material having a chemical formula of $In_xAl_yGa_{1-x-y}P$ ($0 \leq x \leq 1$, $0 \leq y \leq 1$, $0 \leq x+y \leq 1$). In an embodiment, the first semiconductor layer 31' may be n-AlGaInP, and the third semiconductor layer 33' may be n-AlInP. However, the disclosure is not limited thereto.

The fourth semiconductor layer 34' may be disposed between the active layer 36' and the second semiconductor layer 32'. The fourth semiconductor layer 34' may be an n-type semiconductor, similar to the second semiconductor layer 32', and for example, the fourth semiconductor layer 34' may include a semiconductor material having a chemical formula of $In_xAl_yGa_{1-x-y}P$ ($0 \leq x \leq 1$, $0 \leq y \leq 1$, $0 \leq x \leq 1$). In an embodiment, the second semiconductor layer 32' may be p-GaP, and the fourth semiconductor layer 34' may be p-AlInP.

The fifth semiconductor layer 35' may be disposed between the fourth semiconductor layer 34' and the second semiconductor layer 32'. The fifth semiconductor layer 35' may be a p-type doped semiconductor like the second semiconductor layer 32' and the fourth semiconductor layer 34'. In some embodiments, the fifth semiconductor layer 35' may function to reduce a difference in lattice constant between the fourth semiconductor layer 34' and the second semiconductor layer 32'. For example, the fifth semiconductor layer 35' may be a tensile strain barrier reducing (TSBR) layer. For example, the fifth semiconductor layer 35' may include p-GaInP, p-AlInP, or p-AlGaInP, but is not limited thereto. In addition, lengths of the third semiconductor layer 33', the fourth semiconductor layer 34', and the fifth semiconductor layer 35' may be in a range of about 0.08 um to about 0.25 um, but are not limited thereto.

A first electrode layer 37a' a and a second electrode layer 37b' may be disposed on the first semiconductor layer 31' and the second semiconductor layer 32', respectively. The first electrode layer 37a' may be disposed on a lower surface of the first semiconductor layer 31', and the second electrode layer 37b' may be disposed on an upper surface of the second semiconductor layer 32'. However, the disclosure is not limited thereto, and at least one of the first electrode layer 37a' and the second electrode layer 37b' may be omitted. For example, in the light emitting element 30', the first electrode layer 37a' may not be disposed on the lower surface of the first semiconductor layer 31', while only the second electrode layer 37b' is disposed on the upper surface of the second semiconductor layer 32'.

Referring to FIG. 36, a light emitting element 30" may have a shape extending in a direction and having a partially inclined side surface. For example, the light emitting element 30" according to an embodiment may have a partially conical shape.

The light emitting element 30" may be formed such that layers are not stacked in a direction, and each of the layers surrounds an outer surface of another layer. The light emitting element 30" of FIG. 36 may be formed such that semiconductor layers surround at least a portion of an outer surface of another layer. The light emitting element 30" may include a semiconductor core, of which at least a portion partially extends in a direction, and an insulating layer 38" formed to surround the semiconductor core. The semiconductor core may include a first semiconductor layer 31", an active layer 36", a second semiconductor layer 32", and an electrode layer 37". The light emitting element 30" of FIG. 36 is the same as the light emitting element 30 of FIG. 28 except that shapes of the constituting layers are partially different. The light emitting element 30" may have a length h" in a range of about 1 μm to about 10 μm, or in a range of about 2 μm to about 6 μm, and, e.g., in a range of about 3 μm to about 5 μm. Hereinafter, duplicative description will not be repeated and the description will focus on differences between the embodiments being described and those described herein above.

According to an embodiment, the first semiconductor layer 31" may extend in a direction and end portions thereof may be formed to be inclined toward a central portion thereof. The first semiconductor layer 31" may have a rod-shaped or cylindrical main body and end portions having inclined side surfaces on upper and lower portions of the main body. An upper end portion of the main body may have a slope that is steeper than that of a lower end portion thereof.

The active layer 36" may be disposed to surround an outer surface of the main body of the first semiconductor layer 31". The active layer 36" may have an annular shape extending in a direction. The active layer 36" may not be formed on the upper and lower end portions of the first semiconductor layer 31". The active layer 36" may be formed on only a non-inclined side surface of the first semiconductor layer 31". However, the disclosure is not limited thereto. Accordingly, light emitted from the active layer 36" may be emitted to not only end portions of the light emitting element 30" in a length direction but also side surfaces thereof based on the length direction. When compared with the light emitting element 30 of FIG. 28, the light emitting element 30" of FIG. 36 may include the active layer 36" having a larger area, thereby emitting a larger amount of light.

The second semiconductor layer 32" may be disposed to surround an outer surface of the active layer 36" and the upper end portion of the first semiconductor layer 31". The second semiconductor layer 32" may include an annular main body extending in a direction and an upper end portion having an inclined side surface. For example, the second semiconductor layer 32" may directly contact a side surface of the active layer 36" parallel thereto and the inclined upper end portion of the first semiconductor layer 31". However, the second semiconductor layer 32" is not formed in the lower end portion of the first semiconductor layer 31".

The electrode layer 37" may be disposed to surround an outer surface of the second semiconductor layer 32". For example, the electrode layer 37" and the second semiconductor layer 32" may be substantially a same shape. For example, the electrode layer 37" may entirely contact the outer surface of the second semiconductor layer 32".

The insulating layer 38" may be disposed to surround outer surfaces of the electrode layer 37" and the first semiconductor layer 31". The insulating layer 38" may directly contact the electrode layer 37", the lower end portion of the first semiconductor layer 31", and exposed lower end portions of the active layer 36" and the second semiconductor layer 32".

A display device 10 with a uniform number of light emitting elements 30 disposed in each pixel PX and each sub-pixel PXn may be manufactured using the inkjet printing device 1000 according to an embodiment. In the display device 10, a deviation in the number of light emitting devices 30 per each pixel PX and each sub-pixel PXn may be minimized, and light emission reliability for each pixel PX may be improved.

In concluding the detailed description, those skilled in the art will appreciate that many variations and modifications can be made to the embodiments without substantially departing from the principles of the disclosure. Therefore, the disclosed embodiments of the disclosure are used in a generic and descriptive sense only and not for purposes of limitation.

What is claimed is:

1. An inkjet printing device comprising:
   a stage;
   an inkjet head disposed above the stage and comprising nozzles through which ink is ejected, the ink comprising bipolar elements extending in a direction;
   an ink circulation part supplying the ink to the inkjet head, and supplied with the ink remaining after the ink is ejected from the inkjet head; and
   at least one sensing part disposed between the inkjet head and the ink circulation part and measuring a number of the bipolar elements ejected through the nozzles.

2. The inkjet printing device of claim 1, wherein
   the at least one sensing part comprises a light emitting part emitting light to the ink, and
   a light receiving part spaced apart from and facing the light emitting part and receiving the light emitted from the light emitting part.

3. The inkjet printing device of claim 2, wherein
   an outer wall of the nozzles is made of at least one transparent material,
   at least part of the light emitted to the ink is scattered by the bipolar elements, and
   the light receiving part measures the number of the bipolar elements by receiving the light emitted from the light emitting part and the scattered light.

4. The inkjet printing device of claim 3, wherein
   the at least one sensing part detects a change in the number of the bipolar elements in the ejected ink, and the ink circulation part receives the detected change in the number of bipolar elements from the at least one sensing part.

5. The inkjet printing device of claim 3, further comprising:
connection tubes connecting the ink circulation part and the inkjet head,
wherein the at least one sensing part is disposed on the connection tube.

6. The inkjet printing device of claim 2, wherein the inkjet head comprises:
a base part;
an ejecting part which is a portion of the base part and in which the nozzles are disposed; and
an inner tube supplied with the ink,
the light emitting part and the light receiving part of the at least one sensing part disposed on the ejecting part, and
at least one of the nozzles is disposed between the light emitting part and the light receiving part of the at least one sensing part.

7. The inkjet printing device of claim 6, wherein
each of the nozzles comprises:
an inlet connected to the inner tube and through which the ink is introduced, and
an outlet connected to the inlet and through which the ink is ejected,
the inkjet head further comprises an actuator disposed on the ejecting part and surrounding the nozzles, and
the at least one sensing part comprises a first sensing part disposed between the actuator and the inner tube and adjacent to the inlet of the at least one of the nozzles.

8. The inkjet printing device of claim 7, wherein
the at least one sensing part further comprises a second sensing part spaced apart from the first sensing part, and
the actuator is disposed between the first and second sensing parts and adjacent to the outlet.

9. The inkjet printing device of claim 7, wherein
the at least one sensing part further comprises a third sensing part in which the light emitting part and the light receiving part are disposed on the base part, and
the inner tube is disposed between the third sensing part and the base part.

10. The inkjet printing device of claim 6, wherein
the light receiving part is disposed in the ejecting part,
the light emitting part is disposed on an outer surface of the base part, and
the at least one sensing part further comprises a light transmitting part disposed in the ejecting part, disposed between the at least one of the nozzles and the light emitting part, and transmitting the light emitted from the light emitting part into the at least one of the nozzles.

11. The inkjet printing device of claim 2, wherein the inkjet head further comprises an electric field generating electrode generating an electric field in the nozzles.

12. A printing method of a bipolar element, comprising:
preparing an ink circulation part storing ink in which bipolar elements are dispersed and supplying the ink to an inkjet head;
ejecting the ink from the inkjet head and measuring a number of bipolar elements in the ejected ink; and
controlling the number of the bipolar elements in the ink supplied to the inkjet head in case that the number of the bipolar elements in the ink exceeds a reference set value.

13. The printing method of claim 12, wherein
the measuring of the number of the bipolar elements is performed by at least one sensing part disposed between the inkjet head and the ink circulation part, and
the at least one sensing part comprises:
a light emitting part emitting light to the ink, and
a light receiving part spaced apart from and facing the light emitting part and receiving the light emitted from the light emitting part.

14. The printing method of claim 13, wherein
at least part of the light emitted to the ink is scattered by the bipolar elements, and
the light receiving part measures the number of the bipolar elements by being irradiated with the light emitted from the light emitting part and the scattered light.

15. The printing method of claim 13, wherein
the controlling of the number of the bipolar elements in the ink comprises receiving, at the ink circulation part, a change in the number of the bipolar elements detected by the at least one sensing part, and
controlling, at the ink circulation part, a degree of dispersion of the bipolar elements in the ink.

16. The printing method of claim 13, further comprising spraying the ink ejected from the inkjet head onto a target substrate and disposing the bipolar elements on the target substrate.

17. The printing method of claim 16, wherein
the spraying of the bipolar elements onto the target substrate is conducted using an inkjet printing device,
wherein the inkjet printing device comprises:
a stage;
the inkjet head disposed above the stage and comprising nozzles through which the ink, is ejected, the ink comprising the bipolar elements extending in a direction;
the ink circulation part supplying the ink to the inkjet head, and supplied with the ink remaining after the ink is ejected from the inkjet head; and
the at least one sensing part disposed between the inkjet head and the ink circulation part and measuring the number of the bipolar elements ejected through the nozzles.

18. A method of manufacturing a display device, comprising:
preparing a target substrate on which a first electrode and a second electrode are formed;
spraying ink in which light emitting elements are dispersed onto the target substrate while controlling a number of the light emitting elements dispersed in the ink; and
disposing the light emitting elements onto the first electrode and the second electrode.

19. The method of claim 18, wherein the controlling of the number of the light emitting elements dispersed in the ink comprises:
measuring the number of the light emitting elements in the ink sprayed onto the target substrate and
controlling the number of the light emitting elements dispersed in the ink in case that the number of the light emitting elements in the ink exceeds a reference set value.

20. The method of claim 19, wherein the measuring of the number of the light emitting elements comprises:
emitting light to the ink;

receiving the light and scattered light scattered by the light emitting element from at least part of the light emitted to the ink; and measuring the number of the light emitting elements from the light and the scattered light.

* * * * *